(12) United States Patent
Lu et al.

(10) Patent No.: US 10,693,075 B2
(45) Date of Patent: Jun. 23, 2020

(54) SPIRO COMPOUND AND ORGANIC ELECTRONIC DEVICE COMPRISING THE SAME

(71) Applicant: NICHEM FINE TECHNOLOGY CO., LTD., Jhubei, Hsinchu County (TW)

(72) Inventors: Tai-Ni Lu, Jhubei (TW); Liang-Di Liao, Jhubei (TW); Shwu-Ju Shieh, Jhubei (TW); Chi-Chung Chen, Jhubei (TW)

(73) Assignee: SHANGHAI NICHEM FINE CHEMICAL CO., LTD., Shanghai (CN)

( * ) Notice: Subject to any disclaimer, the term of this patent is extended or adjusted under 35 U.S.C. 154(b) by 18 days.

(21) Appl. No.: 15/670,174

(22) Filed: Aug. 7, 2017

(65) Prior Publication Data

US 2018/0047907 A1 Feb. 15, 2018

Related U.S. Application Data

(60) Provisional application No. 62/372,417, filed on Aug. 9, 2016.

(51) Int. Cl.
*H01L 51/00* (2006.01)
*C07C 255/50* (2006.01)
(Continued)

(52) U.S. Cl.
CPC ........ *H01L 51/0057* (2013.01); *C07B 59/002* (2013.01); *C07C 255/50* (2013.01);
(Continued)

(58) Field of Classification Search
CPC ...... H01L 51/0057; H01L 51/00; H01L 35/24
(Continued)

(56) References Cited

U.S. PATENT DOCUMENTS 6,229,012 B1 * 5/2001 Hu .................. C07D 251/24
544/180
8,318,888 B1 * 11/2012 Tan .................. C09K 11/06
528/73
(Continued)

FOREIGN PATENT DOCUMENTS

CN 105778891 A 7/2016
JP 2010-24149 A 2/2010
(Continued)

OTHER PUBLICATIONS

Chien-Tien Chen, "Spirally configured cis-stilbene/fluorene hybrids as ambipolar, fluorescent materials for organic light emitting diode applications", RSC Adv., 2013, 3, 9381-9390 (Year: 2013).*
(Continued)

*Primary Examiner* — Caleb E Henry
(74) *Attorney, Agent, or Firm* — Birch, Stewart, Kolasch & Birch, LLP

(57) ABSTRACT

Provided are a novel compound and an organic electronic device using the same. The novel compound is represented by the following Formula (I):

Formula (I)

(Continued)

wherein $X^1$ and $X^2$ are each independently $C(R^a)$, multiple $(R^a)$s are the same or different, and the two $(R^a)$s are joined together to form an aryl ring;

wherein $X^3$ and $X^4$ are each independently $C(R^b)$, multiple $(R^b)$s are the same or different, and the two $(R^b)$s are joined together to form a polycyclic aromatic ring.

20 Claims, 19 Drawing Sheets

(51) Int. Cl.

| | |
|---|---|
| *C07C 255/51* | (2006.01) |
| *C07D 213/57* | (2006.01) |
| *C07D 233/58* | (2006.01) |
| *C07D 239/74* | (2006.01) |
| *C07D 251/24* | (2006.01) |
| *C07B 59/00* | (2006.01) |
| *C07D 307/94* | (2006.01) |
| *C07D 333/80* | (2006.01) |
| *C07D 405/04* | (2006.01) |
| *C07D 409/04* | (2006.01) |
| *C07D 409/14* | (2006.01) |
| *H01L 51/50* | (2006.01) |
| *H01L 51/52* | (2006.01) |

(52) U.S. Cl.
CPC .......... *C07C 255/51* (2013.01); *C07D 213/57* (2013.01); *C07D 233/58* (2013.01); *C07D 239/74* (2013.01); *C07D 251/24* (2013.01); *C07D 307/94* (2013.01); *C07D 333/80* (2013.01); *C07D 405/04* (2013.01); *C07D 409/04* (2013.01); *C07D 409/14* (2013.01); *H01L 51/0065* (2013.01); *H01L 51/0067* (2013.01); *H01L 51/0072* (2013.01); *H01L 51/0073* (2013.01); *H01L 51/0074* (2013.01); *C07B 2200/05* (2013.01); *H01L 51/001* (2013.01); *H01L 51/006* (2013.01); *H01L 51/0061* (2013.01); *H01L 51/0077* (2013.01); *H01L 51/0085* (2013.01); *H01L 51/5012* (2013.01); *H01L 51/5016* (2013.01); *H01L 51/5056* (2013.01); *H01L 51/5072* (2013.01); *H01L 51/5076* (2013.01); *H01L 51/5088* (2013.01); *H01L 51/5092* (2013.01); *H01L 51/5096* (2013.01); *H01L 51/5206* (2013.01); *H01L 51/5221* (2013.01)

(58) Field of Classification Search
USPC .......................................................... 257/40
See application file for complete search history.

(56) References Cited

U.S. PATENT DOCUMENTS

| | | | |
|---|---|---|---|
| 8,735,528 B1 * | 5/2014 | Tan | H05B 33/14 |
| | | | 528/73 |
| 8,921,844 B2 * | 12/2014 | Chen | H01L 51/006 |
| | | | 257/40 |
| 9,209,413 B1 * | 12/2015 | Chen | H01L 51/0067 |
| 9,755,154 B2 * | 9/2017 | Chen | H01L 51/0056 |
| 10,193,083 B2 * | 1/2019 | Chen | C07D 471/10 |
| 2016/0111648 A1 * | 4/2016 | Chen | C07C 255/58 |
| | | | 558/384 |
| 2016/0111649 A1 | 4/2016 | Chen et al. | |
| 2017/0040547 A1 * | 2/2017 | Chen | C07D 471/10 |
| 2017/0040548 A1 * | 2/2017 | Chen | C07C 255/52 |
| 2017/0213972 A1 * | 7/2017 | Liao | C07D 213/22 |
| 2018/0040830 A1 * | 2/2018 | Chen | C09K 11/06 |
| 2018/0040831 A1 * | 2/2018 | Chen | H01L 51/0067 |
| 2018/0273840 A1 * | 9/2018 | Chen | H01L 51/0057 |
| 2018/0298279 A1 * | 10/2018 | Lee | C09K 11/06 |

FOREIGN PATENT DOCUMENTS

| | | |
|---|---|---|
| KR | 10-2012-0093076 A | 8/2012 |
| KR | 10-2012-0122897 A | 11/2012 |
| KR | 10-2012-0135501 A | 12/2012 |
| KR | 10-2013-0110347 A | 10/2013 |
| TW | 201625532 A | 7/2016 |

OTHER PUBLICATIONS

REGISTRY(STN), CAS 1394820-41-7, Sep. 18, 2012.
REGISTRY(STN), CAS 1394820-42-8, Sep. 18, 2012.
REGISTRY(STN), CAS 1403832-80-3, Nov. 14, 2012.
REGISTRY(STN), CAS 1411549-36-4, Dec. 5, 2012.
REGISTRY(STN), CAS 1417313-60-0, Jan. 23, 2013.

\* cited by examiner

SPIRO COMPOUND AND ORGANIC ELECTRONIC DEVICE COMPRISING THE SAME

CROSS-REFERENCE TO RELATED APPLICATION

Pursuant to 35 U.S.C. § 119(e), this application claims the benefits of the priority to U.S. Provisional Patent Application No. 62/372,417, filed Aug. 9, 2016. The contents of the prior applications are incorporated herein by its entirety.

BACKGROUND OF THE INVENTION

1. Field of the Invention

The present invention relates to a novel compound and an organic electronic device using the same, more particularly to a novel compound as electron-transporters and an organic electronic device using the same.

2. Description of the Prior Arts

With the advance of technology, various organic electronic devices that make use of organic materials have been energetically developed. Examples of organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching Tang and Steven VanSlyke of Kodak Company deposited an electron transport material such as tris(8-hydroxyquinoline)aluminum (III) (abbreviated as $Alq_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of back light, and low power consumption. However, the OLEDs still have the problems such as low efficiency and short lifetime.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 moves to the EL via HIL and HTL and the electrons injected from the cathode 18 moves to the EL via EIL and ETL. Recombination of the electrons and the holes occurs in the EL to generate excitons, thereby emitting a light when the excitons decays from excited state to ground state.

Another approach is to modify the materials of ETL for OLEDs to render the electron transport materials to exhibit hole-blocking ability. Examples of conventional electron transport materials include 3,3'-[5'-[3-(3-Pyridinyl)phenyl][1,1':3',1''-terphenyl]-3,3''-diyl]bispyridine (TmPyPb), 3-(Biphenyl-4-yl)-5-(4-tert-butylphenyl)-4-phenyl-4H-1,2,4-triazole (TAZ), 1,3,5-tris(1-phenyl-1H-benzimidazol-2-yl)benzene (TPBO, tris(2,4,6-trimethyl-3-(pyridin-3-yl)phenyl)borane (3TPYMB), 1,3-bis(3,5-dipyrid-3-yl-phenyl)benzene (BmPyPb), and 9,10-bis(3-(pyridin-3-yl)phenyl)anthracene (DPyPA).

However, even using the foresaid electron transport materials, the current efficiency of OLEDs still needs to be improved. Therefore, the present invention provides a novel compound to mitigate or obviate the problems in the prior art.

SUMMARY OF THE INVENTION

An objective of the present invention is to provide a novel compound useful for an organic electronic device.

Another objective of the present invention is to provide an organic electronic device using the novel compound, so as to improve the efficiency of the organic electronic device.

To achieve the foresaid objectives, the present invention provides a novel compound represented by the following Formula (I):

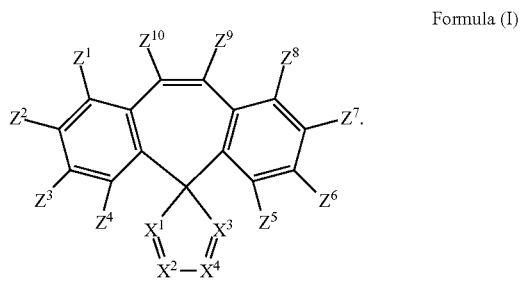

Formula (I)

In Formula (I), $X^1$ and $X^2$ are each independently $C(R^a)$, the two $(R^a)$s are the same or different, and the two $(R^a)$s are joined together to form an aryl ring;

In Formula (I), $X^3$ and $X^4$ are each independently $C(R^b)$, the two $(R^b)$s are the same or different, and the two $(R^b)$s are joined together to form a polycyclic aromatic ring;

In Formula (I), $Z^1$ to $Z^{10}$ are each independently selected from the group consisting of: a hydrogen atom, a deuterium atom, a trifluoromethyl group, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atoms, a phosphine group having 1 to 40 carbon atoms, and a phosphine oxide group having 1 to 40 carbon atoms.

In accordance with the present invention, the polycyclic aromatic ring extended from $X^3$ and $X^4$ in Formula (I) contains at least two cyclic aryl rings joined or fused together. The at least two cyclic aryl rings of the polycyclic aromatic ring are all constructed by carbon atoms without any heteroatom such as nitrogen, oxygen or sulfur atoms, while the polycyclic aromatic ring may be attached with any substitution group containing atoms other than carbon atom.

In accordance with the present invention, the double bond between $X^1$ and $X^2$ in Formula (I) and the bonds between the two joined ($R^a$)s are conjugated and commonly construct the aryl ring. Likely, the double bond between $X^3$ and $X^4$ in Formula (I) and the bonds between the two joined ($R^b$)s are conjugated and commonly construct the polycyclic aromatic ring. In accordance with the present invention, the aryl ring extended from $X^1$ and $X^2$ and the polycyclic aromatic ring extended from $X^3$ and $X^4$ are joined and fused to become an aromatic group containing at least six conjugated double bonds, preferably become an aromatic group containing at least eight conjugated double bonds.

The aryl ring extended from $X^1$ and $X^2$ in Formula (I) may be a substituted or unsubstituted 6 to 60-membered carbon ring, preferably a substituted or unsubstituted 6 to 20-membered carbon ring. For example, the substituted or unsubstituted 6 to 60-membered carbon ring may be, for example, a substituted or unsubstituted benzene ring, a substituted or unsubstituted naphthalene ring, a substituted or unsubstituted anthracene ring, a substituted or unsubstituted phenanthrene ring, a substituted or unsubstituted fluorene ring, a substituted or unsubstituted pyrene ring, a substituted or unsubstituted benzophenanthrene ring, a substituted or unsubstituted benzopyrene ring, a substituted or unsubstituted fluoranthene ring, a substituted or unsubstituted benzofluoranthene ring, but is not limited thereto. More preferably, the substituted or unsubstituted 6 to 60-membered carbon aromatic ring is a substituted or unsubstituted benzene ring. The substitution group on the 6 to 60-membered carbon ring may be, but not limited to, a deuterium atom, a halogen group, a cyano group, a nitro group, an alkyl group having 1 to 12 carbon atoms, an alkenyl group having 2 to 12 carbon atoms, or an alkynyl group having 2 to 12 carbon atoms.

The polycyclic aromatic ring extended from $X^3$ and $X^4$ may be, for example, but not limited to: a substituted or unsubstituted naphthalene ring, a substituted or unsubstituted anthracene ring, a substituted or unsubstituted phenanthrene ring, a substituted or unsubstituted fluorene ring, a substituted or unsubstituted pyrene ring, a substituted or unsubstituted benzophenanthrene ring, a substituted or unsubstituted benzopyrene ring, a substituted or unsubstituted fluoranthene ring, or a substituted or unsubstituted benzofluoranthene ring. The foresaid polycyclic aromatic ring may be substituted with at least one deuterium atom, at least one alkyl group having 1 to 12 carbon atoms, at least one alkenyl group having 2 to 12 carbon atoms, at least one alkynyl group having 2 to 12 carbon atoms, or at least one aryl group having 6 to 12 ring carbon atoms. For example, the substituted fluorene ring may be a fluorene ring substituted with one methyl group, two methyl groups, or two phenyl groups, i.e., the substituted fluorene ring may be 9-methylfluorene ring, 9,9-dimethylfluorene ring, or 9,9-diphenylfluorene ring.

For example, the compound is represented by

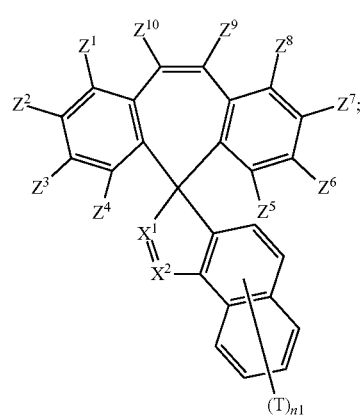

Formula (I-I)

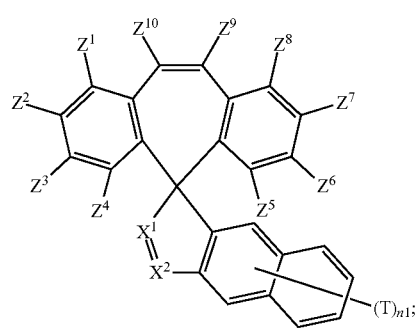

Formula (I-II)

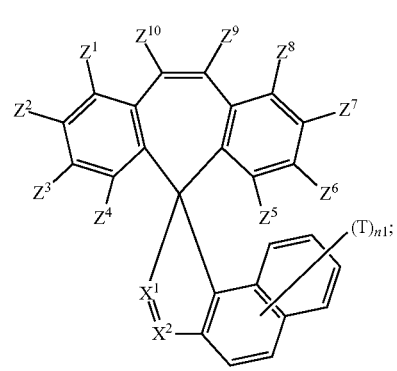

Formula (I-III)

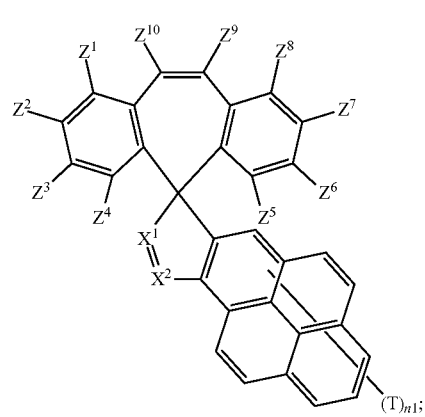

Formula (I-IV)

-continued
Formula (I-V)
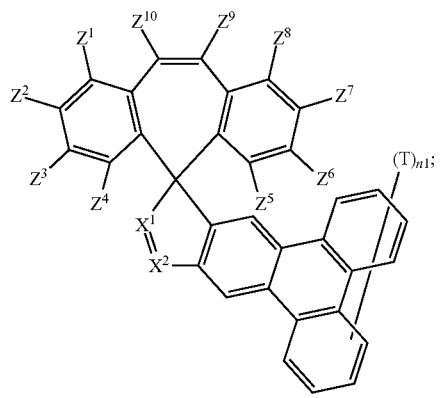
Formula (I-VI)
Formula (I-VII)
Formula (I-VIII)
-continued
Formula (I-IX)
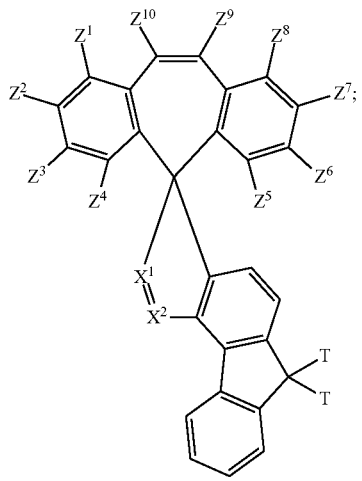
Formula (I-X)
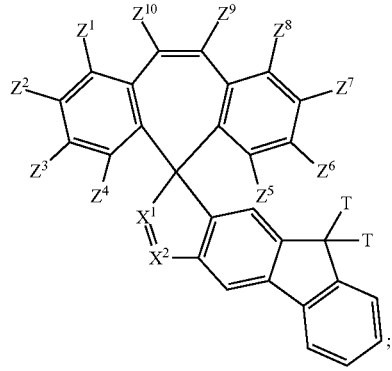
Formula (I-XI)
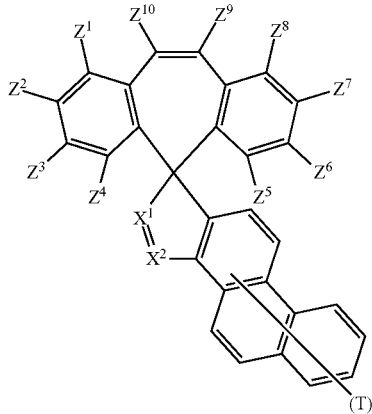
or

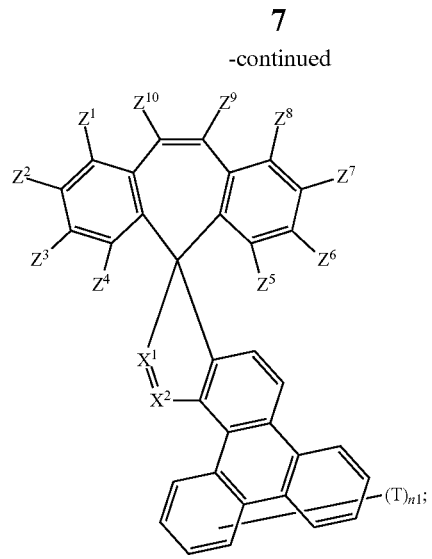

Formula (I-XII)

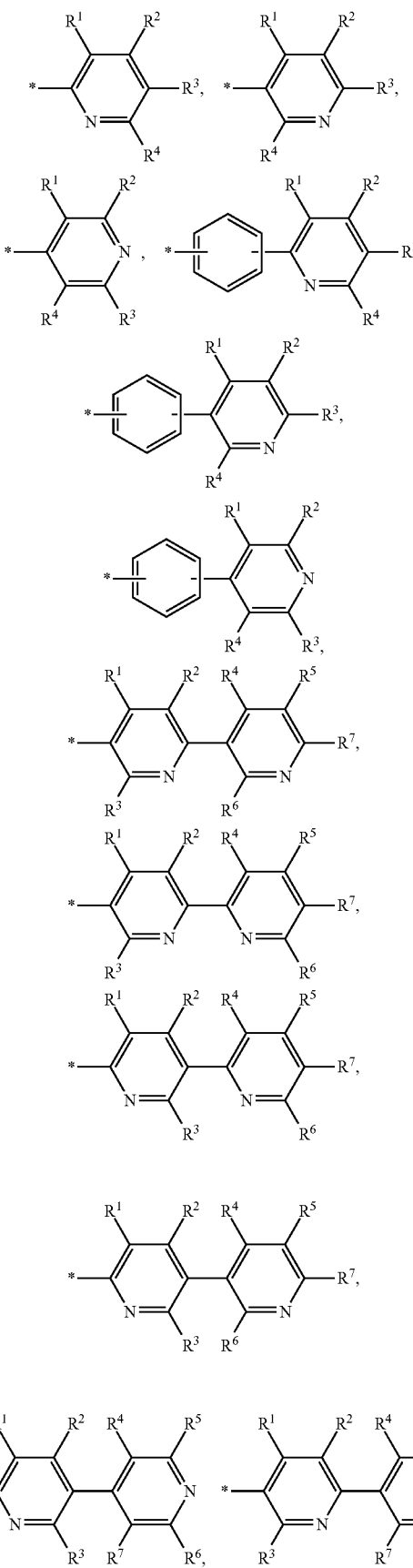

In the above Formulae, n1 may be a positive integral from 0 to 4, T may be, for example, but not limited to: a hydrogen atom, a deuterium atom, a methyl group, an ethyl group, a propyl group, a butyl group, a pentyl group, a hexyl group, or a phenyl group.

Preferably, at least one of $Z^1$ to $Z^8$ in formula (I) may be selected from the group consisting of: an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an aryl group having 6 to 60 ring carbon atoms and substituted with at least one functional group, a heteroaryl group having 3 to 60 ring carbon atoms containing at least one nitrogen atom, an alkoxy group having 1 to 40 carbon atoms and substituted with at least one functional group, an aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to 40 carbon atoms and substituted with at least one functional group, an arylboron group having 6 to 60 ring carbon atoms, a phosphine group having 1 to 40 carbon atoms and substituted with at least one functional group, and a phosphine oxide group having 1 to 40 carbon atoms and substituted with at least one functional group; and the others of $Z^1$ to $Z^8$ in formula (I) may be a hydrogen atom, a deuterium atom, or any other substitution groups as mentioned in the specification. Said functional group is selected from the group consisting of: a cyano group, a nitro group, a trifluoromethyl group, a fluoro group, and a chloro group.

More specifically, at least one of $Z^1$ to $Z^8$ in Formula (I) may be a specific aromatic substitution. The specific aromatic substitution may be, for example, but not limited to:

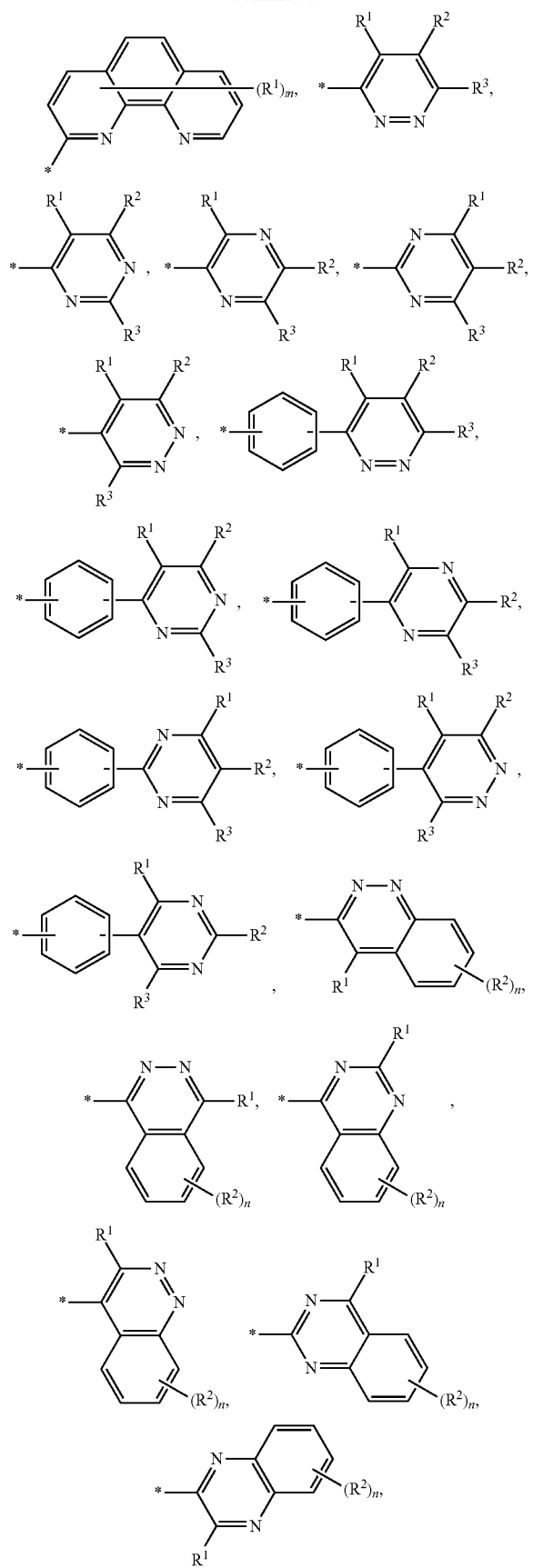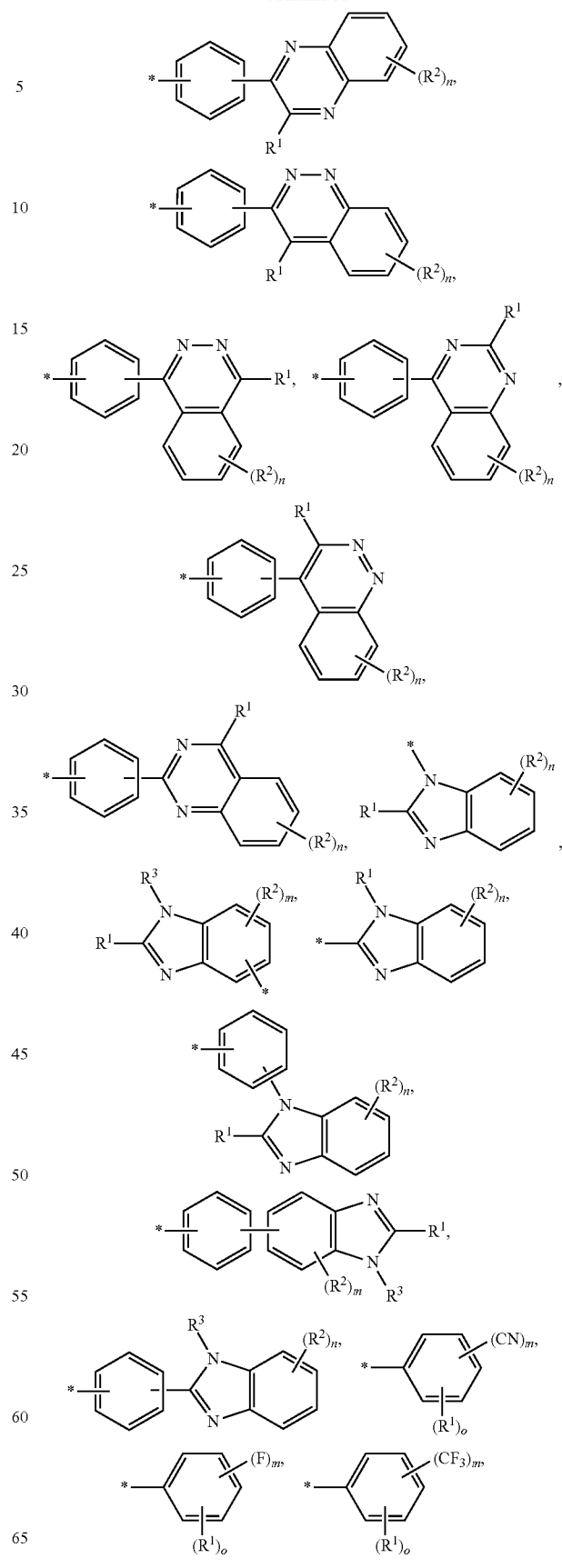

-continued

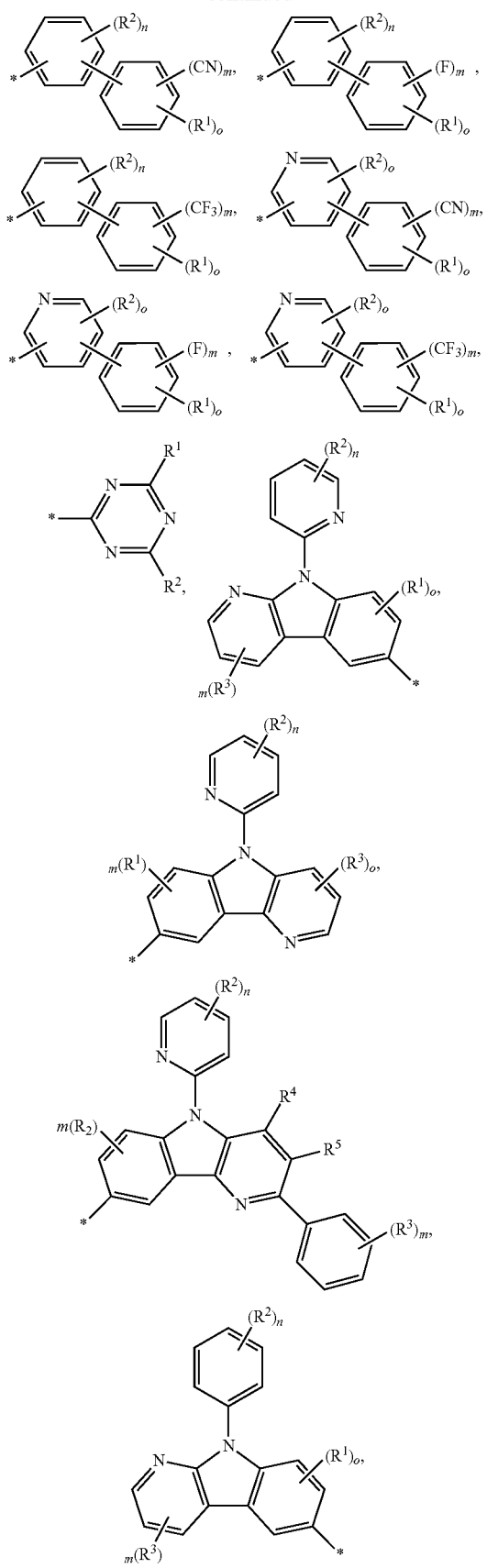

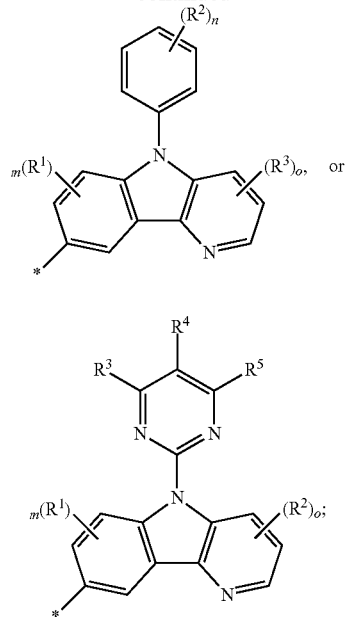

wherein R¹ to R⁷ are each independently selected from the group consisting of: a hydrogen atom, a deuterium atom, a trifluoromethyl group, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

n is a positive integral from 0 to 4, m is a positive integral from 0 to 3, o is a positive integral from 0 to 3, and the total of m and o is not more than 5.

Preferably, R¹ to R³ each may independently be, for example, but not limited to, a phenyl group, a pyridine group, a pyrimidine group, a pyrazine group, a pyridazine group, a phenylpyridine group, a phenylpyrimidine group, a phenylpyrazine group, or a phenylpyridazine group.

Preferably, at least one of $Z^1$, $Z^2$, $Z^3$, $Z^6$, $Z^7$, and $Z^8$ in Formula (I) may be the specific aromatic substitution as stated above, and $Z^4$ and $Z^5$ are each independently selected from the group consisting of: a hydrogen atom, a deuterium atom, an alkyl group having 1 to 12 carbon atoms, an alkenyl group having 2 to 12 carbon atoms, and an alkynyl group having 2 to 12 carbon atoms. Or, at least one of $Z^2$, $Z^3$, $Z^6$, and $Z^7$ in Formula (I) may be the specific aromatic substitution as stated above, and $Z^1$, $Z^4$, $Z^5$, $Z^8$ are each independently selected from the group consisting of: a hydrogen atom, a deuterium atom, an alkyl group having 1 to 12 carbon atoms, an alkenyl group having 2 to 12 carbon atoms, and an alkynyl group having 2 to 12 carbon atoms.

More specifically, at least one of $Z^2$, $Z^3$, $Z^6$, and $Z^7$ in Formula (I) may be, for example, but not limited to:
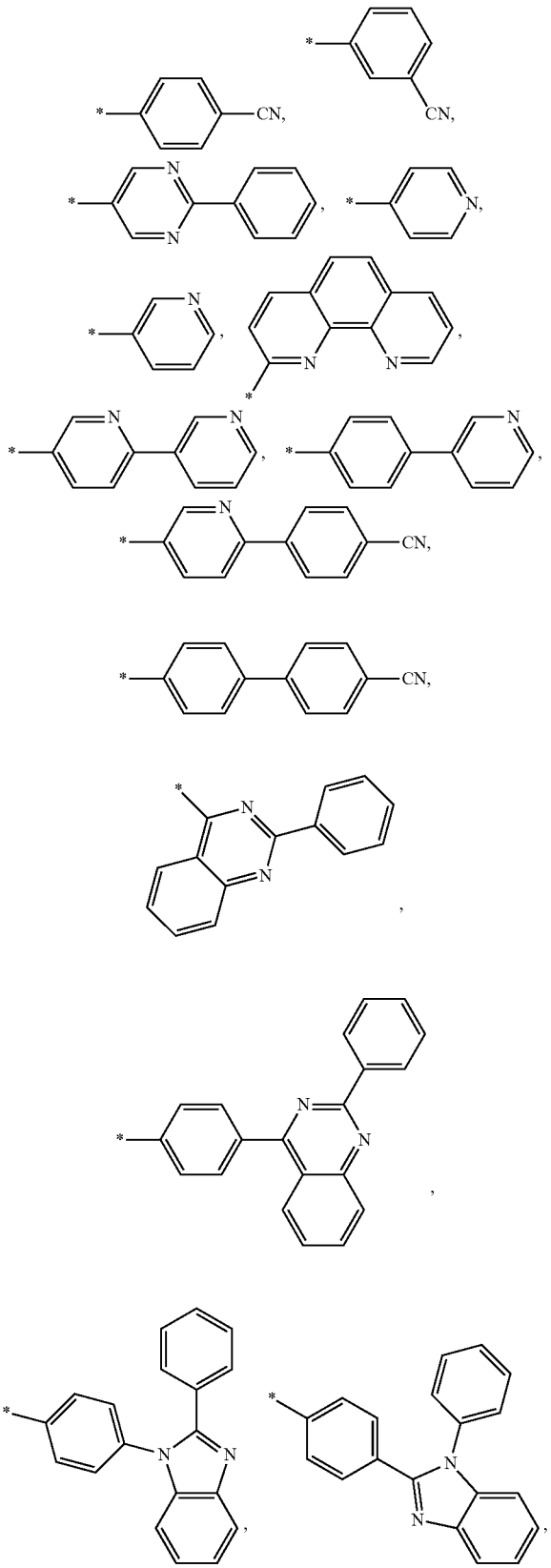
-continued
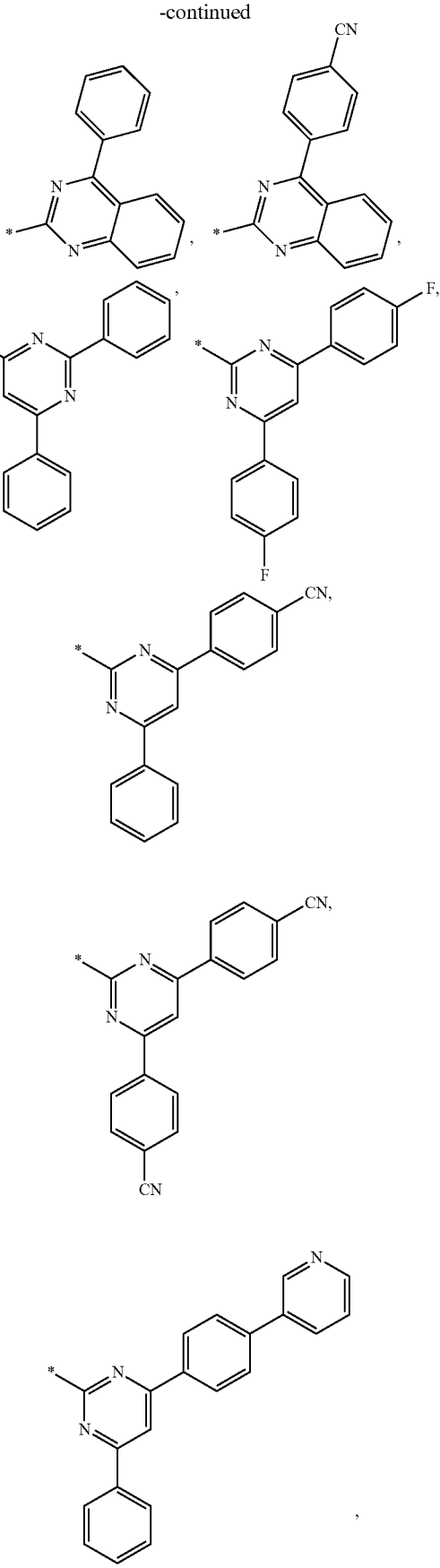

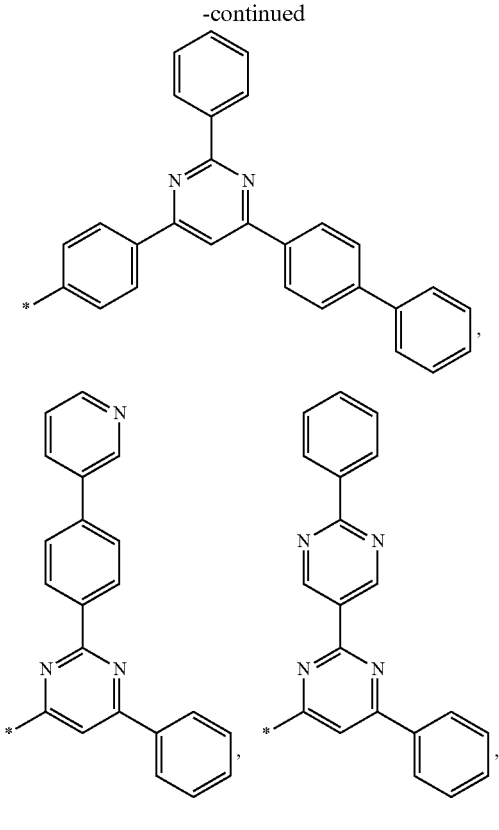

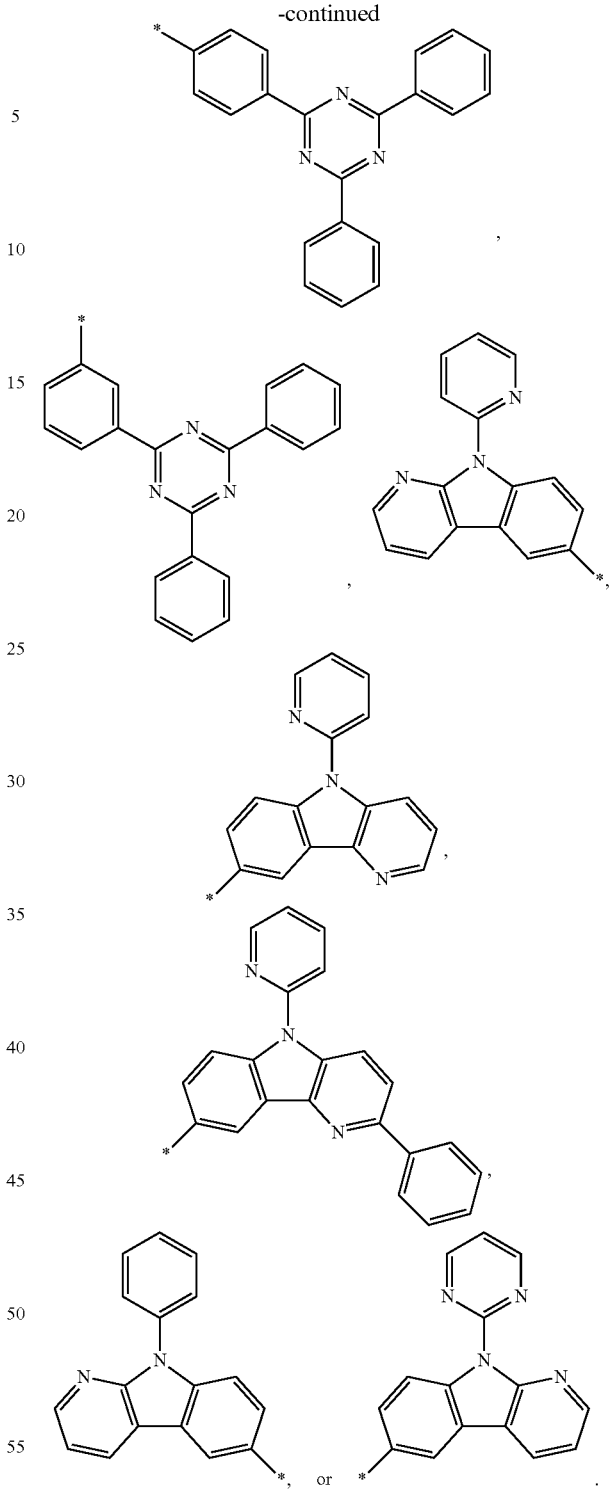

More preferably, at least one of $Z^1$, $Z^2$, $Z^3$, $Z^6$, $Z^7$, and $Z^8$ in Formula (I) may be a triazine group substituted with two phenyl groups, two pyridine groups, two pyrimidine groups, two pyrazine groups, two pyridazine groups, two phenylpyridine groups, two phenylpyrimidine groups, two phenylpyrazine groups, or two phenylpyridazine groups.

In accordance with the present invention, $Z^1$ and $Z^8$ may be the same or different. In accordance with the present invention, $Z^2$ and $Z^7$ may be the same or different. In accordance with the present invention, $Z^3$ and $Z^6$ may be the same or different. In one embodiment, any two of $Z^1$, $Z^2$, $Z^3$, $Z^6$, $Z^7$, and $Z^8$ may be the same substitution as stated above, and the others of $Z^1$, $Z^2$, $Z^3$, $Z^6$, $Z^7$, and $Z^8$ may be a hydrogen atom, a deuterium atom, a halogen group, a cyano group, a nitro group, a trifluoromethyl group, an alkyl group having 1 to 12 carbon atoms, an alkenyl group having 2 to 12 carbon atoms, or an alkynyl group having 2 to 12 carbon atoms.

For example, $Z^1$, $Z^4$ to $Z^8$ are each independently a hydrogen atom or a deuterium atom, and $Z^2$ and/or $Z^3$ may be a specific aromatic substitution. Or, $Z^1$, $Z^2$, $Z^4$, $Z^5$, $Z^7$, and $Z^8$ are each independently a hydrogen atom or a deuterium atom, and $Z^3$ and $Z^6$ are both the above specific aromatic substitutions.

In the above Formulae, $Z^9$ and $Z^{10}$ may be the same or different. Preferably, $Z^9$ and $Z^{10}$ are each independently selected from the group consisting of: a hydrogen atom, deuterium atom, a trifluoromethyl group, a halogen group, a cyano group, a nitro group, an alkyl group having 1 to 40 carbon atoms, an alkenyl group having 2 to 40 carbon atoms, an alkynyl group having 2 to 40 carbon atoms, an aryl group having 6 to 60 ring carbon atoms, and a heteroaryl group having 3 to 60 ring carbon atoms. More preferably, $Z^9$ and $Z^{10}$ each may be a hydrogen atom, a deuterium atom, a trifluoromethyl group, a fluoro group, a bromo group, a cyano group, a nitro group, an alkyl group having 1 to 40 carbon atoms, an alkenyl group having 2 to 40 carbon atoms, an alkynyl group having 2 to 40 carbon atoms, an aryl group having 6 to 60 ring carbon atoms, and a heteroaryl group having 3 to 60 ring carbon atoms.

For example, the compound may be, for example, but not limited to:

Compound I

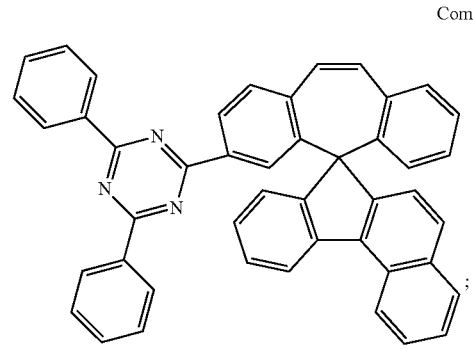

Compound II

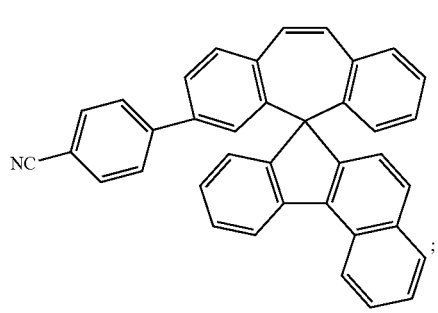

Compound III

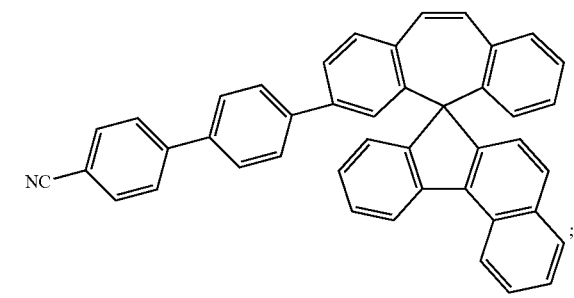

Compound IV

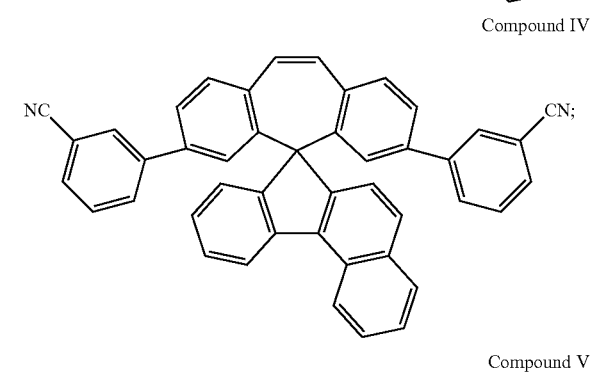

Compound V

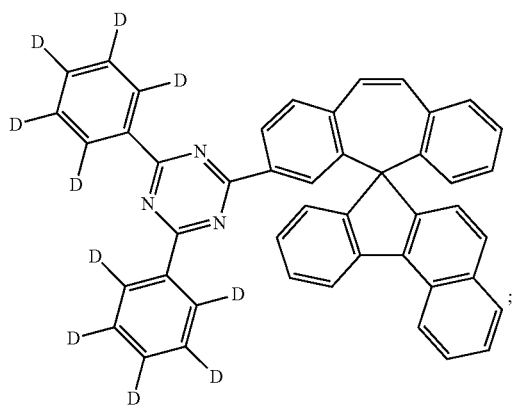

Compound VI

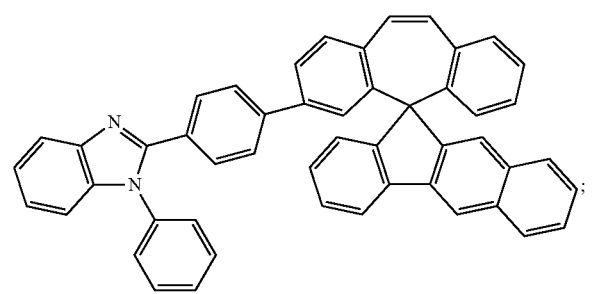

Compound VII

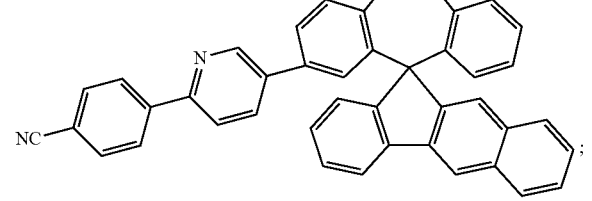

Compound VIII
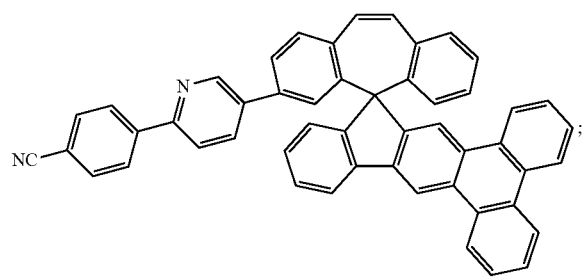
Compound IX
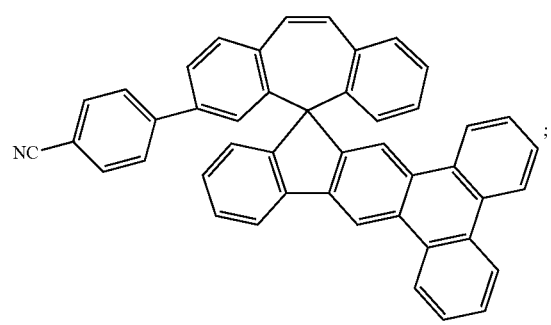
Compound X
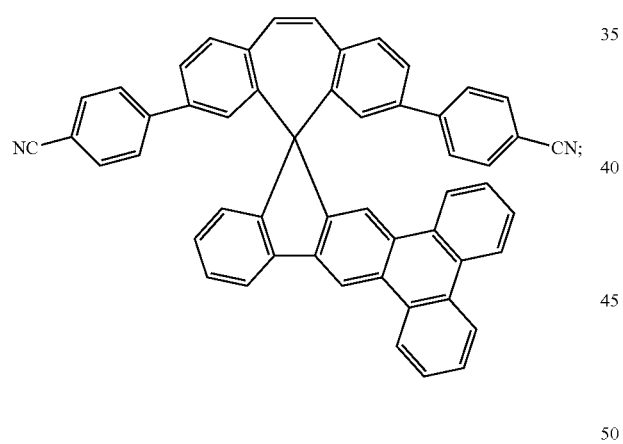
Compound XI
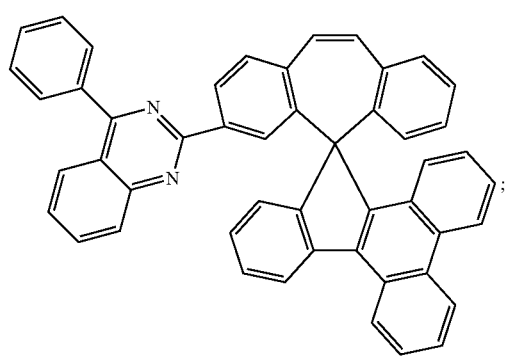
Compound XII
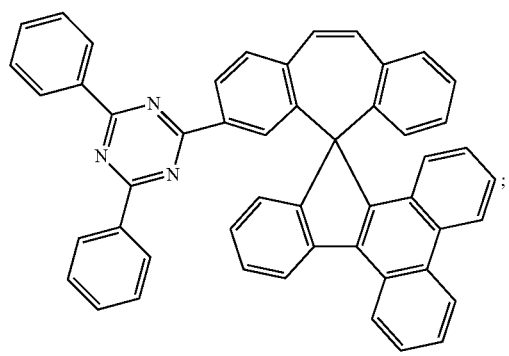
Compound XIII
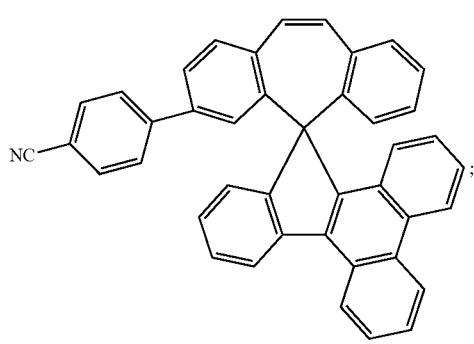
Compound XIV
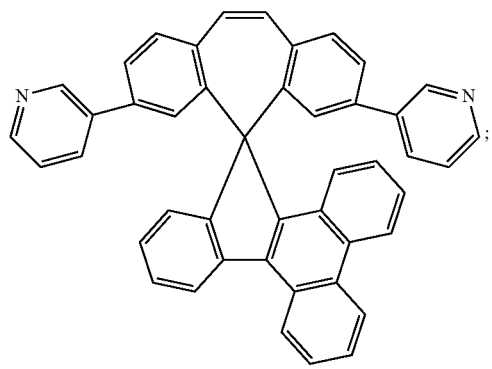
Compound XV
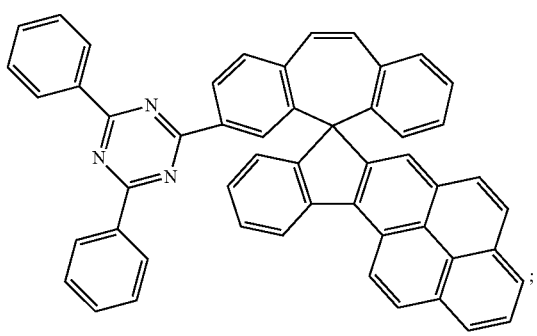

Compound XVI
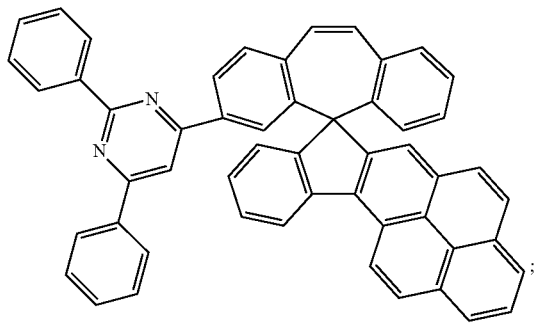
Compound XVII
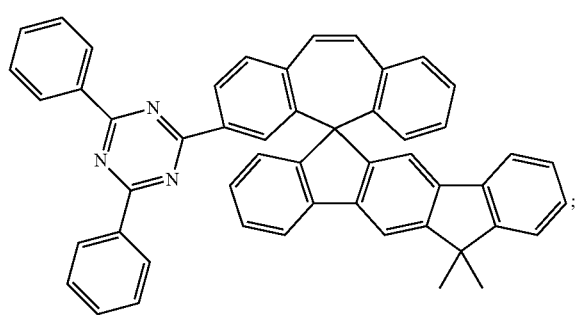
Compound XVIII
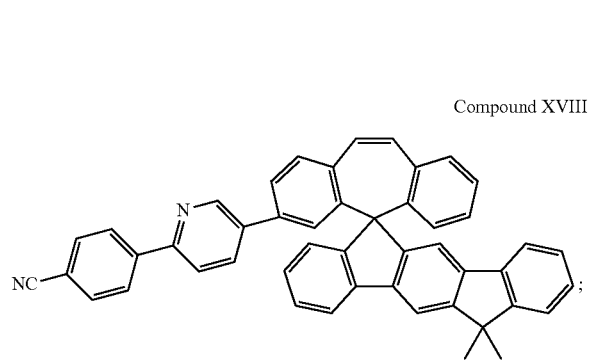
Compound XIX
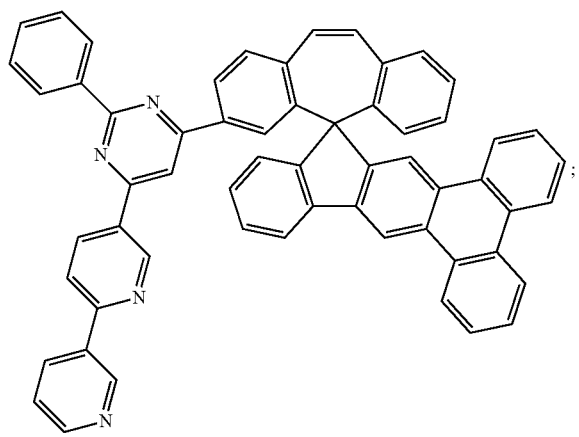
Compound XX
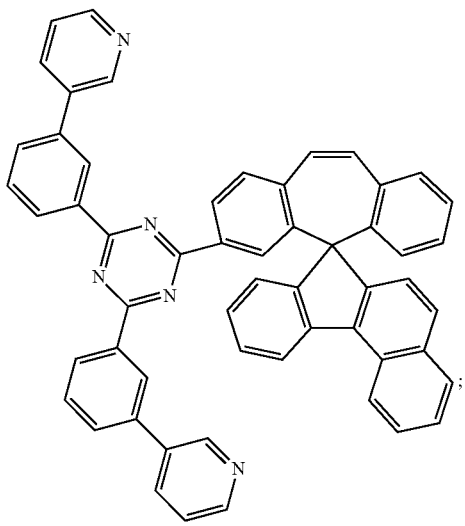
Compound XXI
Compound XXII
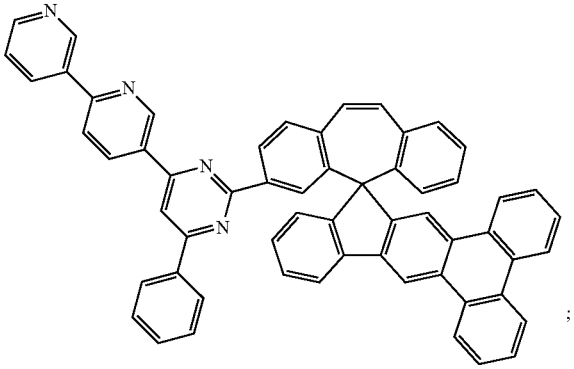

Compound XXIII
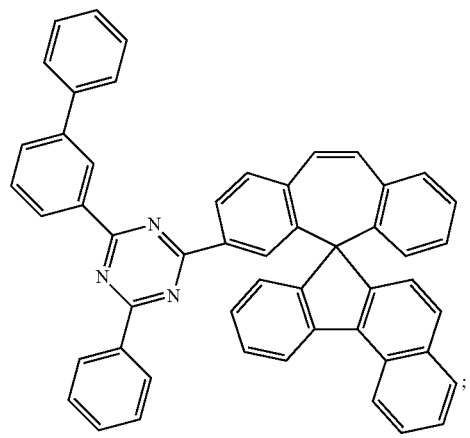
Compound XXIV
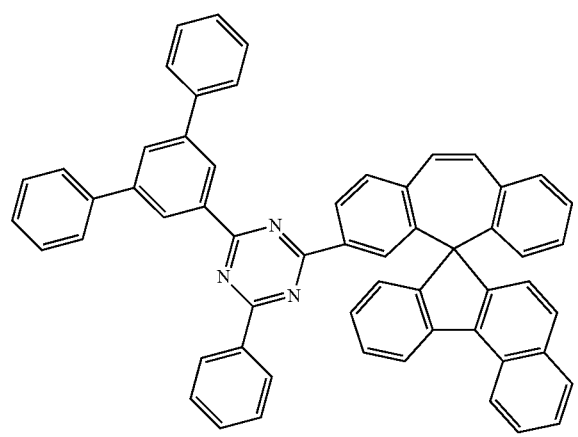
Compound XXV
Compound XXVI
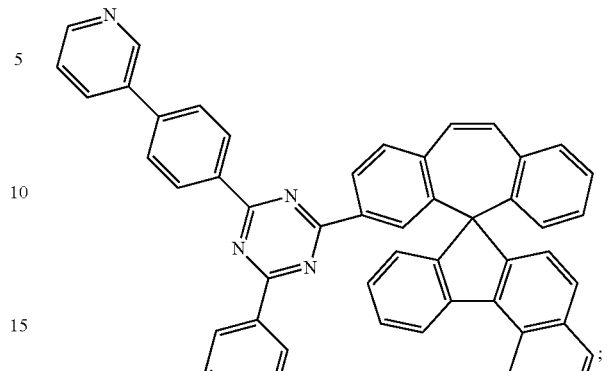
Compound XXVII
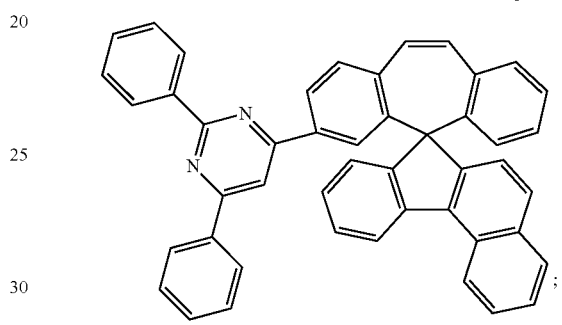
Compound XXVIII
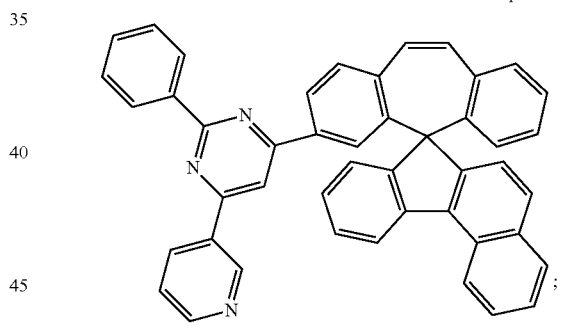
Compound XXIX
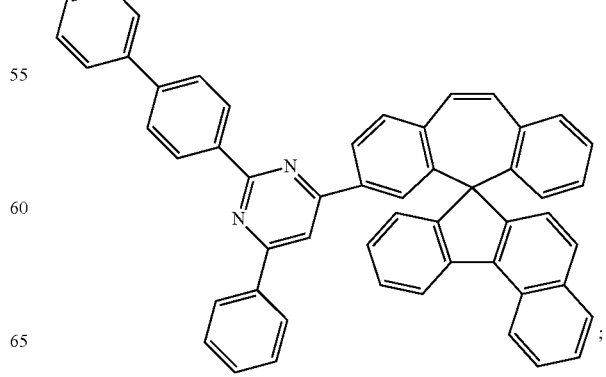

Compound XXX
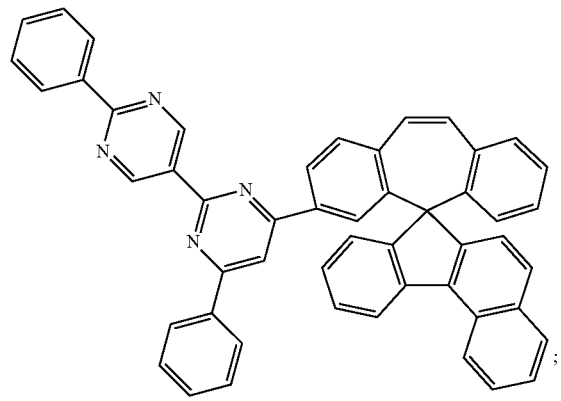
Compound XXXI
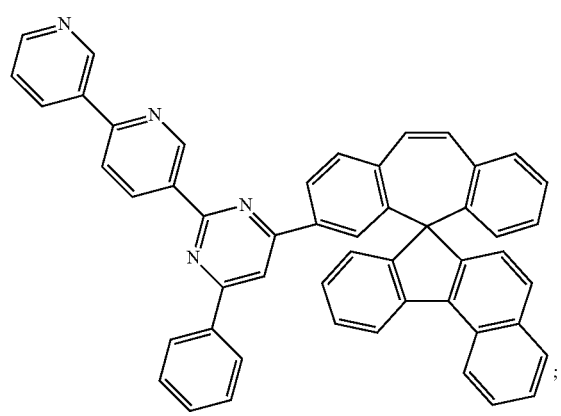
Compound XXXII
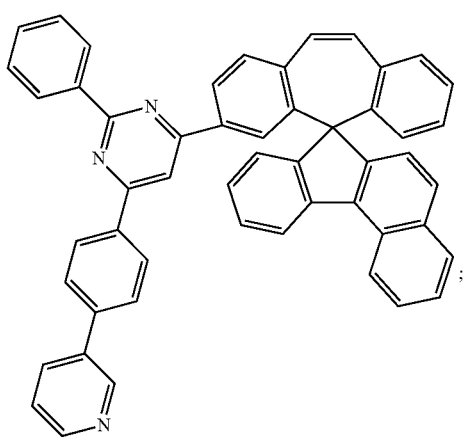
Compound XXXIII
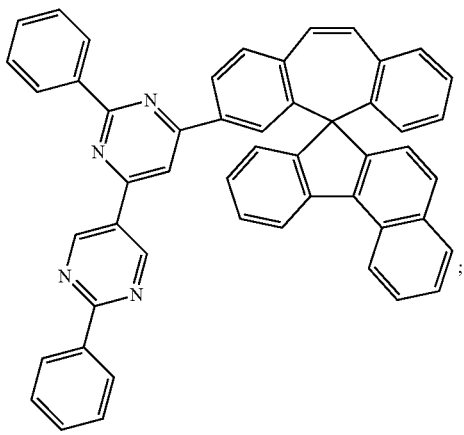
Compound XXXIV
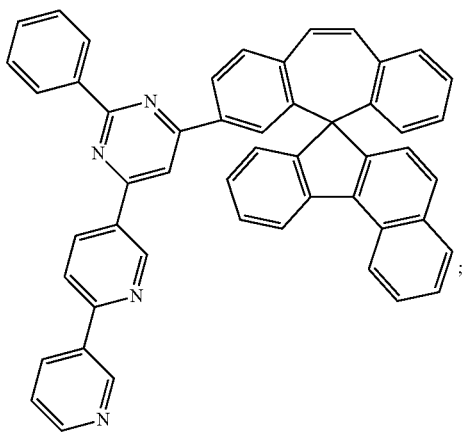
Compound XXXV
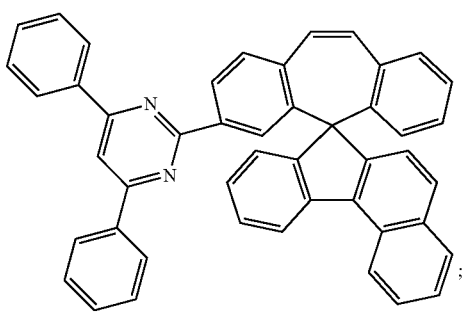
Compound XXXVI
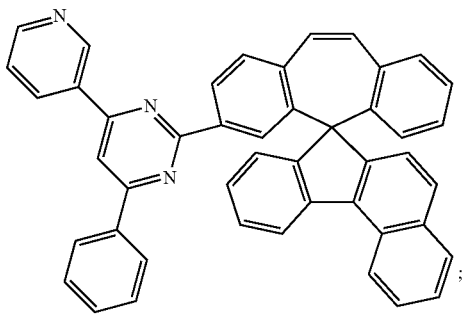

Compound XXXVII
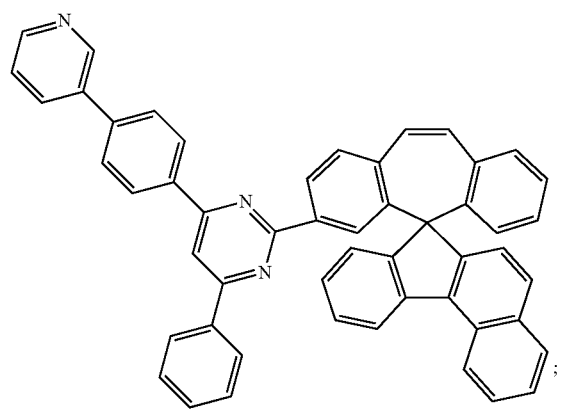
Compound XXXVIII
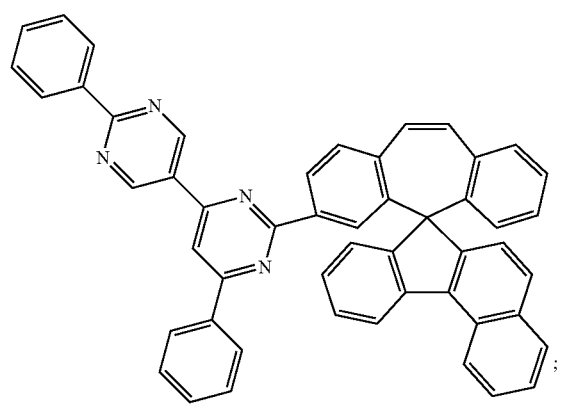
Compound XXXIX
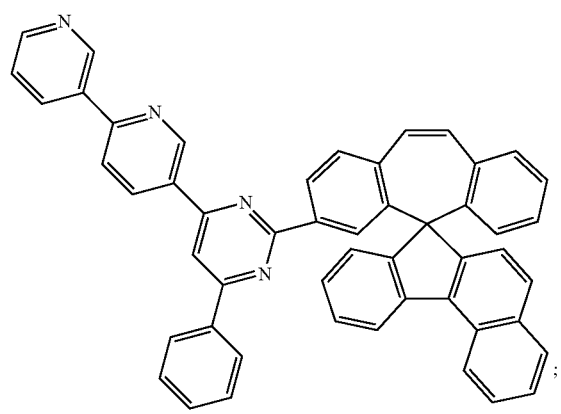
Compound XL
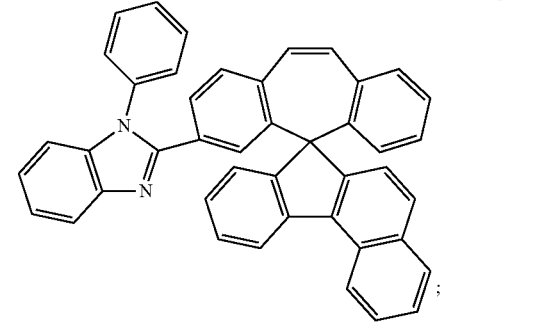
Compound XLI
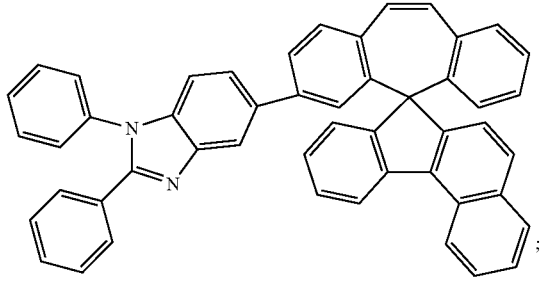
Compound XLII
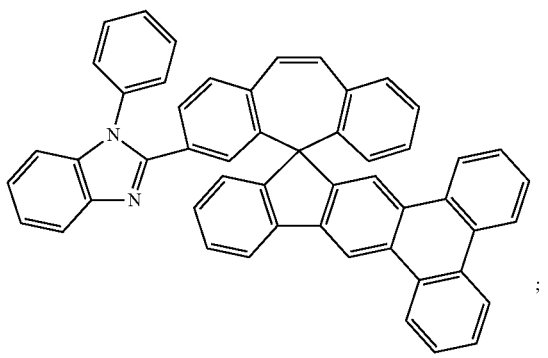
Compound XLIII
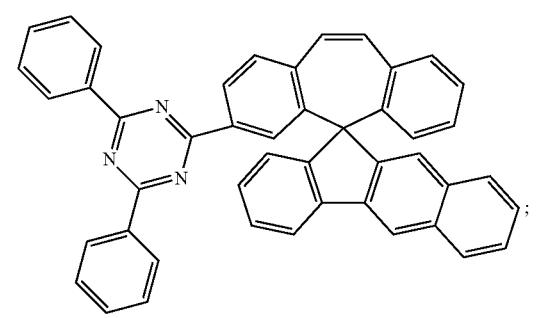
Compound XLIV
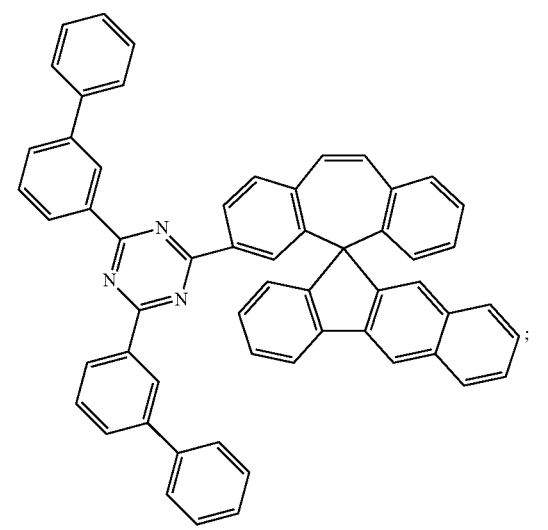

Compound XLV
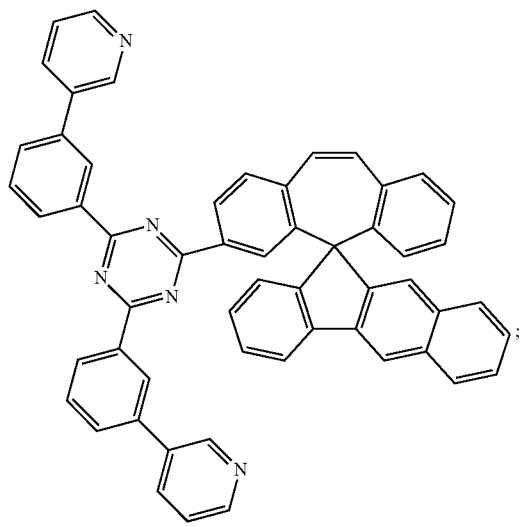
Compound XLVI
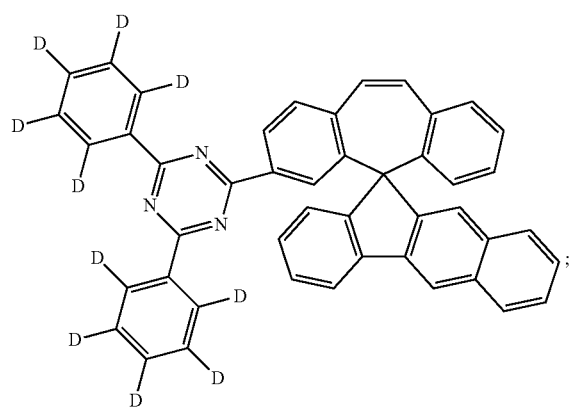
Compound XLVII
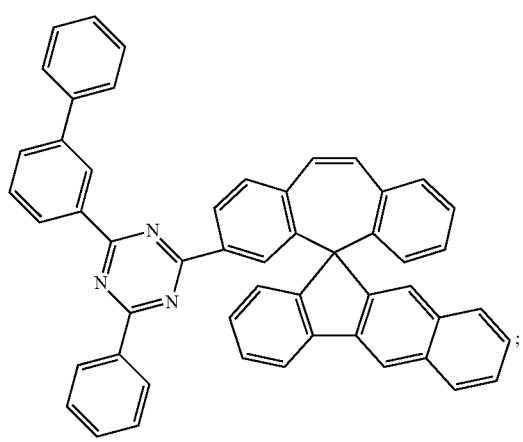
Compound XLVIII
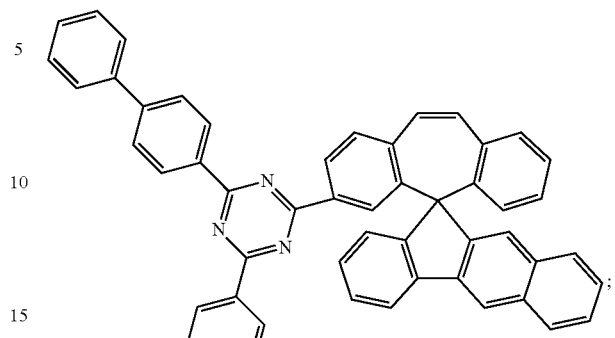
Compound IL
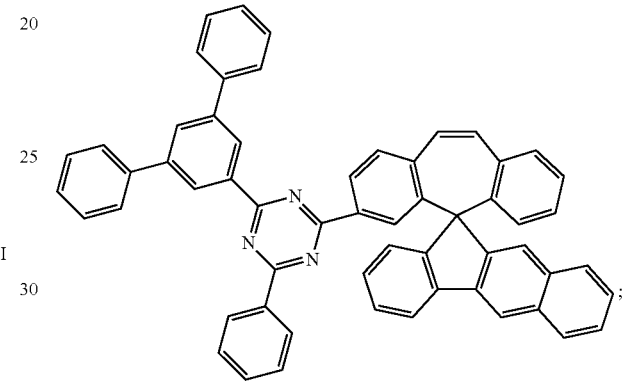
Compound L
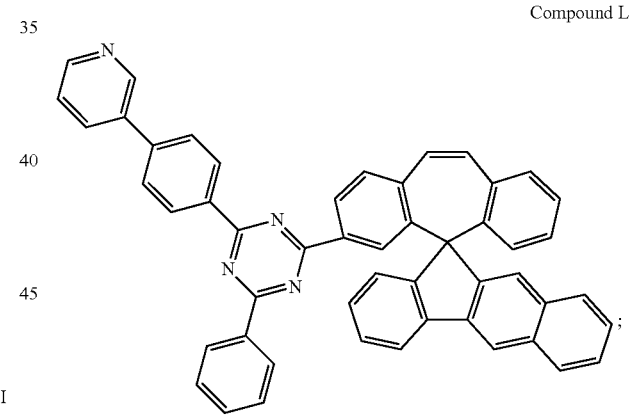
Compound LI
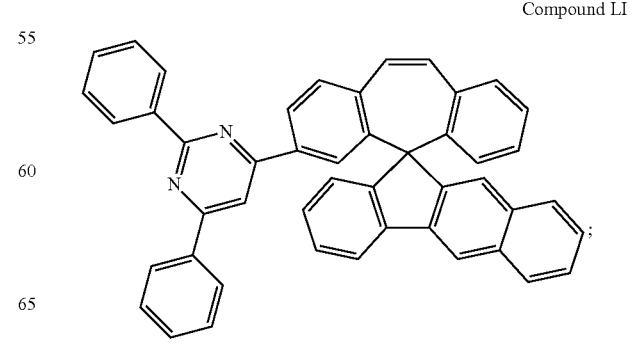

Compound LII
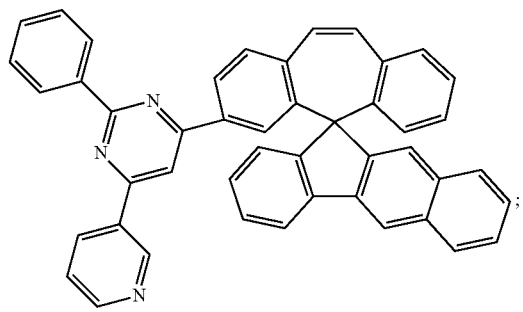
Compound LIII
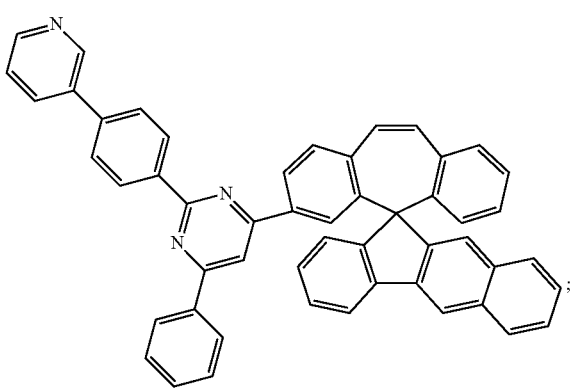
Compound LIV
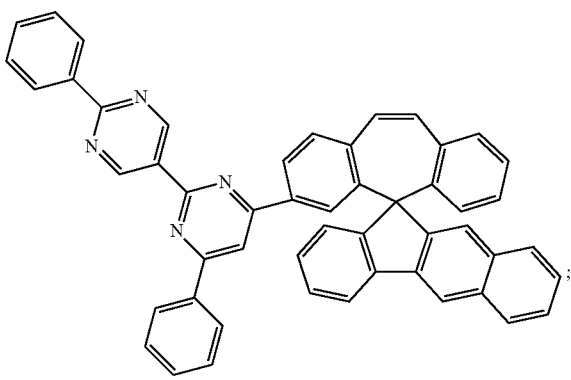
Compound LV
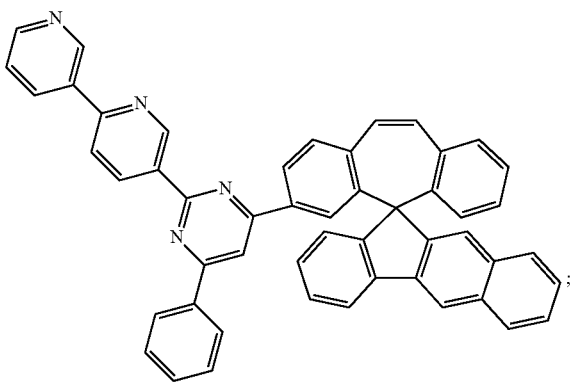
Compound LVI
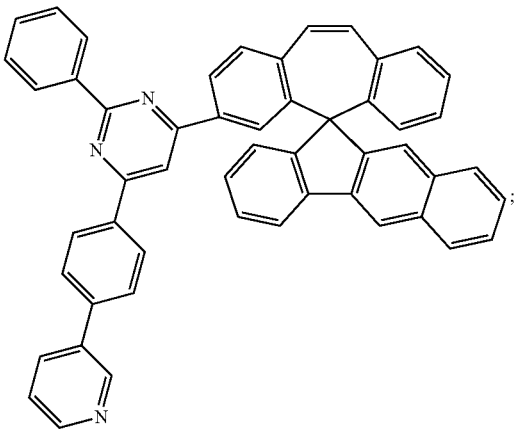
Compound LVII
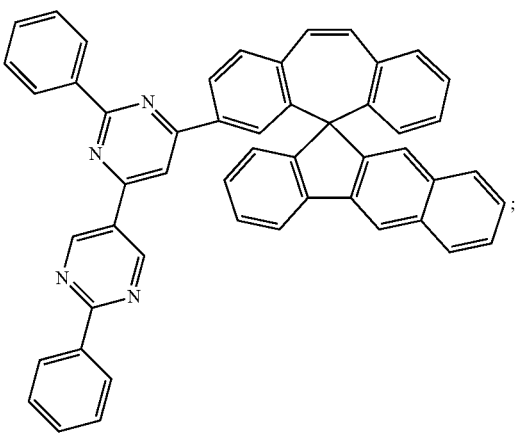
Compound LVIII
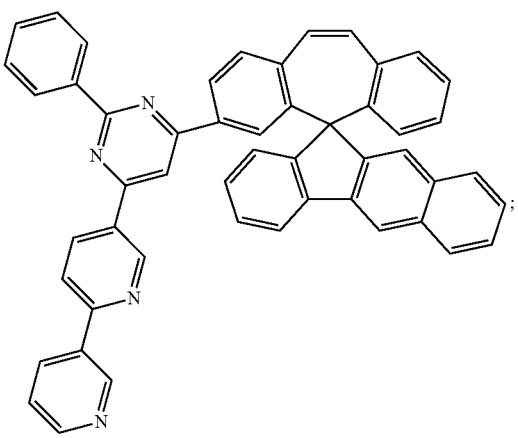

Compound LIX
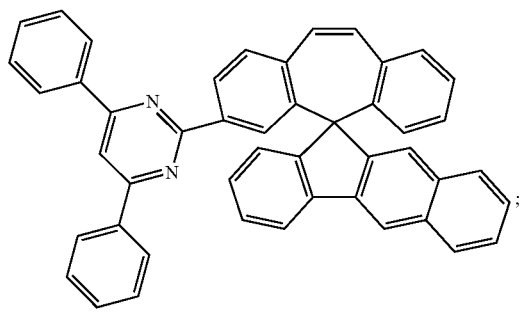
Compound LX
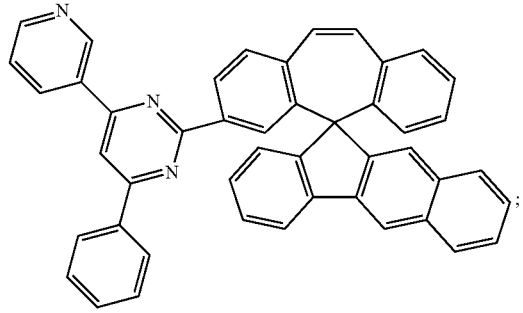
Compound LXI
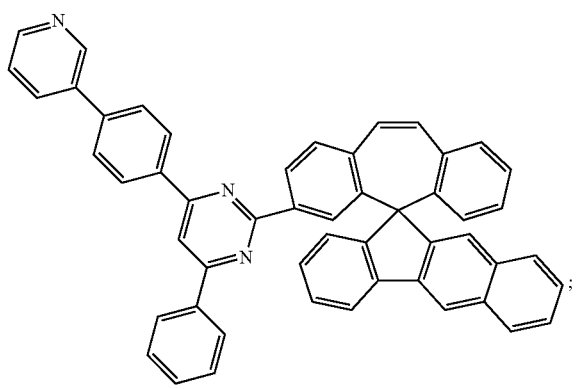
Compound LXII
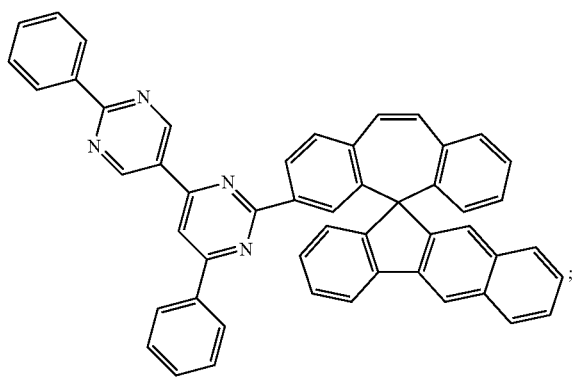
Compound LXIII
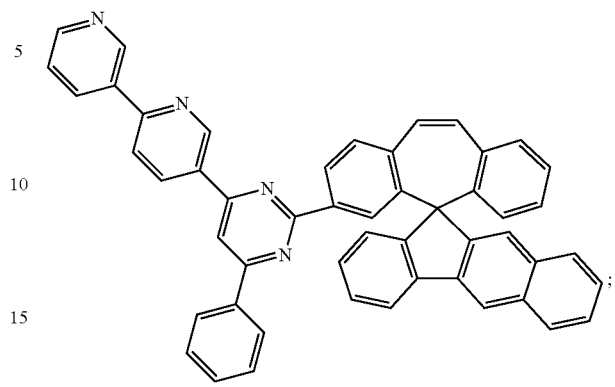
Compound LXIV
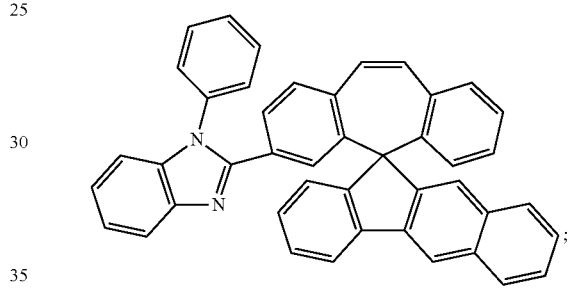
Compound LXV
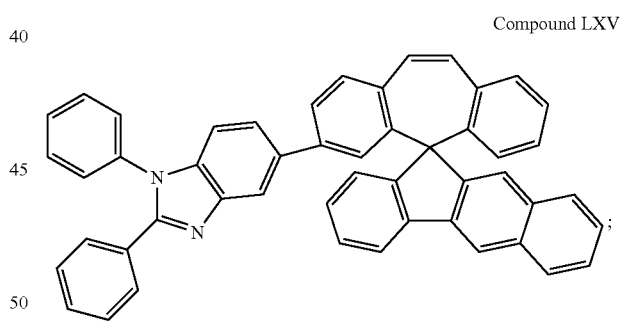
Compound LXVI
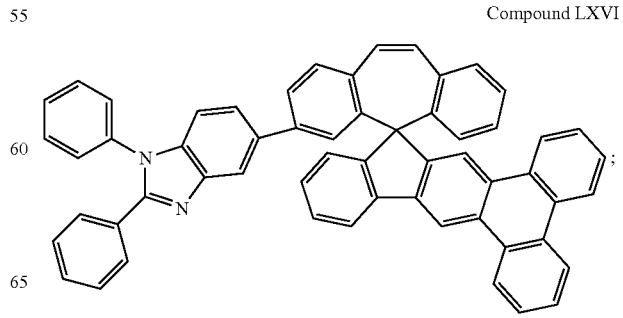

Compound LXVII
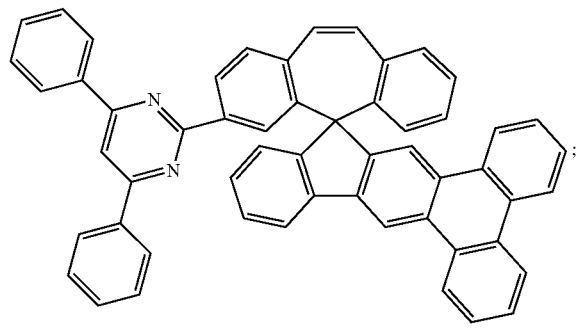
Compound LXVIII
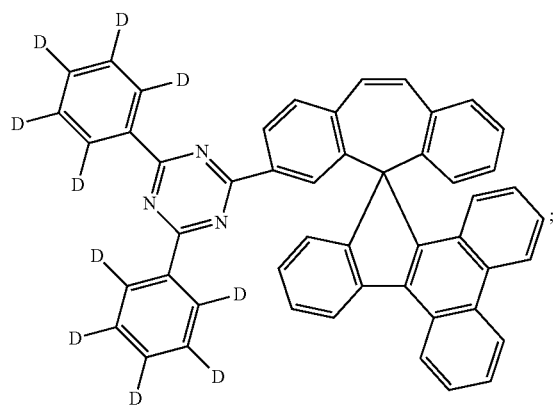
Compound LXIX
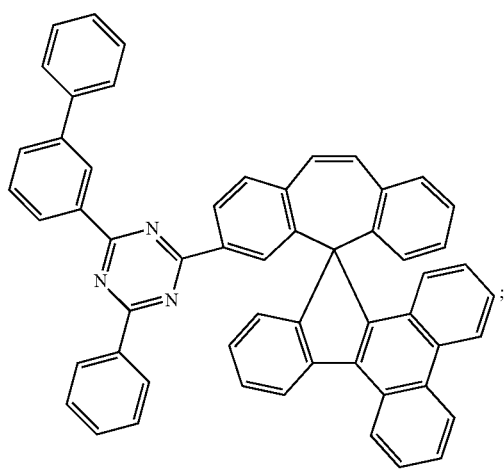
Compound LXX
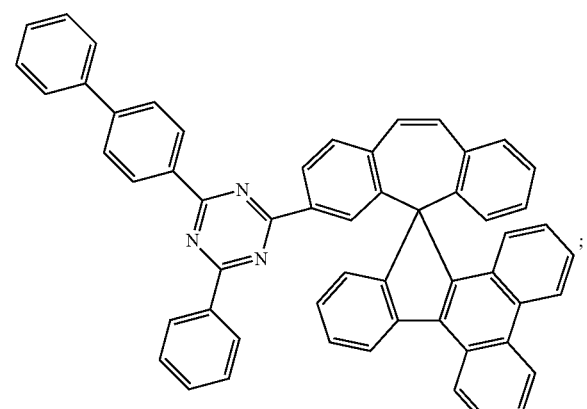
Compound LXXI
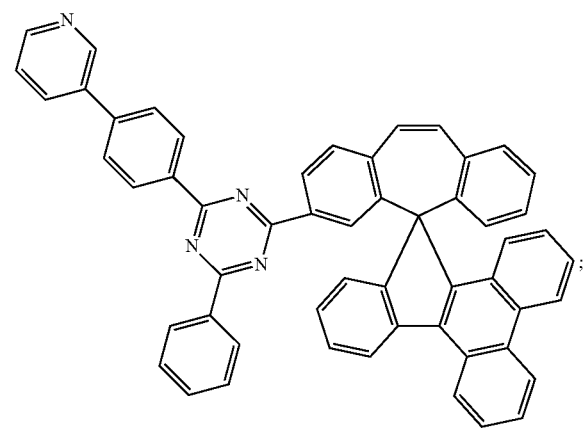
Compound LXXII
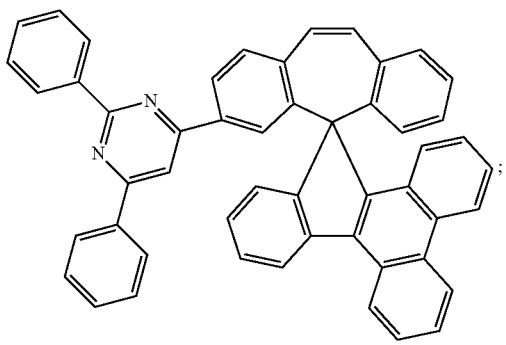
Compound LXXIII
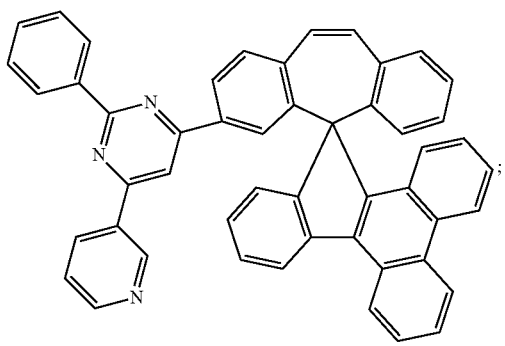

Compound LXXIV
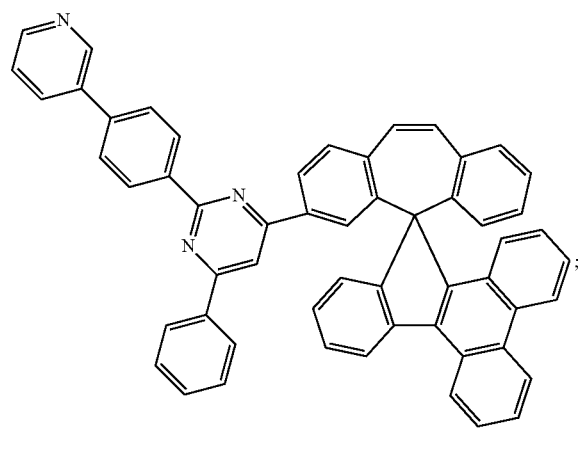
Compound LXXV
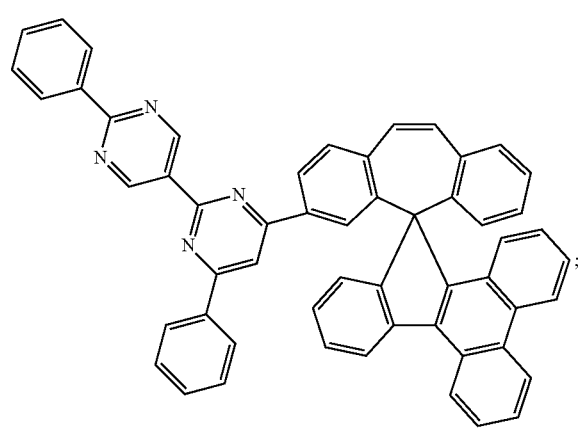
Compound LXXVI
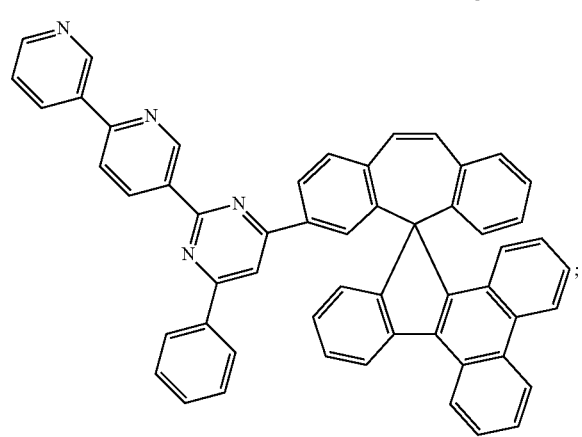
Compound LXXVII
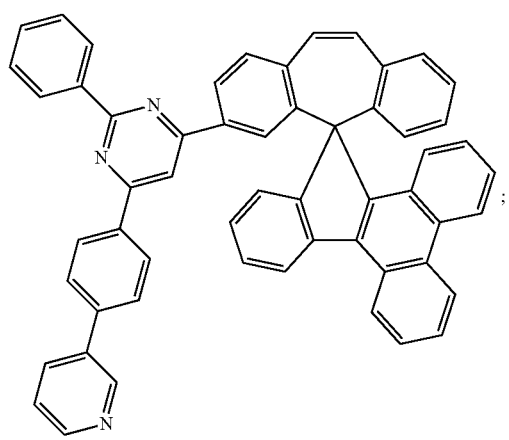
Compound LXXVIII
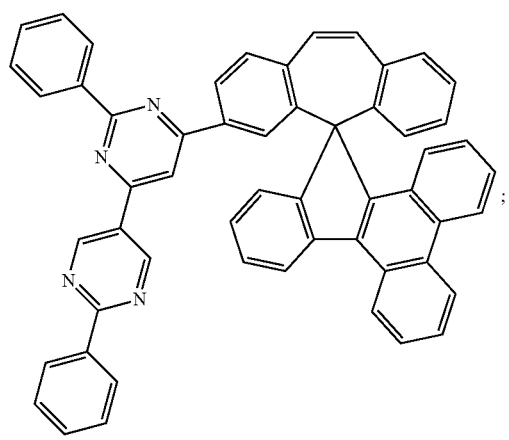
Compound LXXIX
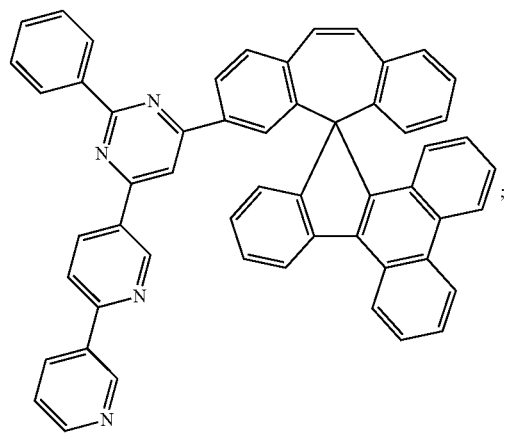

-continued
Compound LXXX
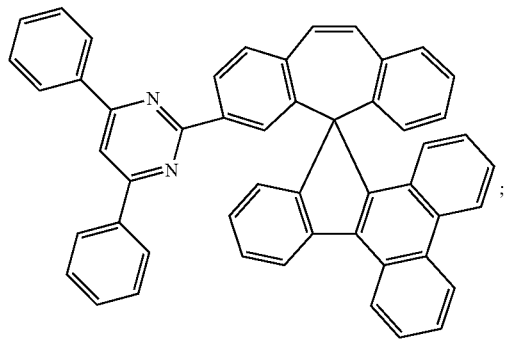
Compound LXXXI
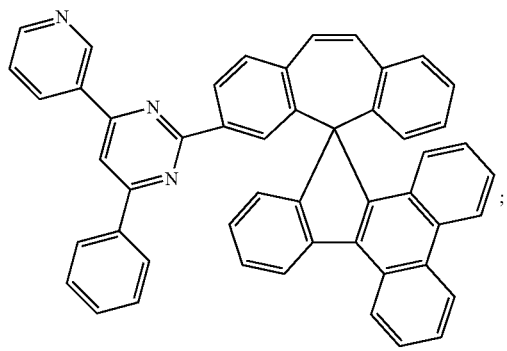
Compound LXXXII
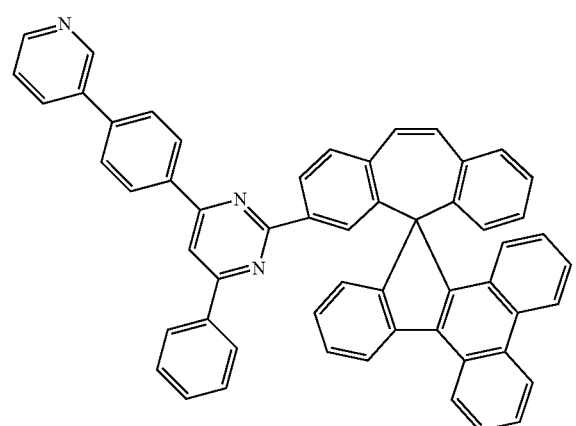
Compound LXXXIII
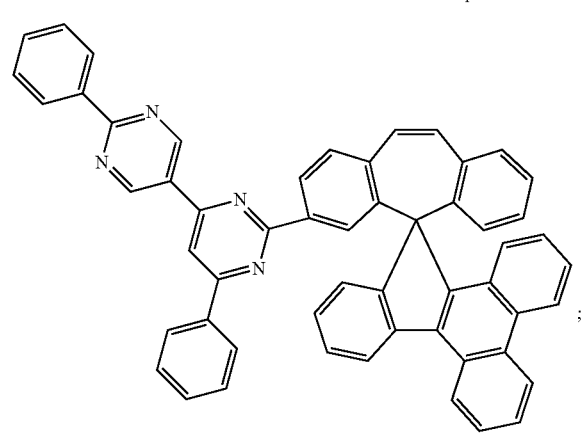
Compound LXXXIV
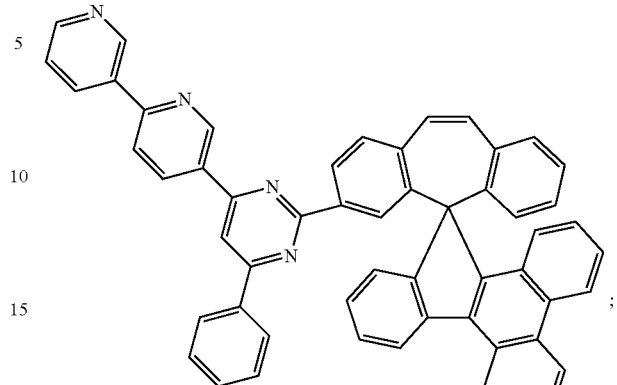
Compound LXXXV
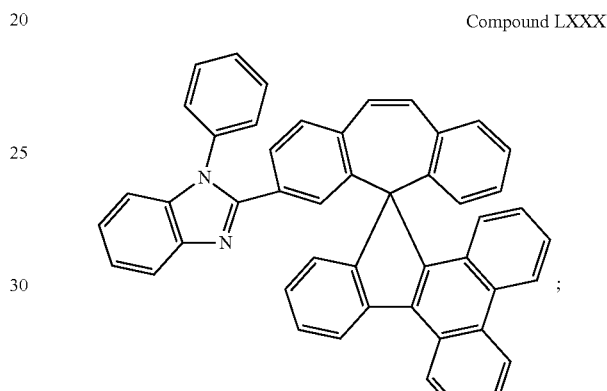
Compound LXXXVI
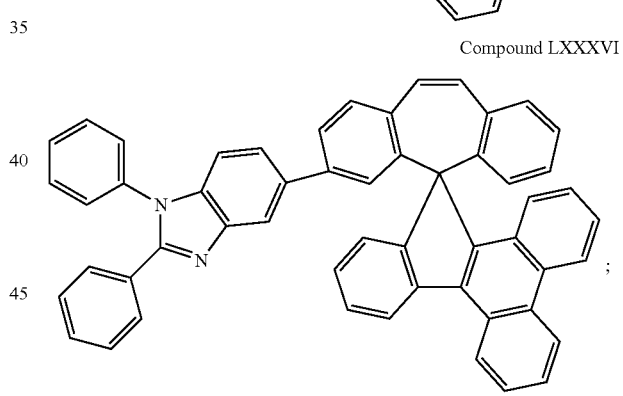
Compound LXXXVII Compound LXXXVIII
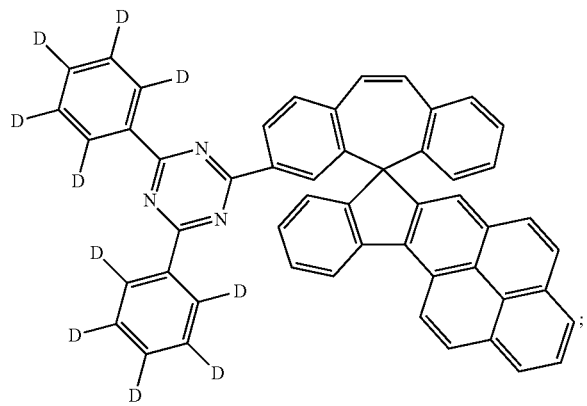
Compound LXXXIX
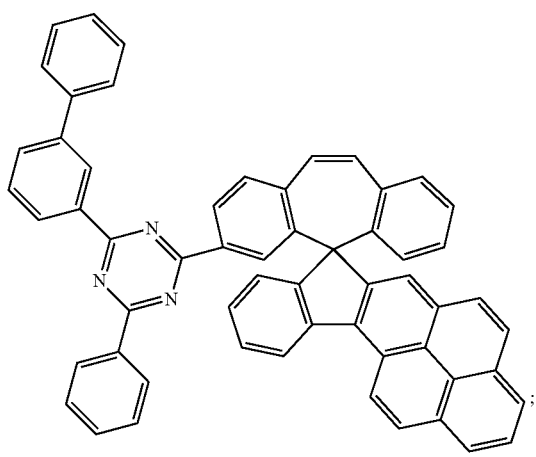
Compound XC
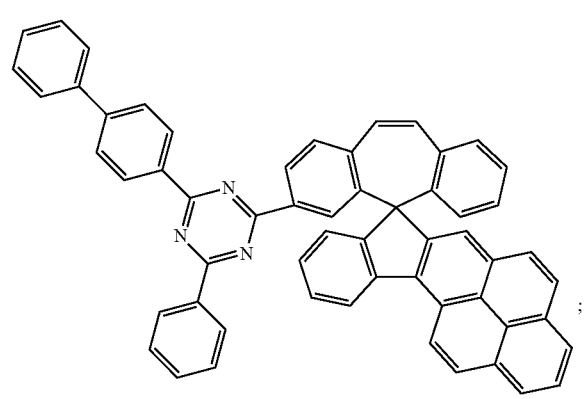
Compound XCI
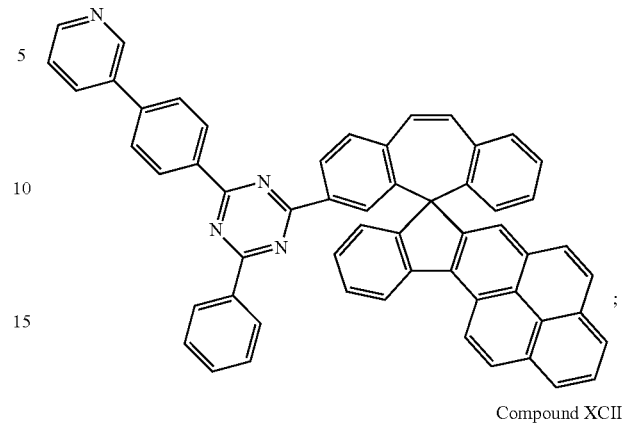
Compound XCII
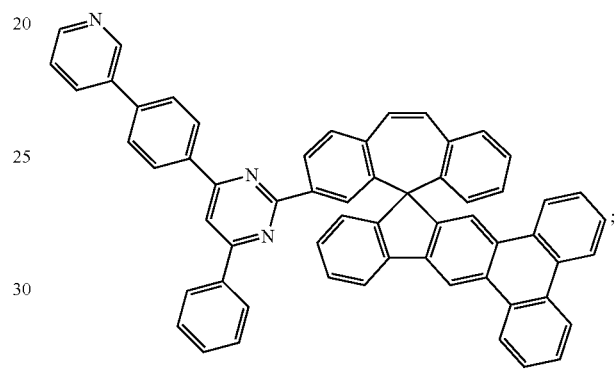
Compound XCIII
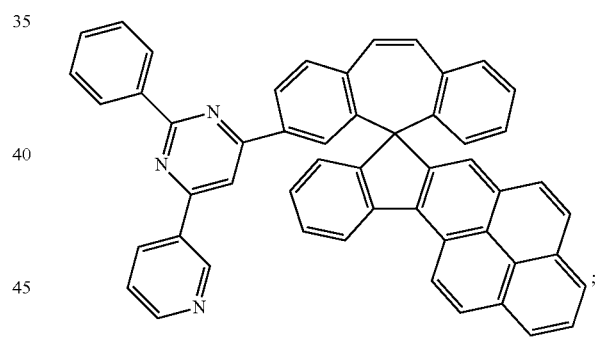
Compound XCIV
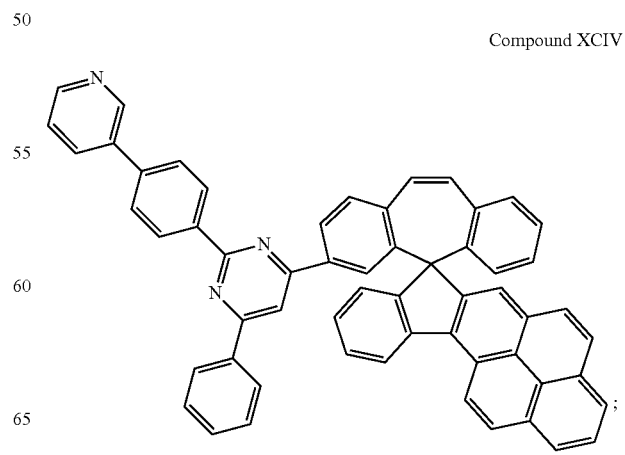

Compound XCV
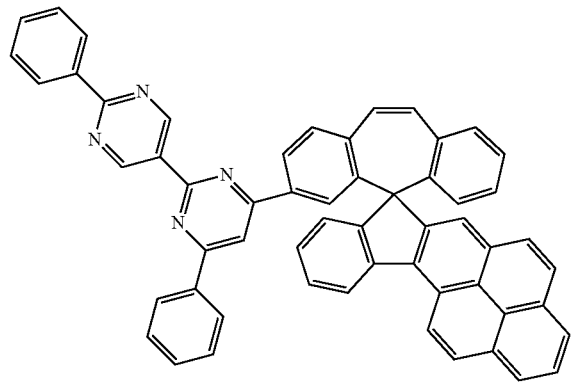
Compound XCVI
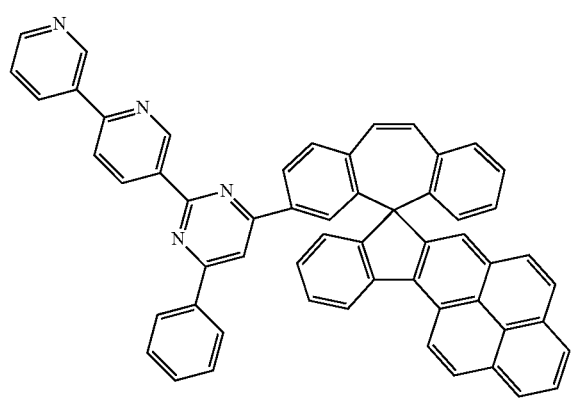
Compound XCVII
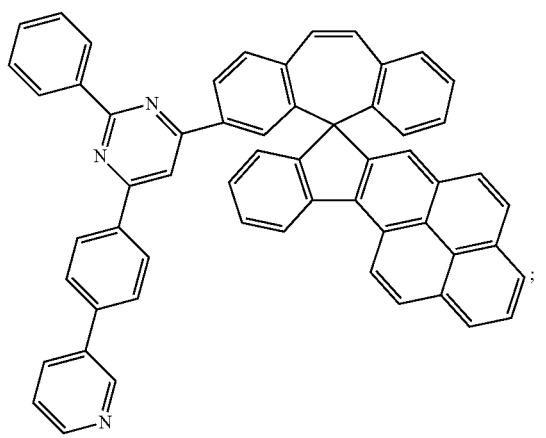
Compound XCVIII
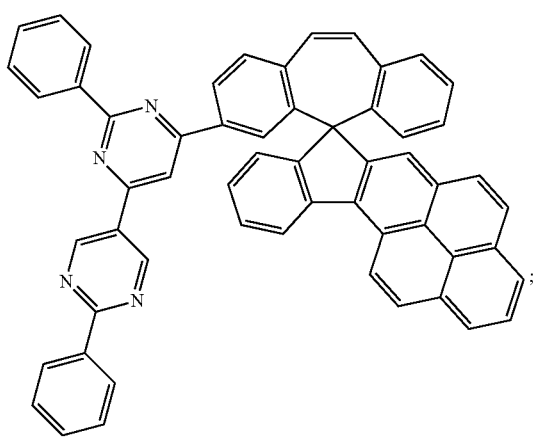
Compound IC
Compound C
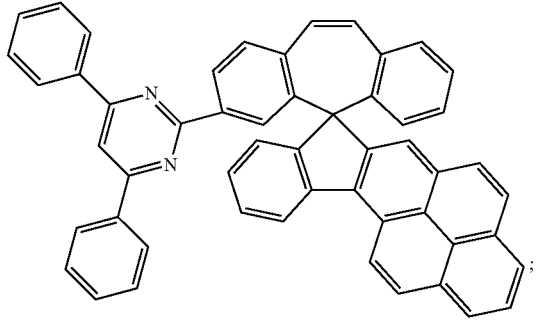
Compound CI Compound CII
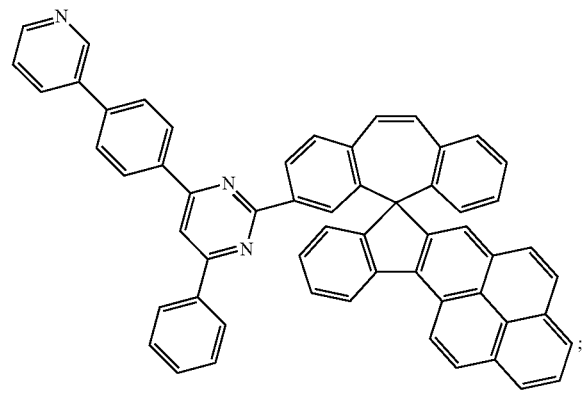
Compound CIII
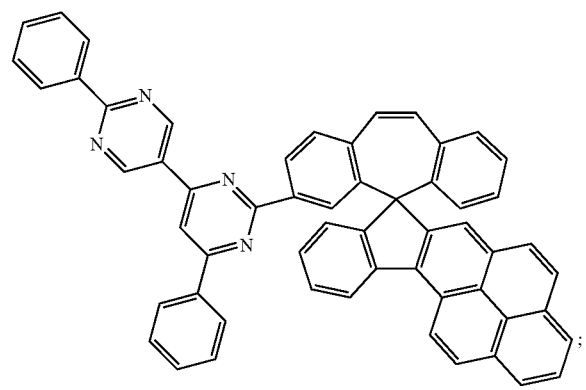
Compound CIV
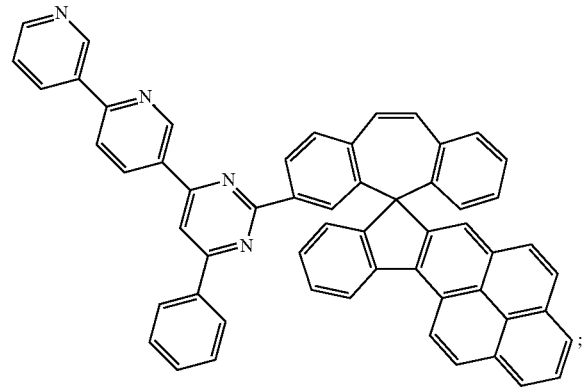
Compound CV
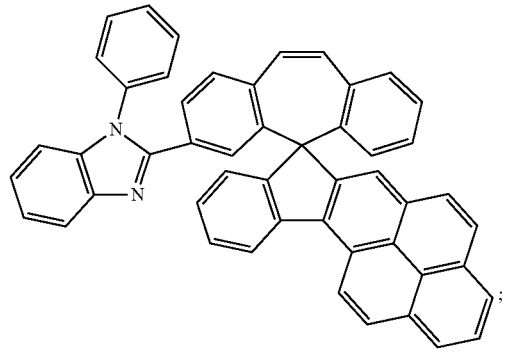
Compound CVI
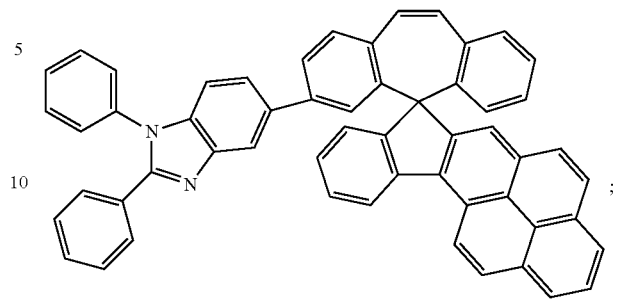
Compound CVII
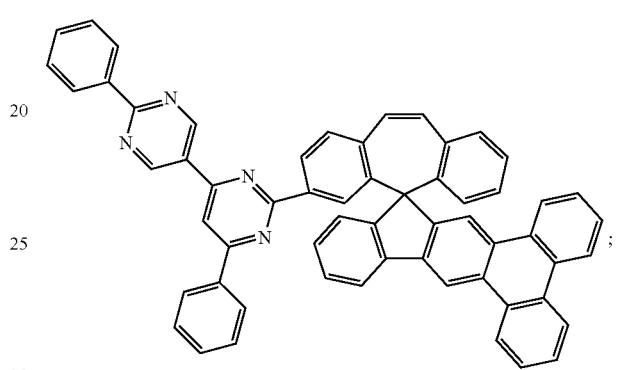
Compound CVIII
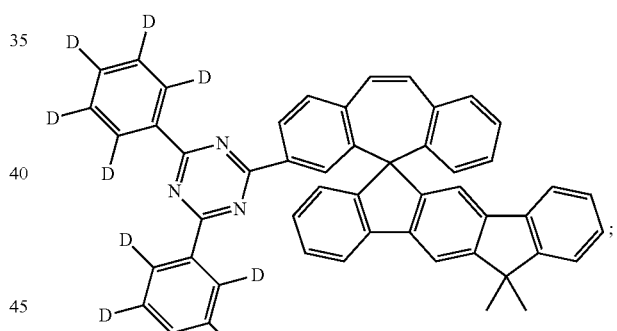
Compound CIX
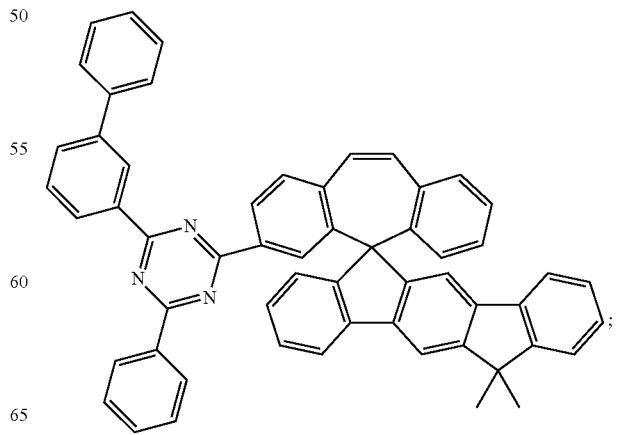

Compound CX
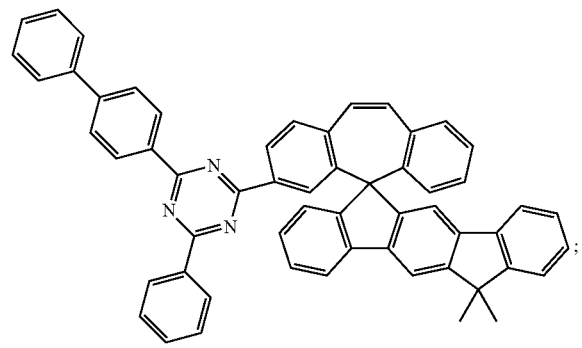
Compound CXIV
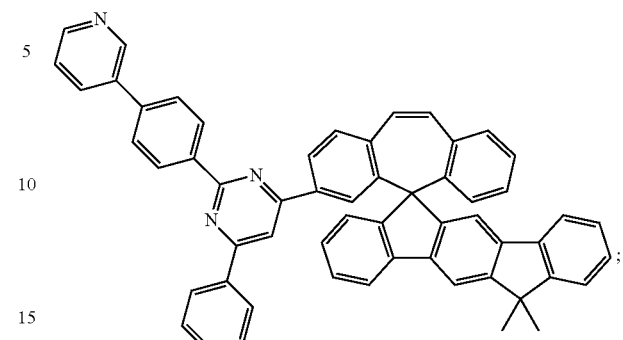
Compound CXI
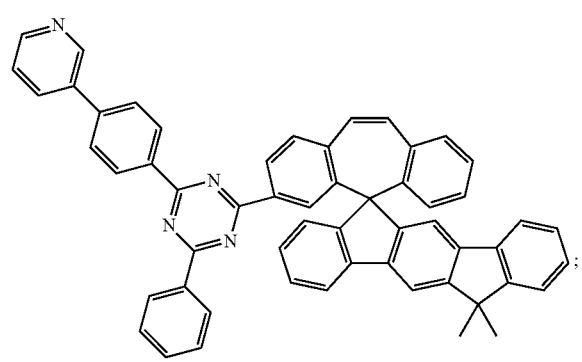
Compound CXV
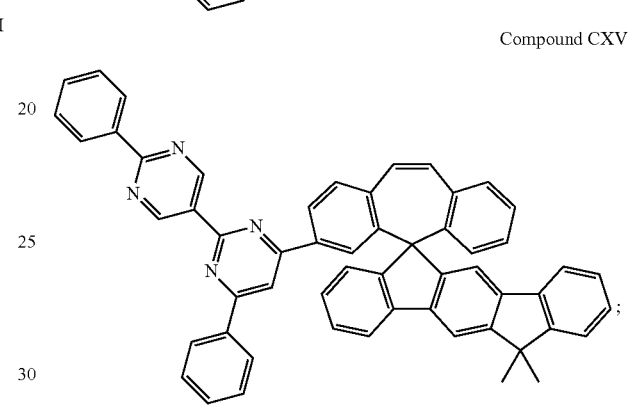
Compound CXII
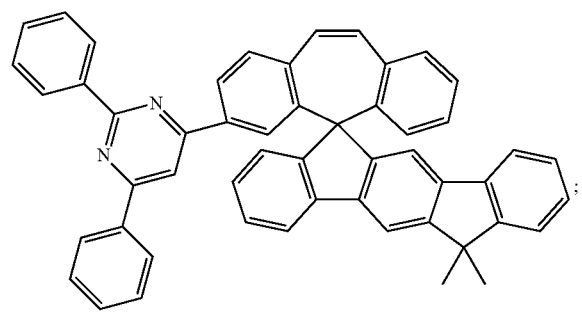
Compound CXVI
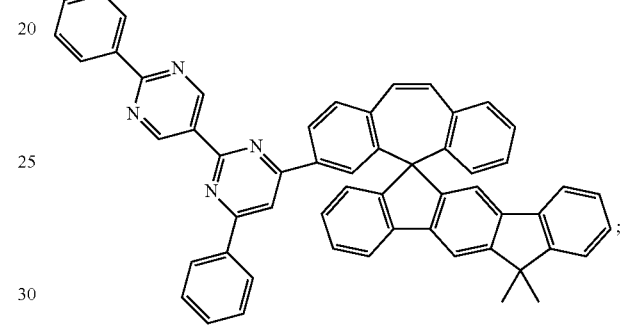
Compound CXIII
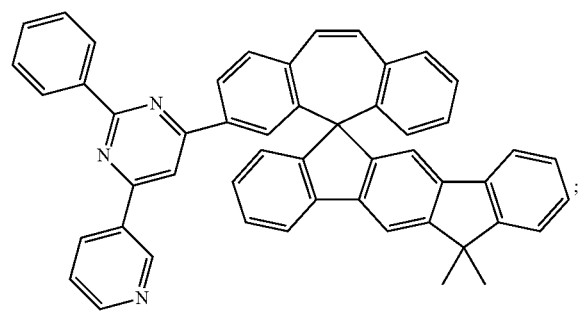
Compound CXVII
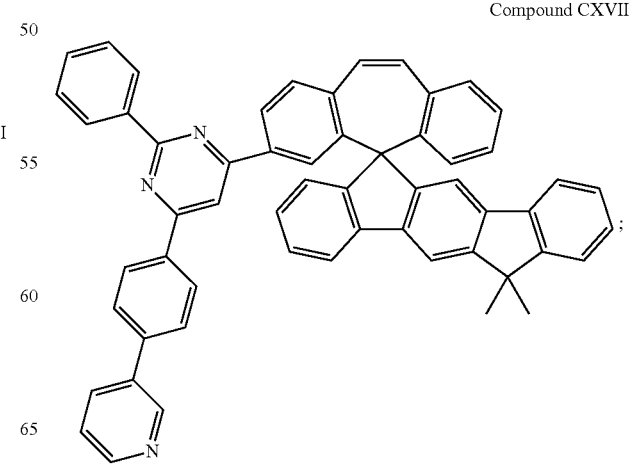

Compound CXVIII
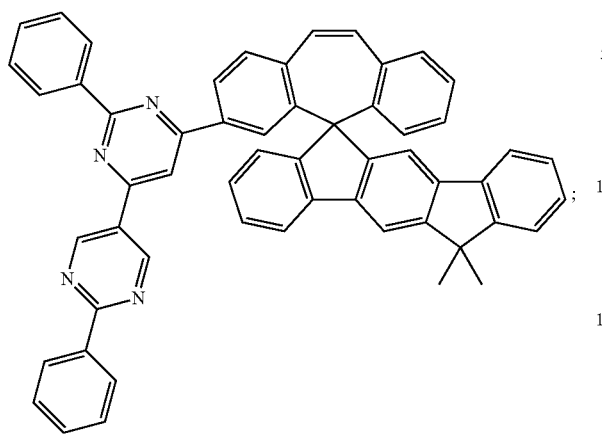
Compound CXIX
Compound CXX
Compound CXXI
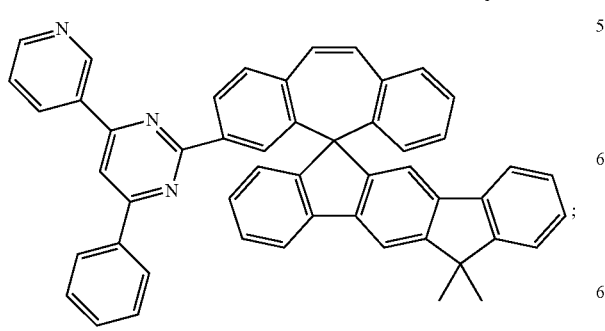
Compound CXXII
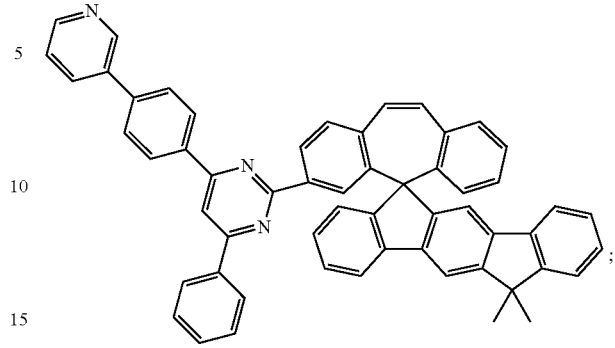
Compound CXXIII
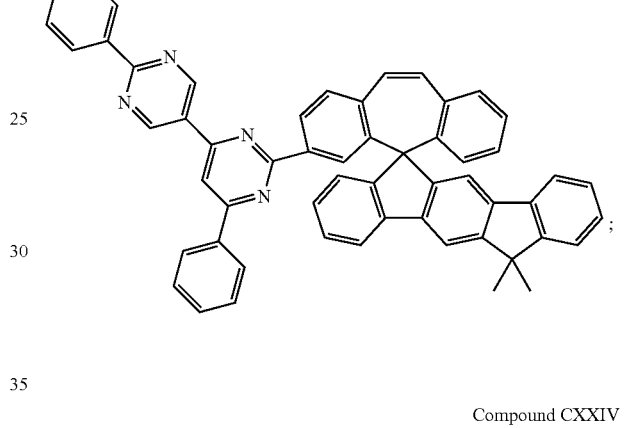
Compound CXXIV
Compound CXXV
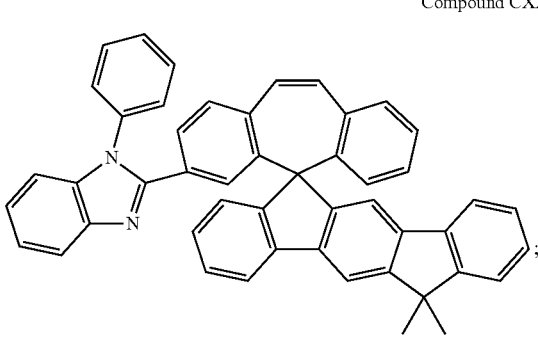

-continued
Compound CXXVI
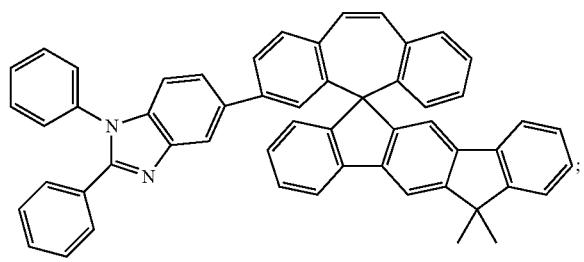
Compound CXXVII
Compound CXXVIII
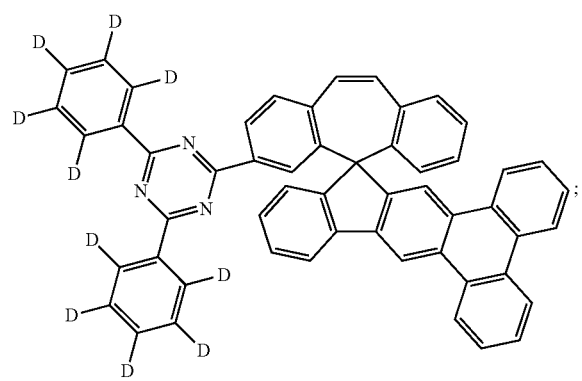
Compound CXXIX
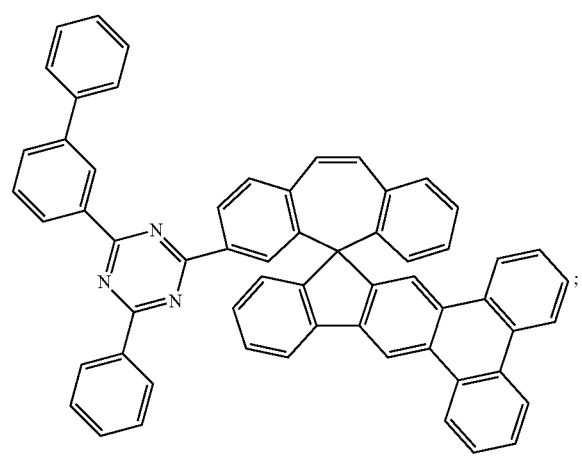
-continued
Compound CXXX
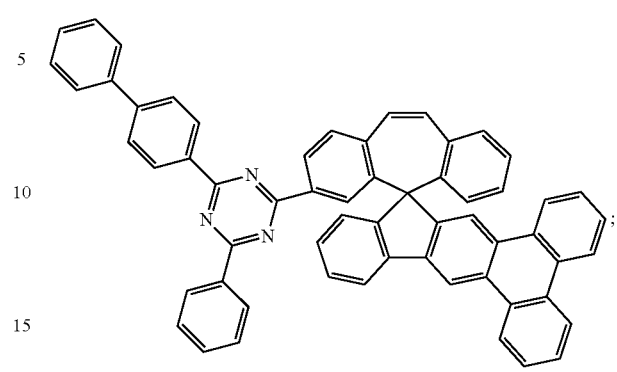
Compound CXXXI
Compound CXXXII
Compound CXXXIII Compound CXXXIV
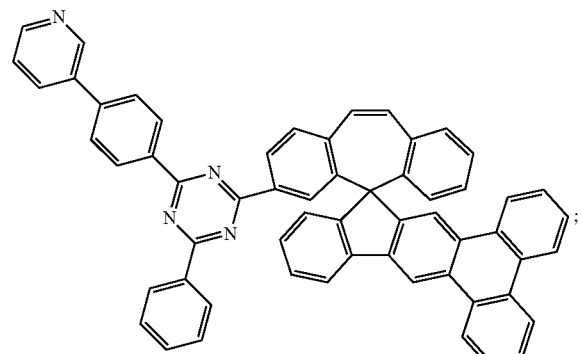
Compound CXXXV
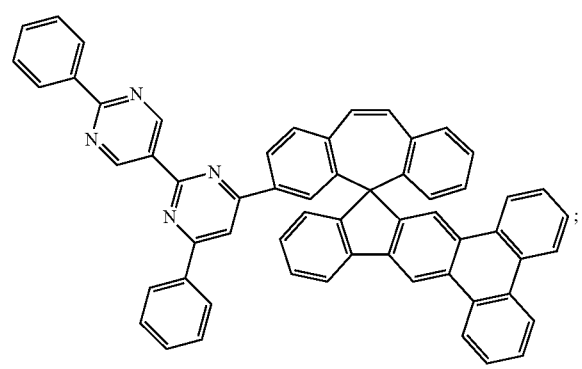
Compound CXXXVI
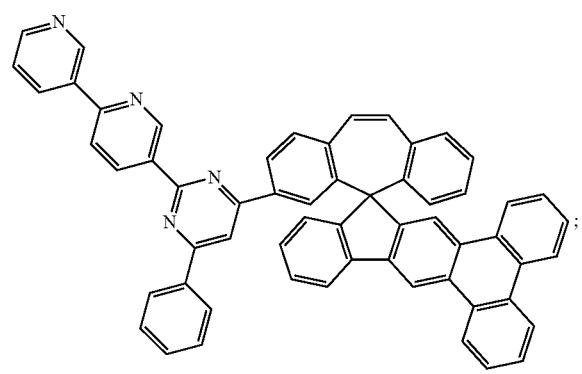
Compound CXXXVII
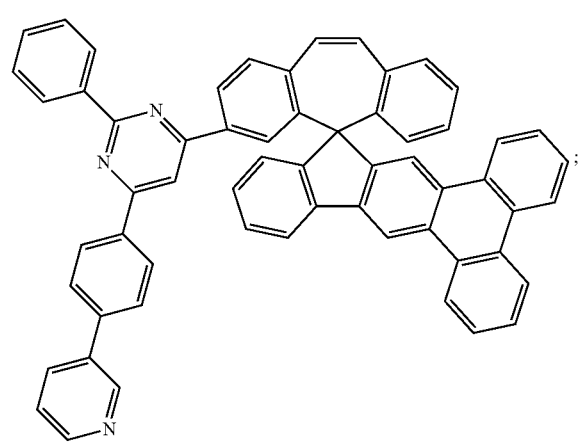
Compound CXXXVIII
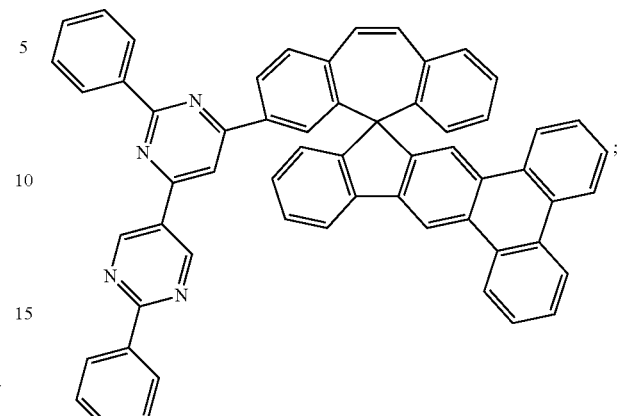
Compound CXXXIX
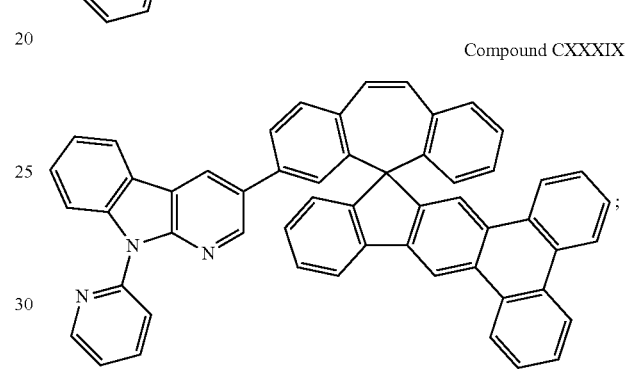
Compound CXL
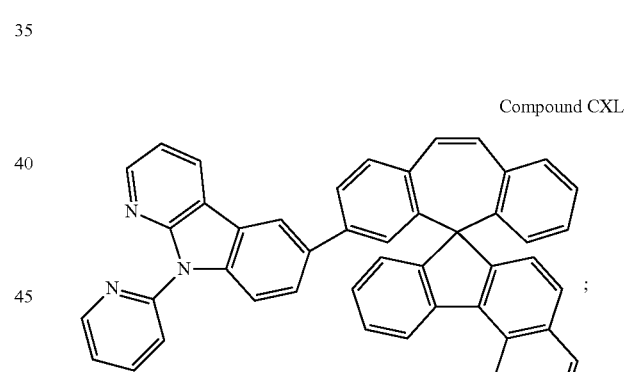
Compound CXLI
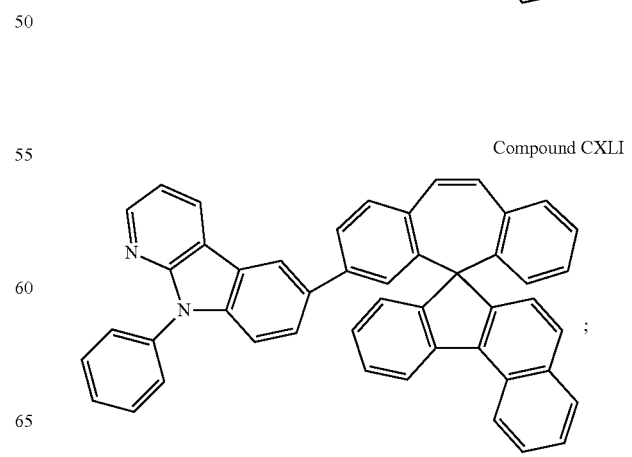

Compound CXLII
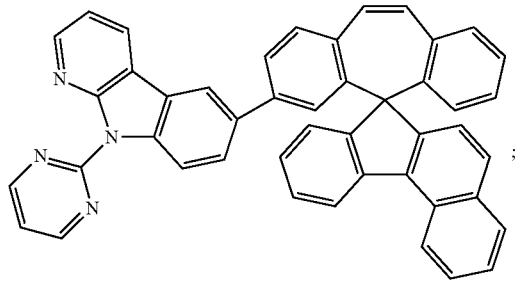
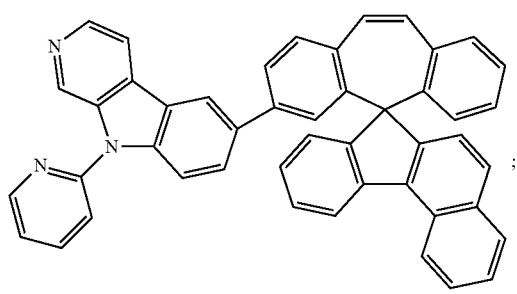
Compound CXLIII
Compound CXLIV
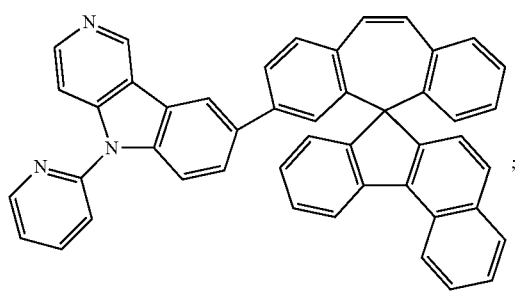
Compound CXLV
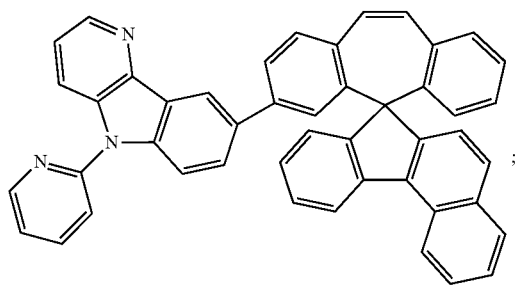
Compound CXLVI
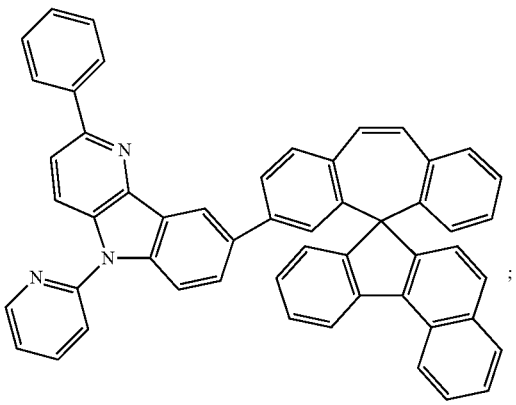
Compound CXLVII
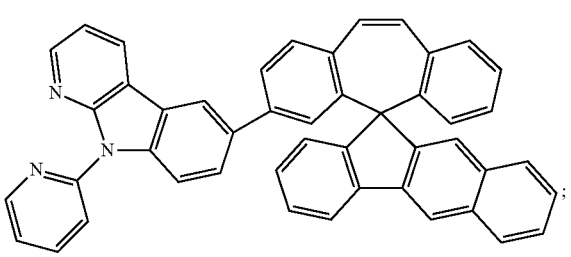
Compound CXLVIII
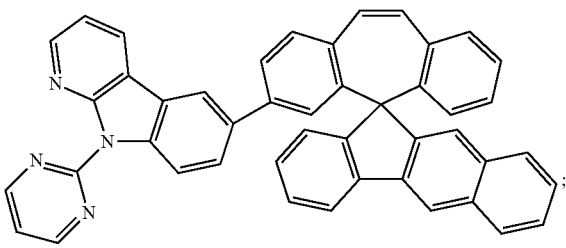
Compound CIL
Compound CL
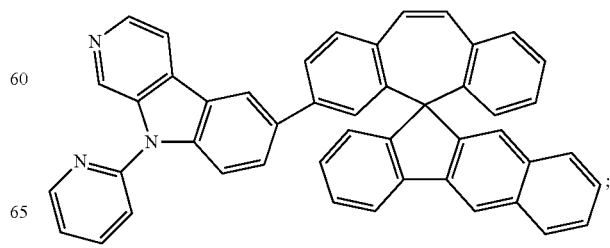

Compound CLI
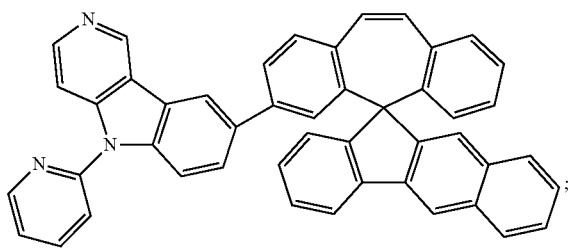
Compound CLII
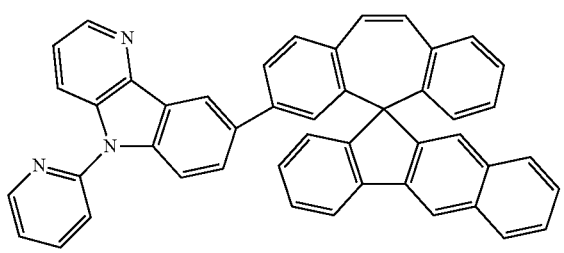
Compound CLIII
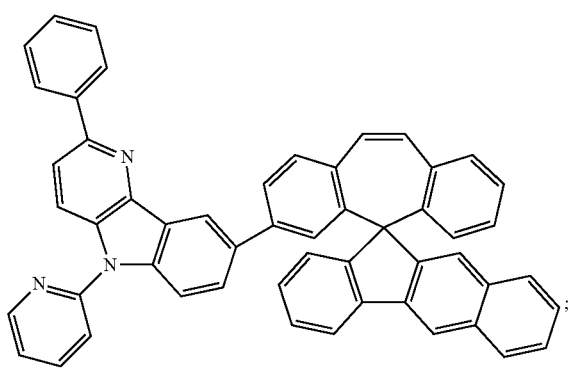
Compound CLIV
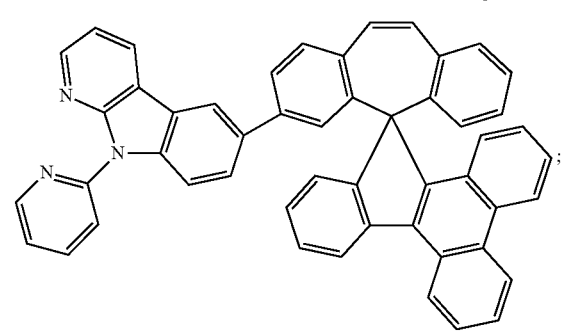
Compound CLV
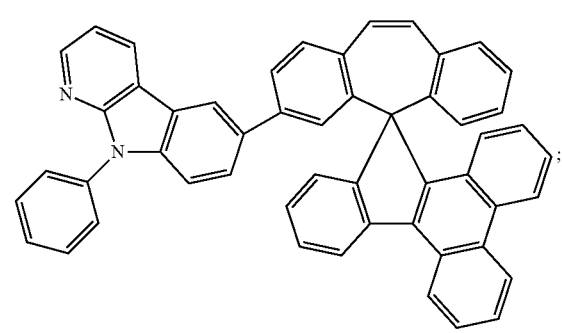
Compound CLVI
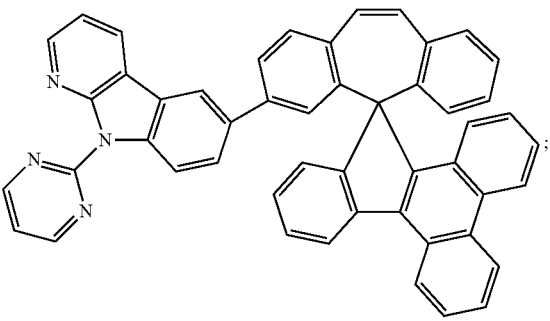
Compound CLII
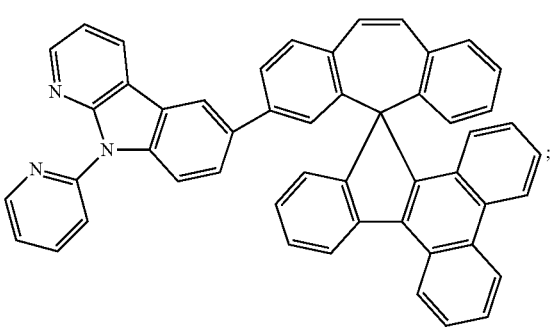
Compound CLVIII
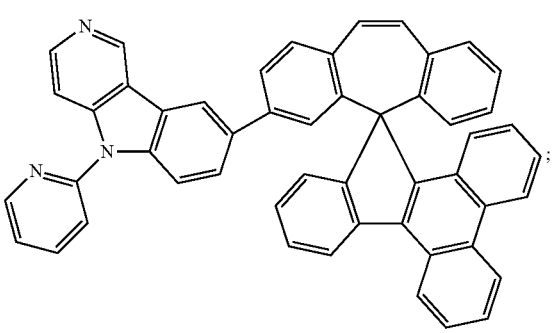
Compound CLIX
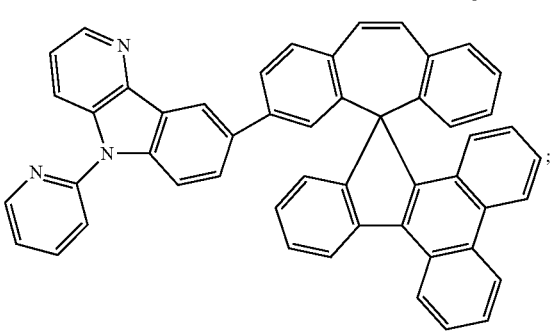

-continued
Compound CLX
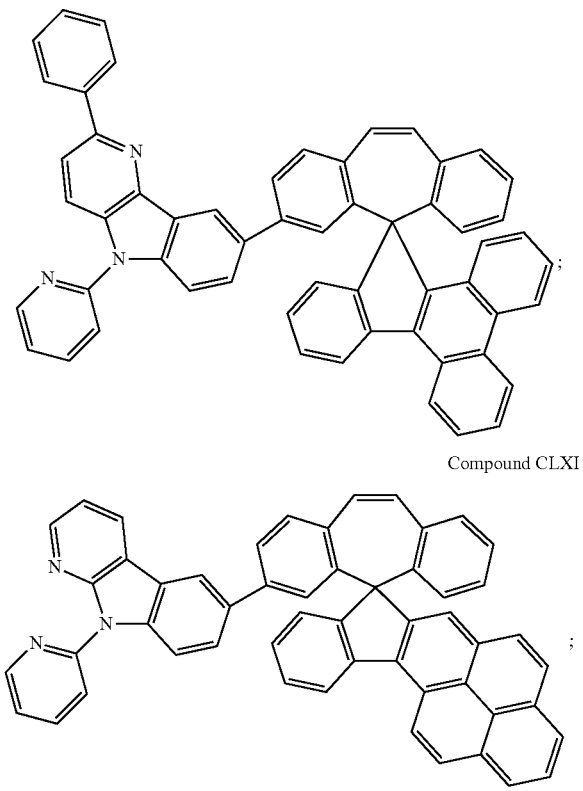
Compound CLXI
Compound CLXII
Compound CLXIII
-continued
Compound CLXIV
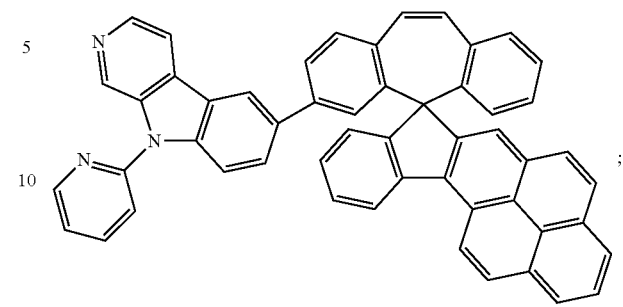
Compound CLXV
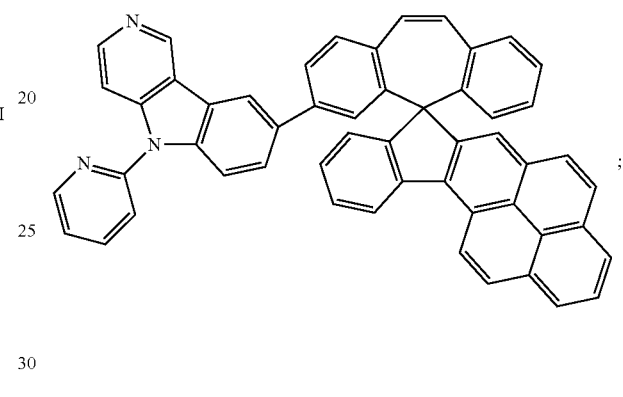
Compound CLXVI
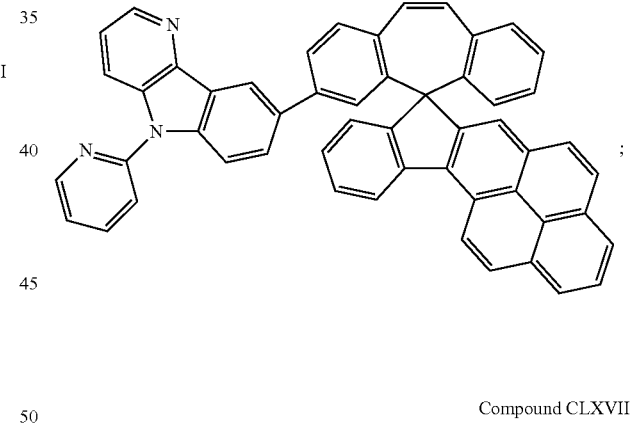
Compound CLXVII
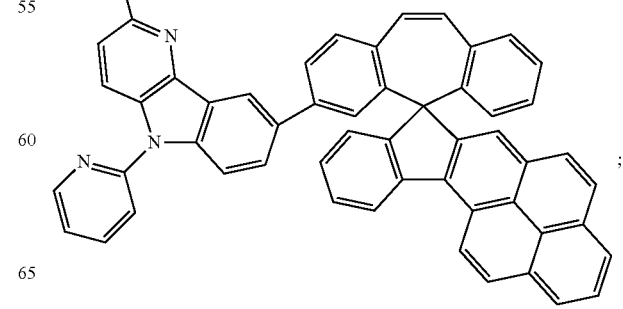

Compound CLXVIII
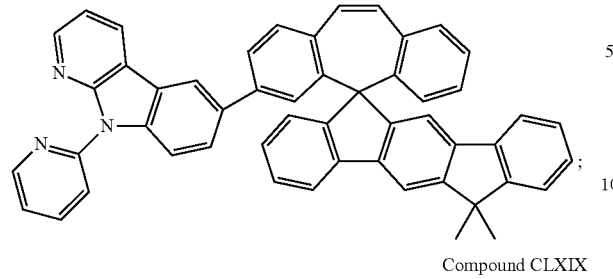
Compound CLXIX
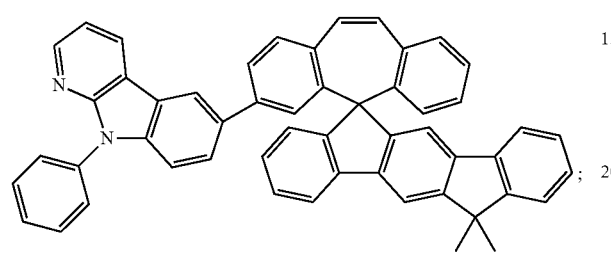
Compound CLXX
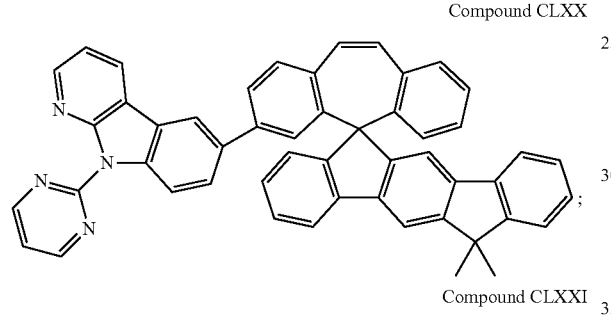
Compound CLXXI
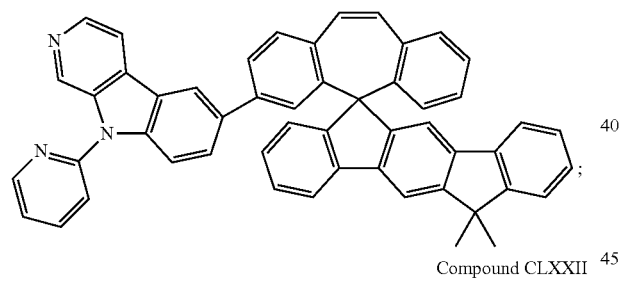
Compound CLXXII
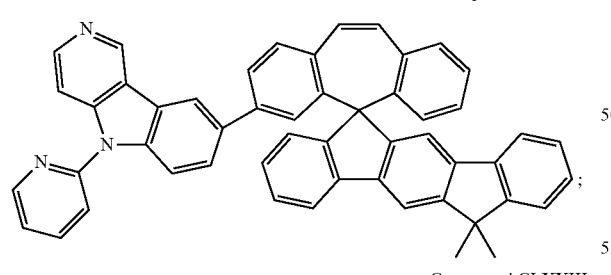
Compound CLXXIII
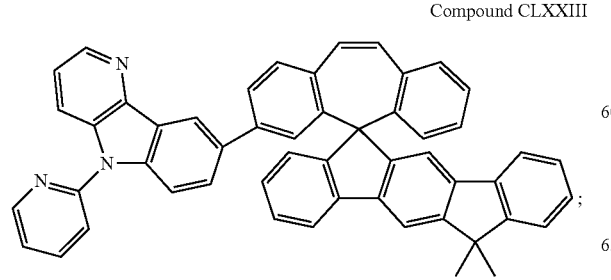
Compound CLXXIV
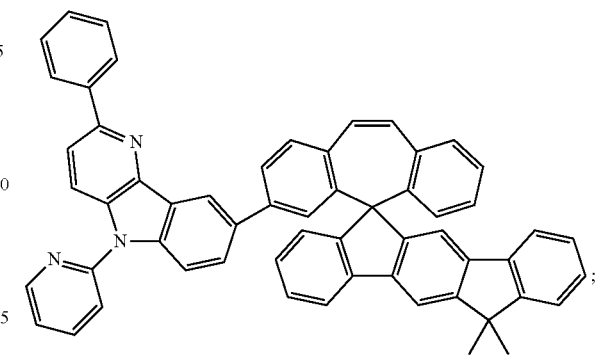
Compound CLXXV
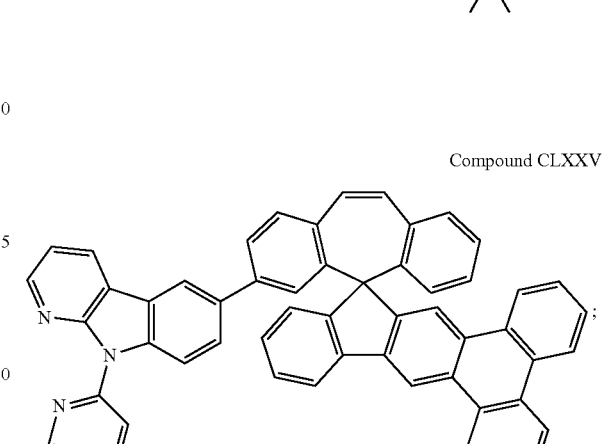
Compound CLXXVI
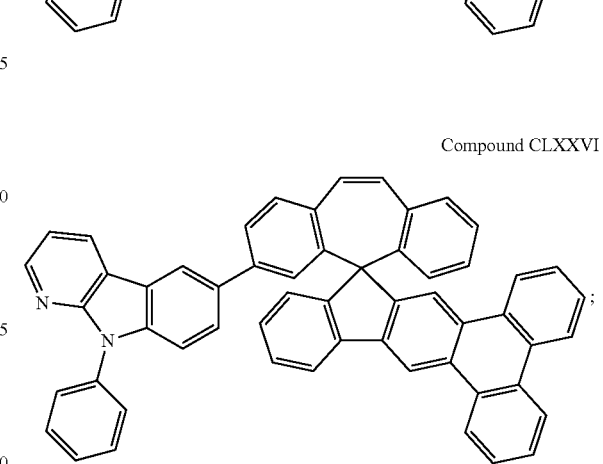
Compound CLXXVII
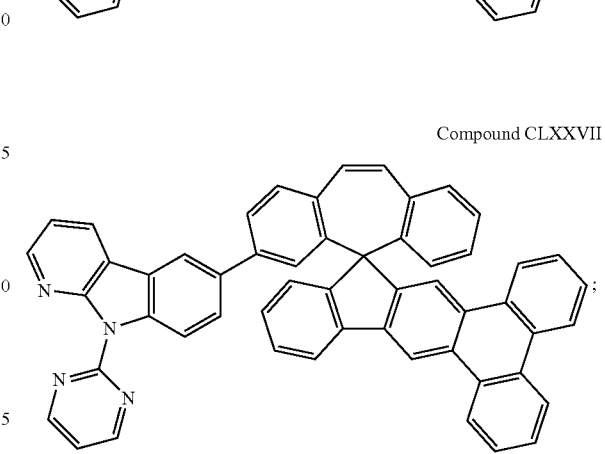

Compound CLXXVIII

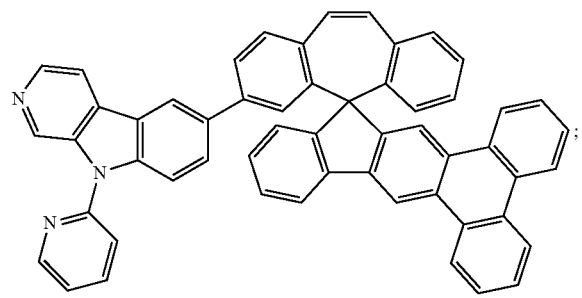

Compound CLXXIX

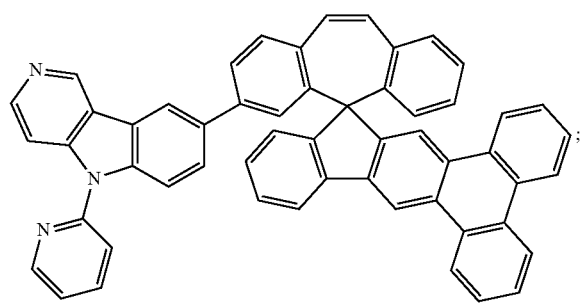

Compound CLXXX

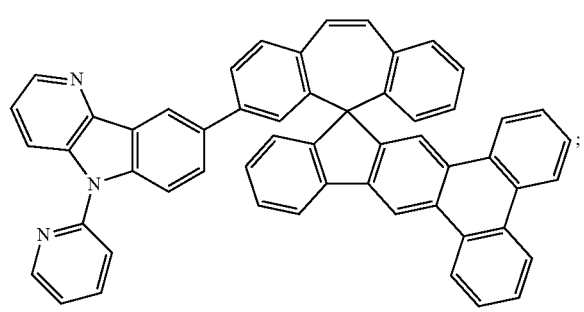

Compound CLXXXI

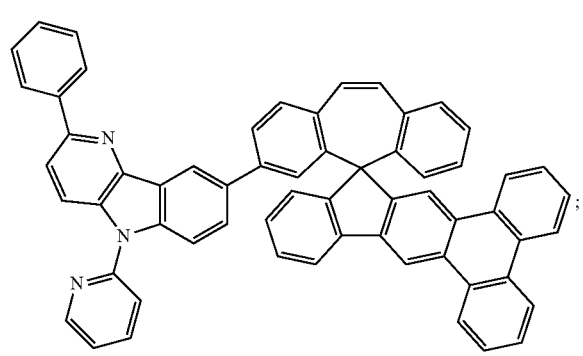

Compound CLXXXII

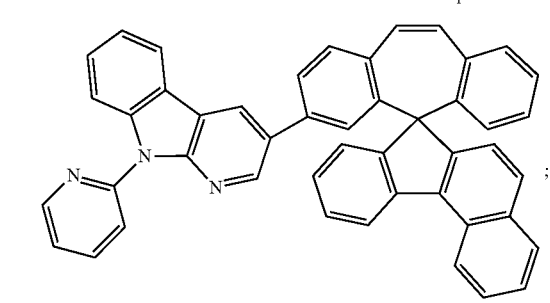

Compound CLXXXIII

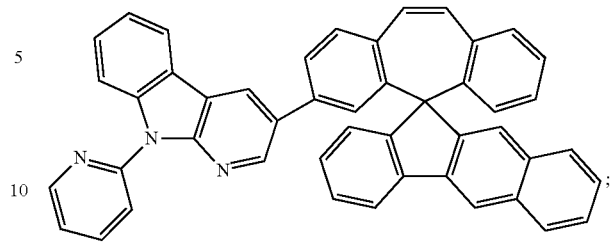

Compound CLXXXIV

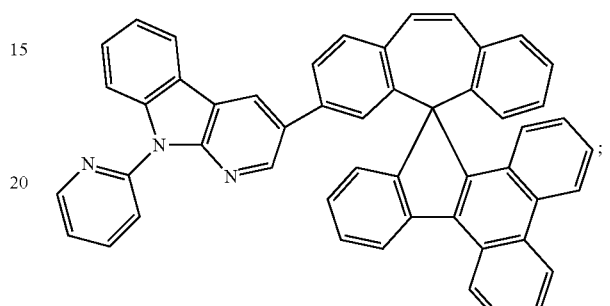

Compound CLXXXV

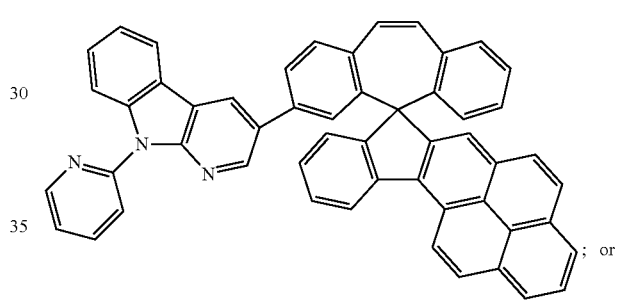

; or

Compound CLXXXVI

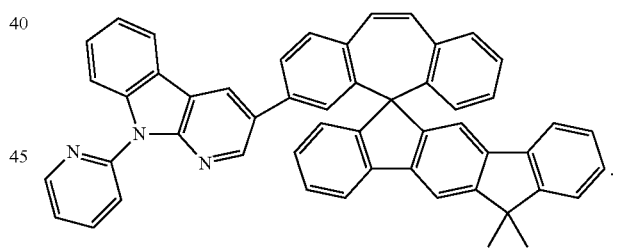

.

The present invention also provides an organic electronic device, comprising a first electrode, a second electrode, and an organic layer disposed between the first electrode and the second electrode. The organic layer comprises the novel compound as described above.

Preferably, the organic electronic device is an organic light emitting device (OLED). More preferably, the novel compound of the present invention may be used as an electron transport material or a hole blocking layer.

Specifically, the organic light emitting device may comprise:
a hole injection layer formed on the first electrode;
a hole transport layer formed on the hole injection layer;
an emission layer formed on the hole transport layer;
an electron transport layer formed on the emission layer;
an electron injection layer formed between the electron transport layer and the second electrode.

In one embodiment, the organic layer may be the electron transport layer, i.e., the electron transport layer comprises the novel compound as stated above.

Preferably, the hole injection layer may be a two-layered structure, i.e., the OLED comprises a first hole injection layer and a second hole injection layer disposed between the first electrode and the hole transport layer.

Preferably, the hole transport layer may be a two-layered structure, i.e., the OLED comprises a first hole transport layer and a second hole transport layer disposed between the two-layered hole injection layer and the emission layer.

Preferably, the electron transport layer is made of the novel compound such as Compounds I to CLXXXVI. The OLEDs using the novel compound as the electron transport material can have an improved efficiency compared to commercial OLEDs using known electron transport material, such as 2-(4-(9,10-di(naphthalen-2-yl)anthracen-2-yl)phenyl)-1-phenyl-1H-benzo[d]im idazole; bis(2-methyl-8-quinolinolato)(p-phenyl phenolato) aluminum; and 2-(4-biphenylyl)-5-(4-tert-butylphenyl)-1,3,4-oxadiazole (PBD), as the electron transport material.

Preferably, the OLED comprises a hole blocking layer formed between the electron transport layer and the emission layer, to block holes overflow from the emission layer to the electron transport layer. Said hole blocking layer may be made of the foresaid novel compound, 2,9-dimethyl-4,7-diphenyl-1,10-phenanthroline (BCP) or 2,3,5,6-tetramethyl-phenyl-1,4-(bis-phthalimide) (TMPP), but not limited thereto. In another embodiment, the organic layer may be the hole blocking layer, i.e., the hole blocking layer comprises the novel compound as stated above.

Preferably, the OLED comprises an electron blocking layer formed between the hole transport layer and the emission layer, to block electrons overflow from the emission layer to the hole transport layer. Said electron blocking layer may be made of 9,9'-[1,1'-biphenyl]-4,4'-diylbis-9H-carbazole (CBP) or 4,4',4''-tri(N-carbazolyl)-triphenylamine (TCTA), but not limited thereto.

In the presence of such a hole blocking layer and/or a electron blocking layer in an OLED, the OLED has a higher luminous efficiency compared to a typical OLED.

Said first and second hole transport layers may be made of, for example, but not limited to: $N^1,N^{1'}$-(biphenyl-4,4'-diyl)bis($N^1$-(naphthalen-1-yl)-$N^4,N^{4'}$-diphenylbenzene-1,4-diamine); or $N^4,N^{4'}$-di(naphthalen-1-yl)-$N^4,N^{4'}$-diphenylbiphenyl-4,4'-diamine (NPB).

Said first and second hole injection layers may be made of, for example, but not limited to, polyaniline or polyethylenedioxythiophene.

Said emission layer can be made of an emission material including a host and a dopant. The host of the emission material is, for example, but not limited to, 9-(4-(naphthalen-1-yl)phenyl)-10-(naphthalen-2-yl) anthracene.

For red OLEDs, the dopant of the emission material is, for example, but not limited to: organometallic compounds of iridium (II) having perylene ligands, fluoranthene ligands or periflanthene ligands. For green OLEDs, the dopant of the emission material is, for example, but not limited to: diaminofluorenes; diaminoanthracenes; or organometallic compounds of iridium (II) having phenylpyridine ligands. For blue OLEDs, the dopant of the emission material is, for example, but not limited to: diaminofluorenes; diaminoanthracenes; diaminopyrenes; or organicmetallic compounds of iridium (II) having phenylpyridine ligands. With various host materials of the emission layer, the OLED can emit lights in red, green or blue.

Said electron injection layer may be made of an electron injection material, for example, but not limited to (8-oxidonaphthalen-1-yl)lithium (II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
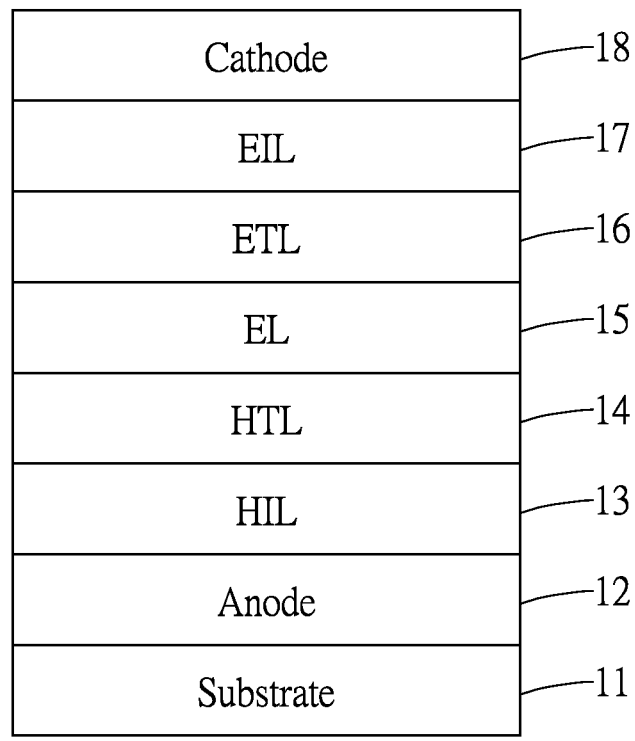
FIG. 1 illustrates a schematic cross-sectional view of an OLED.

Hereinafter, one skilled in the arts can easily realize the advantages and effects of a novel compound and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Synthesis of Intermediate A1

Intermediate A1 used for preparing a novel compound was synthesized by the following steps. The synthesis pathway of the Intermediate A1 was summarized in Scheme A1.

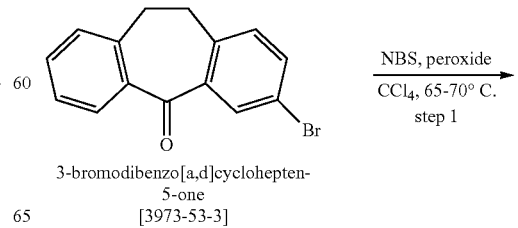

Scheme A1

3-bromodibenzo[a,d]cyclohepten-5-one
[3973-53-3]

NBS, peroxide
CCl$_4$, 65-70° C.
step 1

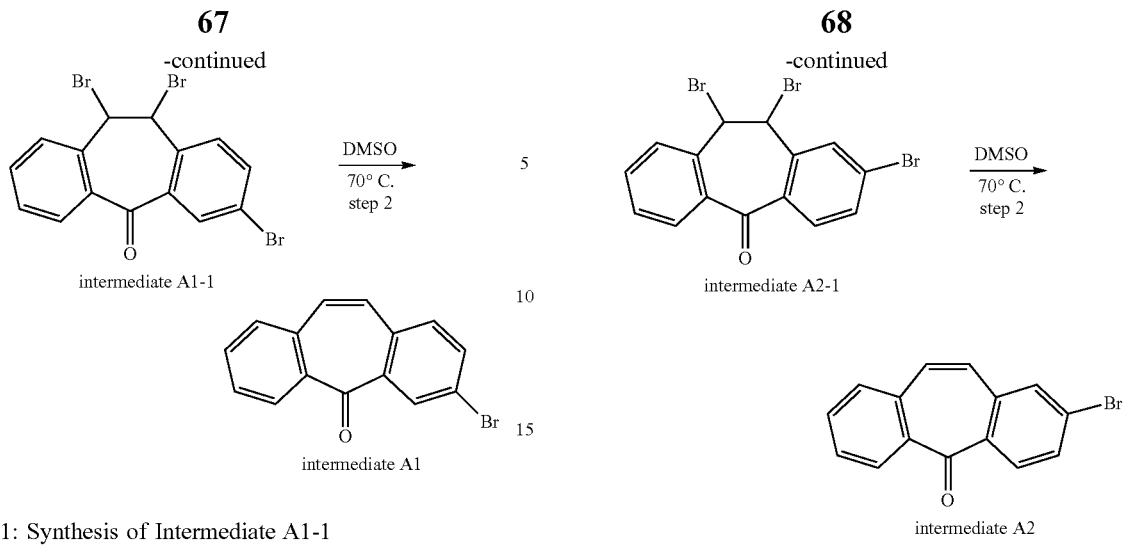

Step 1: Synthesis of Intermediate A1-1

A mixture of 3-bromodibenzo[a,d]cyclohepten-5-one (1.0 eq), N-bromosuccinimide (2.0 eq), and benzyl peroxide (0.01 eq) in carbon tetrachloride (5 times of starting material) was heated to about 65° C. to 70° C. The reaction progress was monitored by high performance liquid chromatography (HPLC). After completion of the reaction, the precipitate was separated by filtration and washed with CH$_3$OH, then purified by recrystallization. The purified product was concentrated to dryness, whereby a white solid product was obtained in 92.3% yield. FD-MS analysis C$_{15}$H$_9$Br$_3$O: theoretical value 444.94, observed value 444.94.

Step 2: Synthesis of Intermediate A1

The obtained intermediate A1-1 (1.0 eq) in DMSO, (w/v=⅓ to the reactant) was heated to 70° C. The reaction was monitored by HPLC. After completion of the reaction, the reaction mixture was quenched with ice water. The precipitate was separated by filtration and then purified by column chromatography on silica gel. Intermediate A1 was obtained as pale yellow solid in 93% yield.

The pale yellow solid product was identified as Intermediate A1 by FD-MS analysis. FD-MS analysis C$_{15}$H$_9$BrO: theoretical value of 285.14 and observed value of 285.14.

Synthesis of Intermediate A2

Intermediate A2 used for preparing a novel compound was synthesized in a similar manner as Intermediate A1 through steps 1 and 2, except that the starting material 3-bromodibenzo[a,d]cyclohepten-5-one was replaced by 2-bromodibenzo[a,d]cyclohepten-5-one (CAS No. 198707-82-3). The synthesis pathway of Intermediate A2 was summarized in Scheme A2. All intermediates were analyzed according to the methods as described above, and the results were listed in Table 1.

Scheme A2

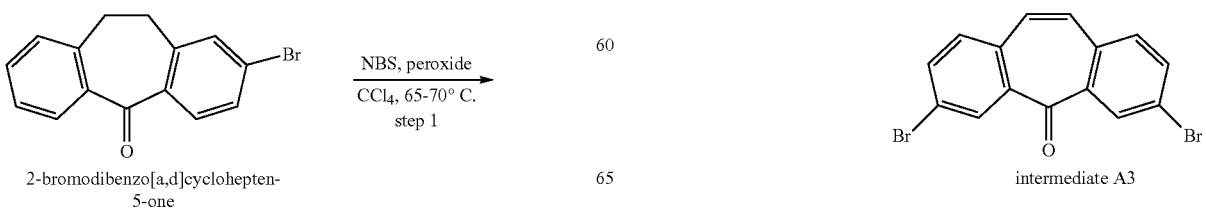

2-bromodibenzo[a,d]cyclohepten-5-one

Synthesis of Intermediate A3

Intermediate A3 used for preparing a novel compound was synthesized in a similar manner as Intermediate A1 through steps 1 and 2, except that the starting material 3-bromodibenzo[a,d]cyclohepten-5-one was replaced by 3,7-dibromodibenzo[a,d]cyclohepten-5-one (CAS No. 226946-20-9). The synthesis pathway of Intermediate A3 was summarized in Scheme A3. All intermediates were analyzed as described above, and the results were listed in Table 1.

Scheme A3

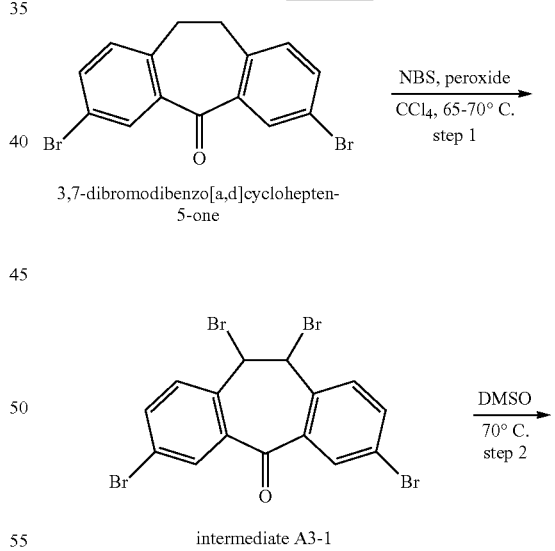

TABLE 1 chemical structures, yields, formulae, and mass (M⁺) analyzed by FD-MS of intermediates.

| Intermediate | A1-1 | A1 |
|---|---|---|
| Chemical Structure | | |
| Yield | 92.3% | 93% |
| Formula | $C_{15}H_9Br_3O$ | $C_{15}H_9BrO$ |
| Mass(M⁺) | 444.94 | 285.14 |
| Intermediate | A2-1 | A2 |
| Chemical Structure | | |
| Yield | 91.5% | 87% |
| Formula | $C_{15}H_9Br_3O$ | $C_{15}H_9BrO$ |
| Mass(M⁺) | 444.94 | 285.14 |
| Intermediate | A3-1 | A3 |
| Chemical Structure | | |
| Yield | 93.7% | 90% |
| Formula | $C_{15}H_8Br_4O$ | $C_{15}H_8Br_2O$ |
| Mass(M⁺) | 523.84 | 364.03 |

Modifications of Intermediates A1 to A3

In addition to the Intermediates A1 to A3, one person skilled in the art can adopt other starting materials and successfully synthesize other desired intermediates through a reaction mechanism similar to Scheme A1 to A3. Applicable modifications of Intermediates A1 to A3 may be, for example, but not limited to, Intermediates A4 to A15 as follows.

Intermediate A4

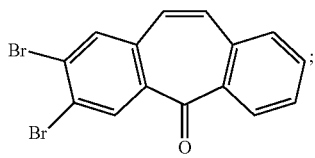

Intermediate A5

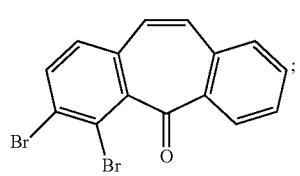

Intermediate A6

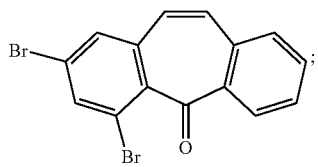

Intermediate A7

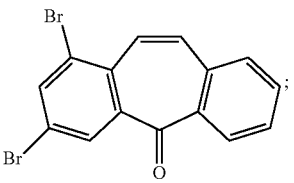

Intermediate A8

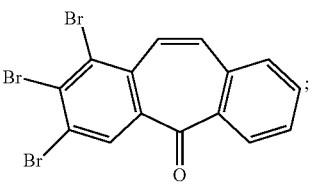

-continued

Intermediate A9

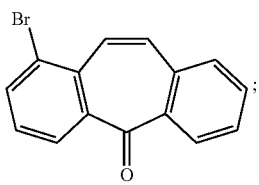

Intermediate A10

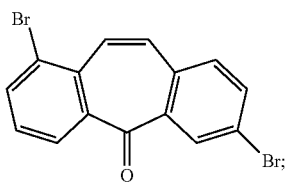

Intermediate A14

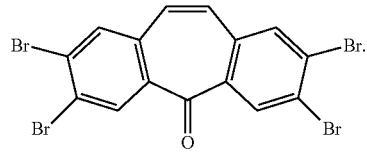

Intermediate A15

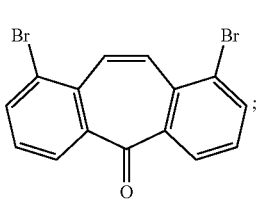

Intermediate A11

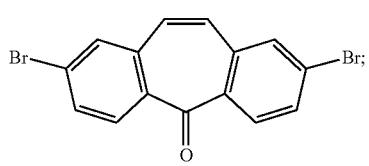

Synthesis of Intermediates B1 and B3 to B6

Intermediates B1 and B3 to B6 were synthesized by reacting 1-bromo-2-iodobenzene and aryl boronic acid (Reactant An). A general synthesis pathway for Intermediate Bn was summarized in Scheme B-1. In the following Scheme B-1, "Reactant An" may be any one of Reactants A1 to A5 as listed in Table 2, and "Intermediate Bn" may be any one of foresaid Intermediates B1 and B3 to B6.

Scheme B-1

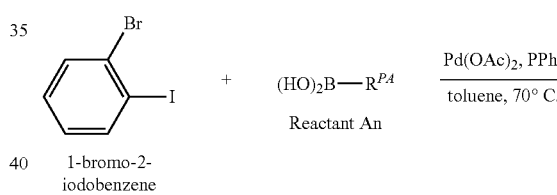

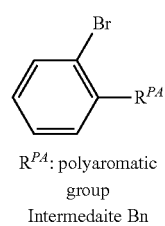

$R^{PA}$: polyaromatic group
Intermedaite Bn

Intermediate A12

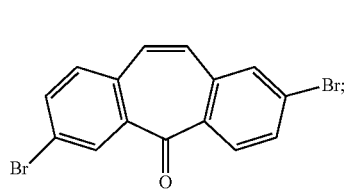

According to the Scheme B-1, each of Intermediates B1 and B3 to B6 was synthesized by the steps as follows.

1-bromo-2-iodobenzene (1.0 eq), Reactant An (1.2 eq), potassium carbonate (3.0 eq), 200 ml of toluene, $PPh_3$ (0.06 eq) and $Pd(OAc)_2$ (0.015 eq) were mixed and stirred at 70° C. After the completion of the reaction, the reaction mixture was then cooled to 25° C., and an organic layer was extracted with a saturated aqueous solution of sodium chloride and EA and dried over magnesium sulfate, followed by filtered with silica gel. After a solid prepared by concentrating the filtrate under a reduced pressure was suspended in hexane, the suspension was filtered again and washed with hexane to obtain Intermediate Bn. All intermediates were analyzed by FD-MS analysis, and the results were listed in Table 2.

Intermediate A13

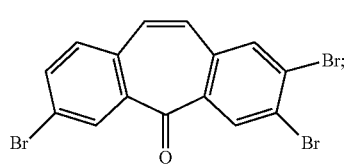

TABLE 2

Reactant An used for preparing Intermediates B1 and B3 to B6, and the chemical structures, yields, formulae, and mass analyzed by FD-MS of Intermediates B1 and B3 to B6.

| Reactant An | Intermediate Bn | | |
|---|---|---|---|
| Chemical Structure | Chemical Structure | Yield (%) | Formula/ Mass (M⁺) |
| 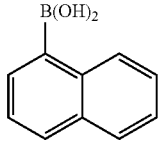<br>Reactant A1 | 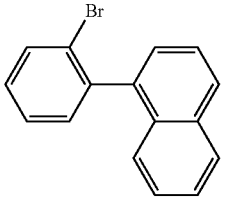<br>Intermediate B1 | 81 | C₁₆H₁₁Br/ 283.16 |
| 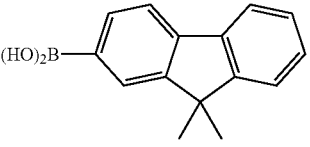<br>Reactant A2 | 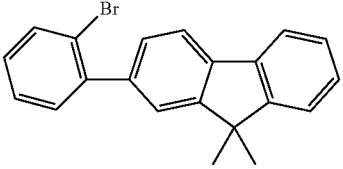<br>Intermediate B3 | 85 | C₂₁H₁₇Br/ 349.26 |
| 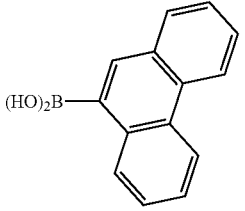<br>Reactant A3 | 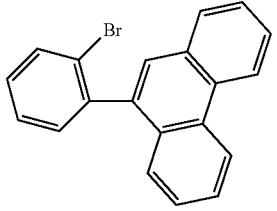<br>Intermediate B4 | 83 | C₂₀H₁₃Br/ 333.22 |
| 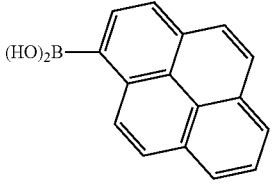<br>Reactant A4 | 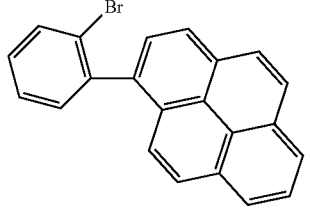<br>Intermediate B5 | 76 | C₂₂H₁₃Br/ 357.24 |
| 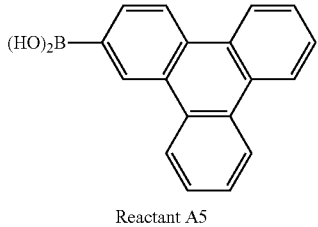<br>Reactant A5 | 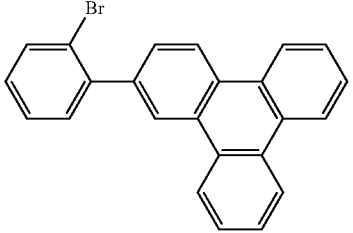<br>Intermediate B6 | 80 | C₂₄H₁₅Br/ 383.28 |

Note: Formula column uses LaTeX where appropriate: $C_{16}H_{11}Br$/283.16, $C_{21}H_{17}Br$/349.26, $C_{20}H_{13}Br$/333.22, $C_{22}H_{13}Br$/357.24, $C_{24}H_{15}Br$/383.28.

Synthesis of Intermediates B2

In addition to Scheme B-1, another synthesis pathway for Intermediate B2 was summarized in Scheme B-2.

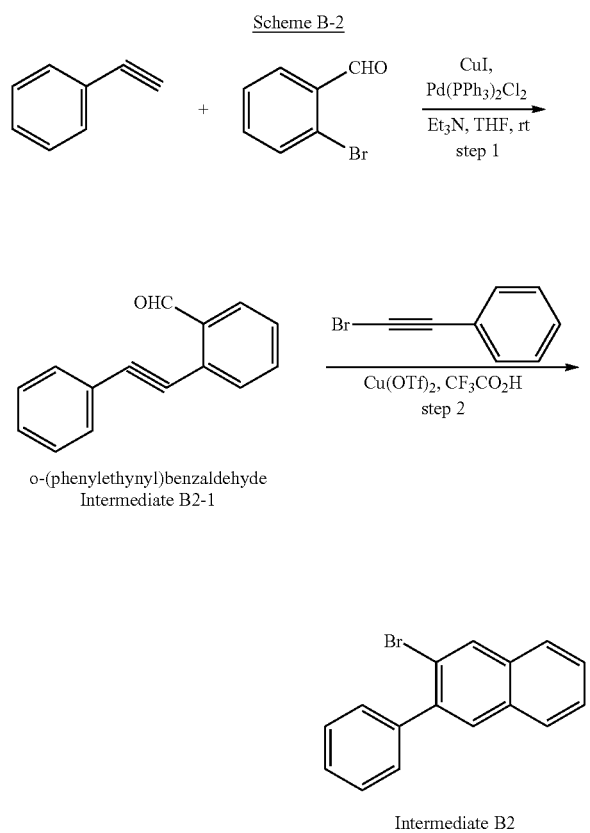

Step 1: Synthesis of Intermediate B2-1

A mixture of dichloro bis-(triphenylphosphine) palladium (0.05 eq) and 2-bromobenzaldehyde (1 eq) in THF (0.13-0.15 M) was added with triethylamine (3.0 eq). After being stirred for 10 min at room temperature, phenyl acetylene (1.5 eq) and copper iodide (0.05 eq) were added to the mixture. The resulting mixture was stirred at room temperature for 24 h. The reaction mixture was quenched with saturated aqueous of $NH_4Cl$, extracted with EtOAc three times, and washed with brine. The organic layers were dried over $Na_2SO_4$ and concentrated under a reduced pressure after filtration. The crude mixture was purified by silica-gel column chromatography to obtain Intermediate B2-1 in a yield of 92.4%. The product was identified as Intermediate B2-1 by FD-MS analysis. FD-MS analysis: $C_{15}H_{10}O$: theoretical value of 206.64 and observed value of 206.64.

Step 2: Synthesis of Intermediate B2

A mixture of intermediate B2-1 (1.0 eq) and $Cu(OTf)_2$ (0.05 eq) in 1,2-dichloroethane (5 times of Intermediate B2-1) were added with 1-(2-bromoethynyl)benzene (1.2 eq) and $CF_3CO_2H$ (1.0 eq) successively at room temperature under argon atmosphere. The resulting mixture was stirred at 100° C. for 15 min and then cooled to room temperature. A saturated aqueous solution of $NaHCO_3$ was added, and the mixture was extracted with ether three times. The combined extracts were washed with brine, dried over $MgSO_4$, and evaporated to leave the crude product. The crude product was then purified by silica gel column chromatography using hexane as an eluent to give Intermediate B2 (yield 80%). The product was identified as intermediate B2 by FD-MS analysis. FD-MS analysis: $C_{16}H_{11}Br$: theoretical value of 283.16 and observed value of 283.16.

Modifications of Intermediates B1 to B6

In addition to the Intermediates B1 to B6, one person skilled in the art can adopt any aryl boronic acid other than Reactants A1 to A5 to react with 1-bromo-2-iodobenzene to successfully synthesize other desired Intermediate Bn through a reaction mechanism similar to Scheme B-1. Similarly, one person skilled in the art can synthesize other desired Intermediate Bn through a reaction mechanism similar to Scheme B-2. Applicable modifications of Intermediates B1 to B6 may be, for example, but not limited to, Intermediates B7 and B14 as follows.

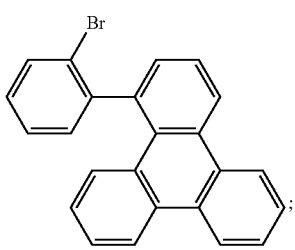

Intermediate B7

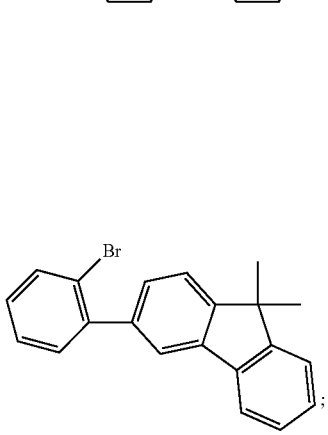

Intermediate B8

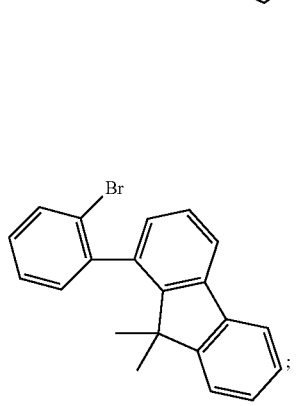

Intermediate B9

-continued

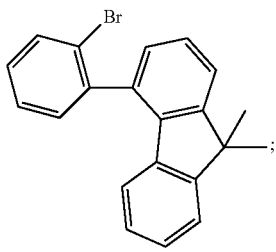
Intermediate B10

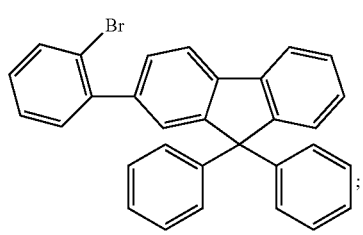
Intermediate B11

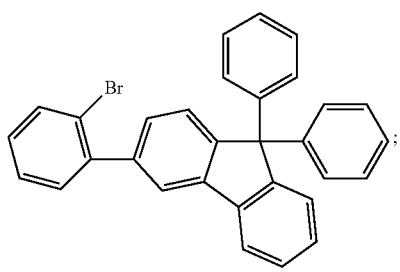
Intermediate B12

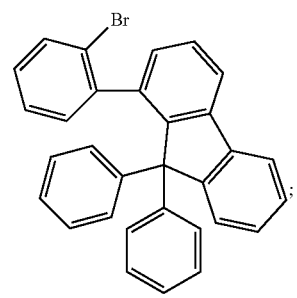
Intermediate B13

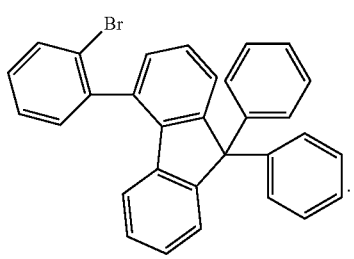
Intermediate b14

Synthesis of Intermediates C

The foresaid Intermediates B1 to B14, especially Intermediates B1 to B6, could be further adopted to synthesize Intermediate Cn. A general synthesis pathway for Intermediate Cn was summarized in Scheme C1. In the following Scheme C1, "Intermediate An" may be any one of foresaid Intermediates A1 to A15 or the like, "Intermediate Bn" may be any one of foresaid Intermediates B1 to B14 or the like, and "Intermediate Cn" may be any one of Intermediates C1 to C9 as listed in Table 3-1 or the like. Intermediates C1 to C9 were each synthesized by the following steps.

Scheme C1

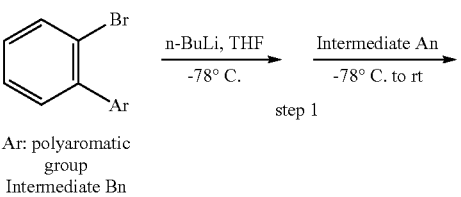

Ar: polyaromatic group
Intermediate Bn

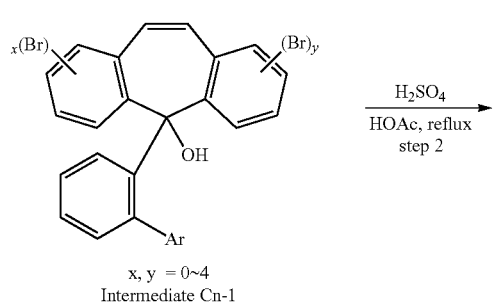

x, y = 0~4
Intermediate Cn-1

Intermediate Cn

Step 1: Synthesis of Alcohol Intermediate (Intermediate Cn-1)

Intermediate Bn (1.0 eq) was dissolved in 120 mL of anhydrous THF (0.4M), and cooled to −78° C. n-Butyl lithium (n-BuLi) (2.5 M, 1.0 eq) was slowly added to the above cooled solution, and the reaction mass was stirred for 1 h. After 1 h of stirring, Intermediate An (0.7 eq) was added to the reaction solution and stirred for additional 3 h at normal temperature. After the completion of the reaction, it was quenched by saturated solution of ammonium chloride, and extracted with organic solvent. The organic layer was separated, concentrated, and recrystallized with petroleum ether to obtain a white solid product.

The white solid product was analyzed by FD-MS, and the result was listed in Table 3-1. The chemical structures of Intermediates Cn-1 were listed in Table 3-1.

Step 2: synthesis of Intermediate Cn

The foresaid Intermediate Cn-1 (1.0 eq), acetic acid (w/v=⅓ to the reactant) and $H_2SO_4$ (5 drops) were mixed, and then stirred at 110° C. for 6 h. The solvent was then removed under reduced pressure, and the residue was purified with column chromatography. The residual mass was recrystallized with toluene to obtain a white solid product.

The solid product was identified by FD-MS analysis. The chemical structures, yields, formulae, and mass analyzed by FD-MS of Intermediates C1 to C9 were listed in Table 3-1.

TABLE 3-1

Intermediate A and B used for preparing Intermediates C1 to C9, chemical structures of alcohol intermediates, and chemical structures, yields, formulae, and mass analyzed by FD-MS of Intermediates C1 to C9.

| Intermediate An | Intermediate Bn | Alcohol intermediate Chemical Structure | Yield (%) | Intermediate Cn Chemical Structure/ Formula/Mass (M+) | Yield (%) |
|---|---|---|---|---|---|
| A1 | B1 | 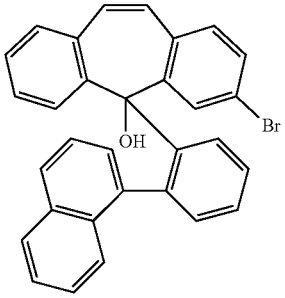 Intermediate C1-1/ C$_{31}$H$_{21}$BrO/ 489.40 | 88.5 | 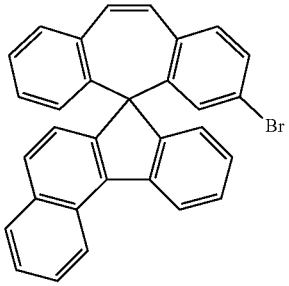 Intermediate C1/ C$_{31}$H$_{19}$Br/ 471.39 | 95.0 |
| A3 | B1 | 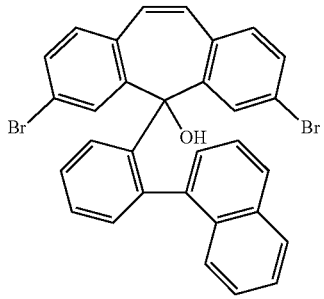 Intermediate C2-1 | 85 | 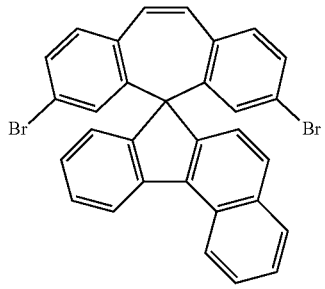 Intermediate C2/ C$_{31}$H$_{18}$Br$_2$/ 550.28 | 94 |
| A1 | B2 | 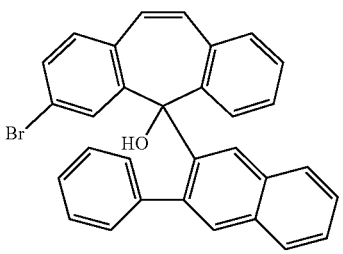 Intermediate C3-1 | 77 | 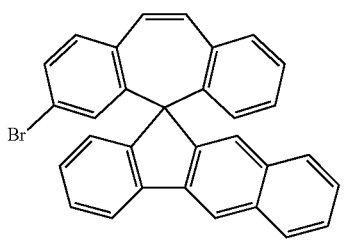 Intermediate C3 | 90 |
| A1 | B3 | 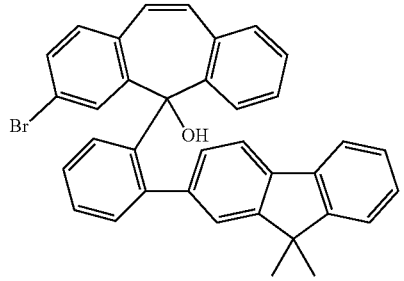 Intermediate C4-1 | 80 | 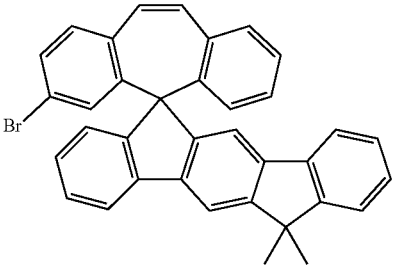 Intermediate C4 | 88 |

TABLE 3-1-continued

Intermediate A and B used for preparing Intermediates C1 to C9, chemical structures of alcohol intermediates, and chemical structures, yields, formulae, and mass analyzed by FD-MS of Intermediates C1 to C9.

| Intermediate An | Intermediate Bn | Alcohol intermediate Chemical Structure | Yield (%) | Intermediate Cn Chemical Structure/ Formula/Mass (M+) | Yield (%) |
|---|---|---|---|---|---|
| A1 | B4 | Intermediate C5-1 | 78 | Intermediate C5 | 90 |
| A3 | B4 | Intermediate C6-1 | 90 | Intermediate C6/ $C_{35}H_{20}Br_2$/ 600.34 | 88 |
| A1 | B5 | Intermediate C7-1 | 94 | Intermediate C7 | 70 |

TABLE 3-1-continued

Intermediate A and B used for preparing Intermediates C1 to C9, chemical structures of alcohol intermediates, and chemical structures, yields, formulae, and mass analyzed by FD-MS of Intermediates C1 to C9.

| Intermediate An | Intermediate Bn | Alcohol intermediate Chemical Structure | Yield (%) | Intermediate Cn Chemical Structure/ Formula/Mass (M+) | Yield (%) |
|---|---|---|---|---|---|
| A1 | B6 | Intermediate C8-1 | 86 | Intermediate C8 | 87 |
| A3 | B6 | Intermediate C9-1 | 80 | Intermediate C9/ $C_{39}H_{22}Br_2$/ 650.40 | 92 |

Modifications of Intermediates C1 to C9

In addition to the Intermediates C1 to C9, one person skilled in the art can adopt any intermediate A other than Intermediates A1 and A3 and any Intermediate B other than Intermediates B1 to B6 to successfully synthesize other desired Intermediate C through a reaction mechanism similar to Scheme C1. Applicable modifications of Intermediates C1 to C9 may be, for example, but not limited to, Intermediates C10 to C21 as follows.

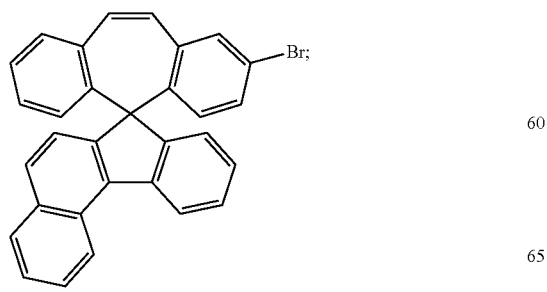

Intermediate C10

Intermediate C11
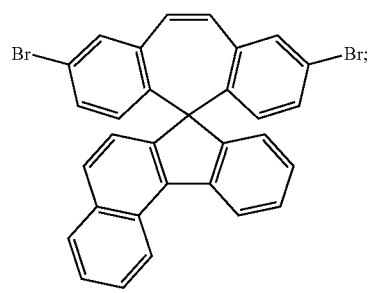
Intermediate C12
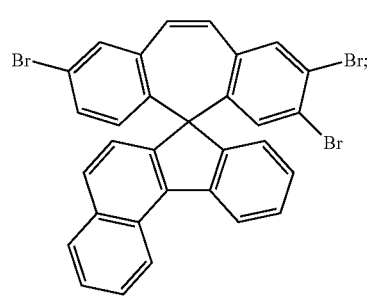
Intermediate C13
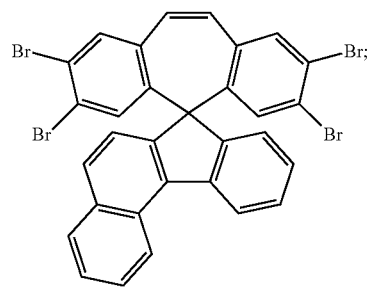
Intermediate C14
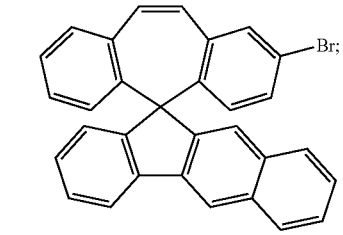
Intermediate C15
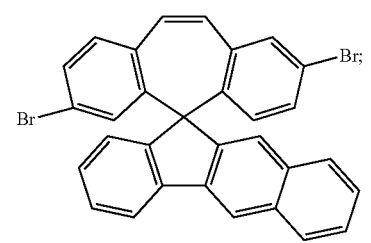
Intermediate C16
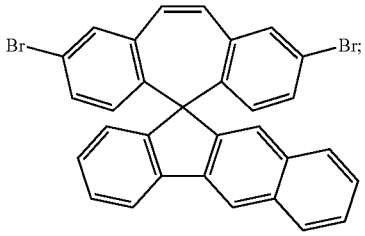
Intermediate C17
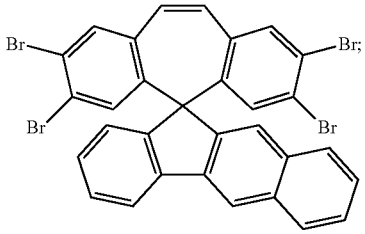
Intermediate C18
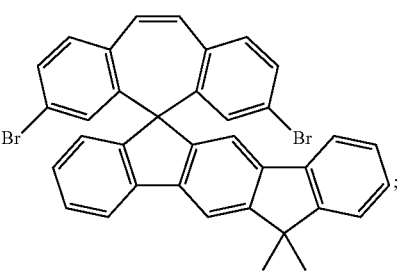
Intermediate C19
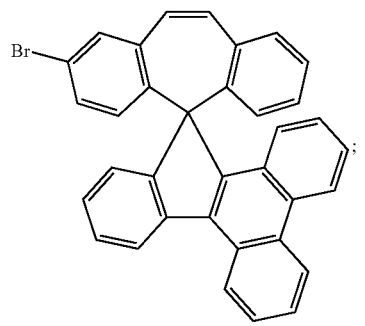
Intermediate C20
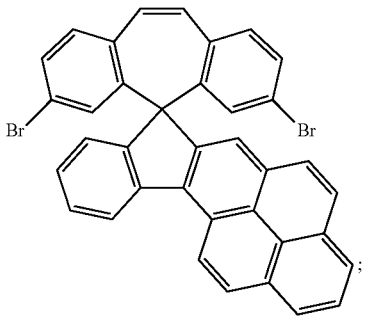

Intermediate C21

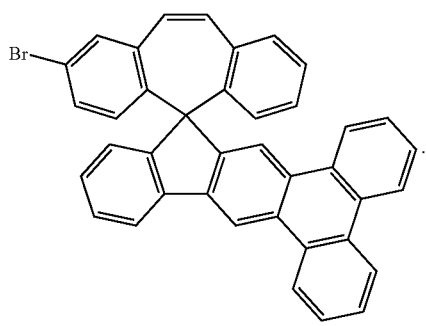

Scheme C1-B

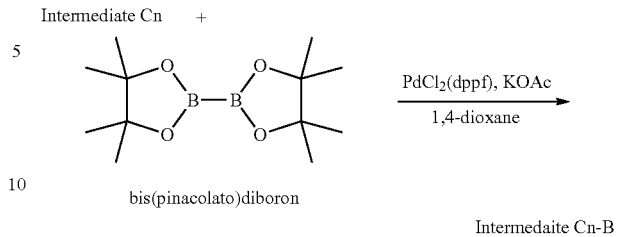

bis(pinacolato)diboron

Intermedaite Cn-B

Synthesis of Intermediate Cn-B

The foresaid Intermediate Cn could be further modified into an Intermediate Cn-B through Miyaura borylation reaction. "Intermediate Cn-B" was directed to a compound derived from Intermediate Cn whose bromo group was replaced by (pinacolato)boron group. A synthesis pathway of Intermediate Cn-B was summarized in Scheme C1-B. Intermediate Cn-B was synthesized by the following steps.

A mixture of bis(pinacolato)diboron (1.2 eq), Intermediate Cn (1.0 eq), 1,1-bis(diphenylphosphino)-ferrocenedichloropalladium (II) ($PdCl_2$ (dppf)) (0.015 eq), and potassium acetate (KOAc) (3.0 eq) in 1,4-dioxane (0.3 M) was stirred at 110° C. for 8 hours under nitrogen atmosphere. After cooling to room temperature, the solvent was then removed under reduced pressure, and the residue was purified via column chromatography to obtain a pale yellow solid product.

The pale yellow solid product was identified by FD-MS analysis. The chemical structures, yields, formulae, and mass analyzed by FD-MS of Intermediates Cn-B were listed in Table 3-2.

Table 3-2

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass (M⁺) |
| Intermediate C1/ $C_{31}H_{19}Br$/ 471.39 | 95.0 | Intermediate C1-B | 91 | $C_{37}H_{31}BO_2$/ 518.45 |
| Intermediate C3 | 90 | Intermediate C3-B | 93 | $C_{37}H_{31}BO_2$/ 518.45 |

Table 3-2-continued

Intermediate Cn used for preparing Intermediate Cn-B and chemical structures, yields,
formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass (M+) |
| 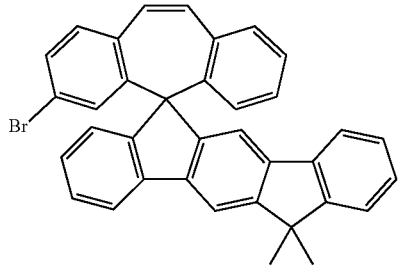 Intermediate C4 | 88 | 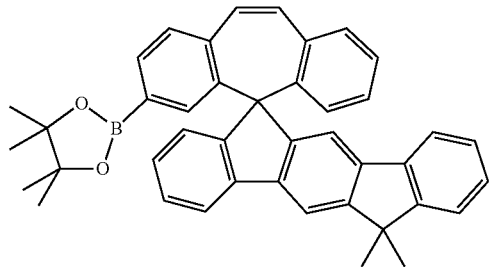 Intermediate C4-B | 92 | $C_{42}H_{37}BO_2$/ 584.55 |
| 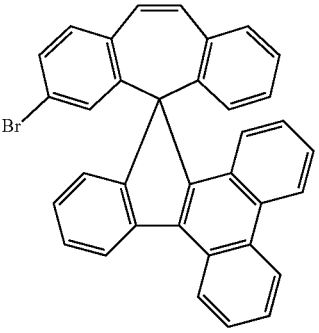 Intermediate C5 | 90 | 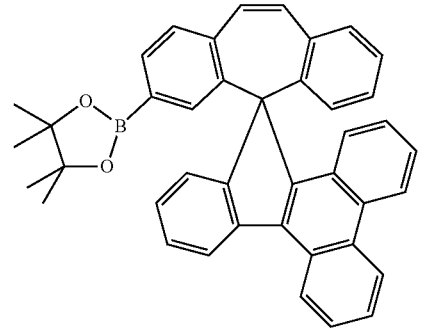 Intermediate C5-B | 91 | $C_{41}H_{33}BO_2$/ 568.51 |
| 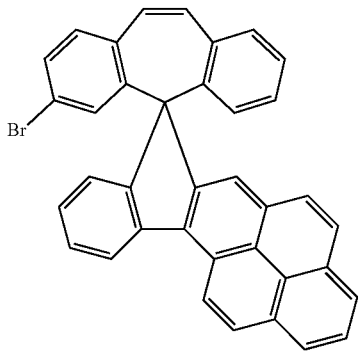 Intermediate C7 | 70 | 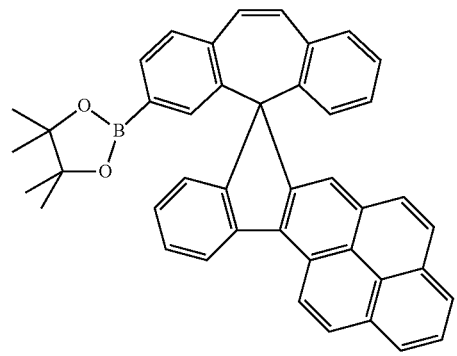 Intermediate C7-B | 94 | $C_{43}H_{33}BO_2$/ 592.53 |

Table 3-2-continued

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass (M⁺) |
| Intermediate C8 | 87 | Intermediate C8-B | 91 | $C_{45}H_{35}BO_2$/ 618.57 |

Modifications of Intermediate Cn-B

In addition to the Intermediate Cn-B, one person skilled in the art can adopt any one of foresaid Intermediates Cn to undergo a Miyaura borylation reaction to successfully synthesize other desired Intermediate Cn-B.

Synthesis of Novel Compounds

Each of the foresaid Intermediates Cn and Cn-B could be reacted with various reactants to synthesis various claimed novel compounds. The general synthesis pathway of the claimed novel compound was summarized in Scheme I. In the following Scheme I, "Reactant Bn" may be any one of Reactants B1 to B25 as listed in Table 4, and "Intermediate C" may be any one of the foresaid Intermediates Cn and Cn-B or the like. The compounds were each synthesized by the following steps.

Scheme I

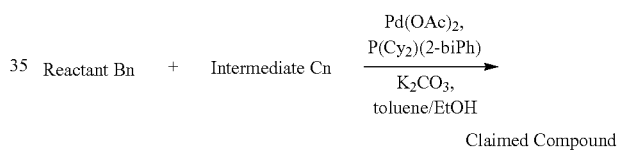

Reactant Bn + Intermediate Cn → Claimed Compound

Reagents: Pd(OAc)₂, P(Cy₂)(2-biPh), K₂CO₃, toluene/EtOH

TABLE 4 chemical structure and CAS No. of Reactants B1 to B25.

| Reactant No. | Reactant B1 | Reactant B2 | Reactant B3 |
|---|---|---|---|
| Chemical Structure | (HO)₂B—⟨⟩—CN | [pyridyl-Bpin] | [bipyridyl-Bpin] |
| CAS No. | [126747-14-6] | [329214-79-1] | [1260106-29-3] |
| Reactant No. | Reactant B4 | Reactant B5 | Reactant B6 |
| Chemical Structure | NC—⟨⟩—pyridyl—Br | [Cl-phenylquinazoline] | [Cl-diphenylpyrimidine] |

TABLE 4-continued chemical structure and CAS No. of Reactants B1 to B25.

| | | | |
|---|---|---|---|
| CAS No. | [916653-46-8] | [29874-83-7] | [29509-91-9] |
| Reactant No. | Reactant B7 | Reactant B8 | Reactant B9 |
| Chemical Structure | 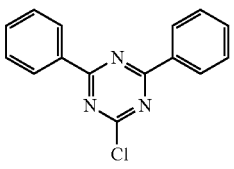 [SMILES: Clc1nc(-c2ccccc2)nc(-c2ccccc2)n1] | 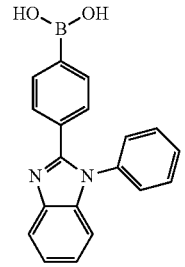 [SMILES: OB(O)c1ccc(-c2nc3ccccc3n2-c2ccccc2)cc1] | 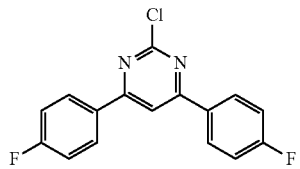 [SMILES: Fc1ccc(-c2cc(-c3ccc(F)cc3)nc(Cl)n2)cc1] |
| CAS No. | [3842-55-5] | [952514-79-3] | [1588407-97-9] |
| Reactant No. | Reactant B10 | Reactant B11 | Reactant B12 |
| Chemical Structure | 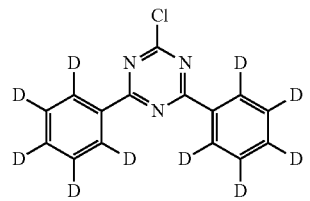 [SMILES: [2H]c1c([2H])c([2H])c(-c2nc(Cl)nc(-c3c([2H])c([2H])c([2H])c([2H])c3[2H])n2)c([2H])c1[2H]] | 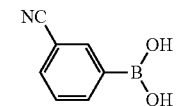 | 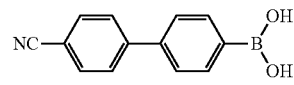 |
| CAS No. | [1300115-09-6] | [150255-96-2] | [406482-73-3] |
| Reactant No. | Reactant B13 | Reactant B14 | Reactant B15 |
| Chemical Structure | 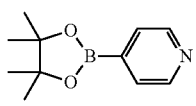 | 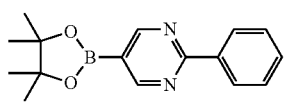 [SMILES: CC1(C)OB(c2cnc(-c3ccccc3)nc2)OC1(C)C] | 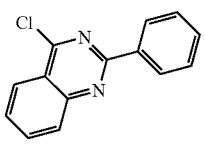 [SMILES: Clc1nc(-c2ccccc2)nc2ccccc12] |
| CAS No. | [181219-01-2] | [1319255-85-0] | [6484-25-9] |
| Reactant No. | Reactant B16 | Reactant B17 | Reactant B18 |
| Chemical Structure | 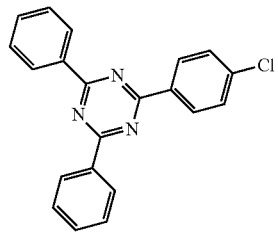 [SMILES: Clc1ccc(-c2nc(-c3ccccc3)nc(-c3ccccc3)n2)cc1] | 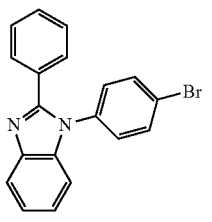 [SMILES: Brc1ccc(-n2c(-c3ccccc3)nc3ccccc32)cc1] | 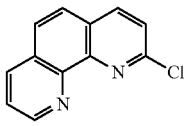 [SMILES: Clc1ccc2ccc3cccnc3c2n1] |
| CAS No. | [3114-52-1] | [867044-33-5] | [7089-68-1] |
| Reactant No. | Reactant B19 | Reactant B20 | Reactant B21 |
| Chemical Structure | 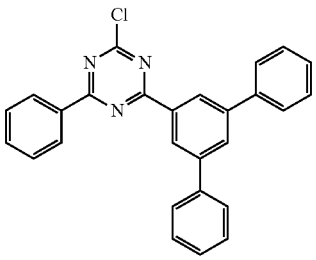 [SMILES: Clc1nc(-c2ccccc2)nc(-c2cc(-c3ccccc3)cc(-c3ccccc3)c2)n1] | 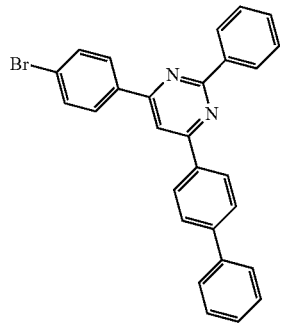 [SMILES: Brc1ccc(-c2cc(-c3ccc(-c4ccccc4)cc3)nc(-c3ccccc3)n2)cc1] | 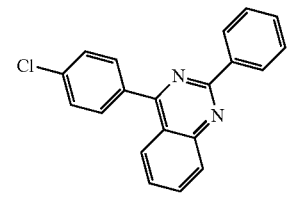 [SMILES: Clc1ccc(-c2nc(-c3ccccc3)nc3ccccc23)cc1] |

TABLE 4-continued chemical structure and CAS No. of Reactants B1 to B25.

| CAS No. | [1616231-57-2] | [1421599-34-9] | [99682-89-0] |
|---|---|---|---|
| Reactant No. | Reactant B22 | Reactant B23 | Reactant B24 |
| Chemical Structure | (structure) | (structure) | (structure) |

| Reactant No. | Reactant B25 |
|---|---|
| Chemical Structure | (structure) |

Intermediate Cn (1.0 eq), Reactant Bn (2.1 eq), Pd(OAc)$_2$ (0.01 eq), P(Cy)$_2$(2-biphenyl) 0.04 eq), toluene/ethanol (0.5M, v/v=10/1), and 3.0M of K$_2$CO$_3$ aqueous solution were mixed, followed by stirred at 100° C. for 12 h under nitrogen atmosphere. After completion of the reaction, water and toluene were added to the reaction mass. Subsequently, the organic layer was recovered by solvent extraction and dried over sodium sulfate. The solvent was then removed from the organic layer under a reduced pressure, and the resulting residue was purified by silica gel column chromatography. The obtained residue was recrystallized with toluene to obtain white solids as the claimed novel compound.

Figure 2:
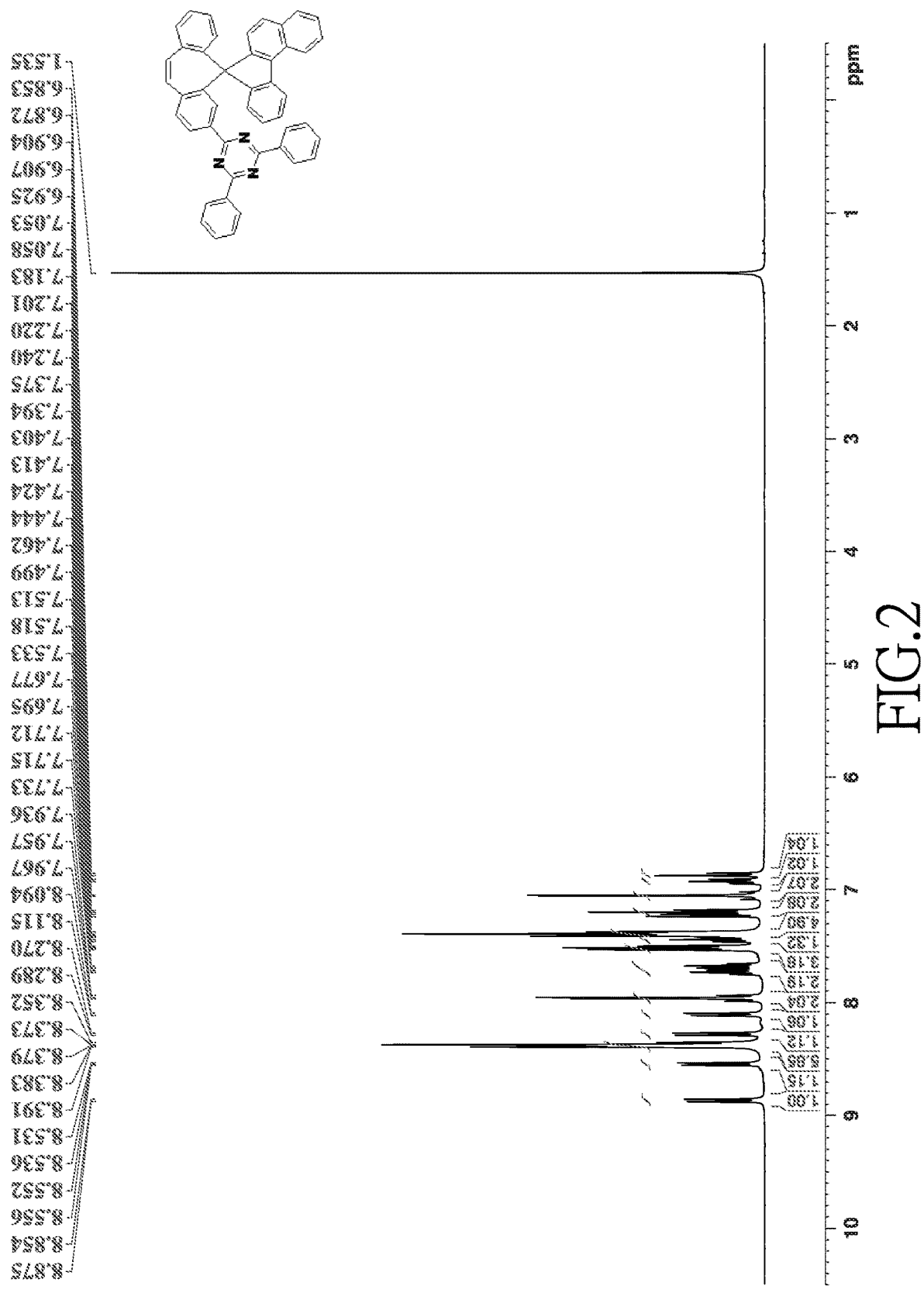
FIGS. 2 to 19 are respectively $^1$H nuclear magnetic resonance (NMR) spectra of Compounds I to XVIII.
Figure 3:
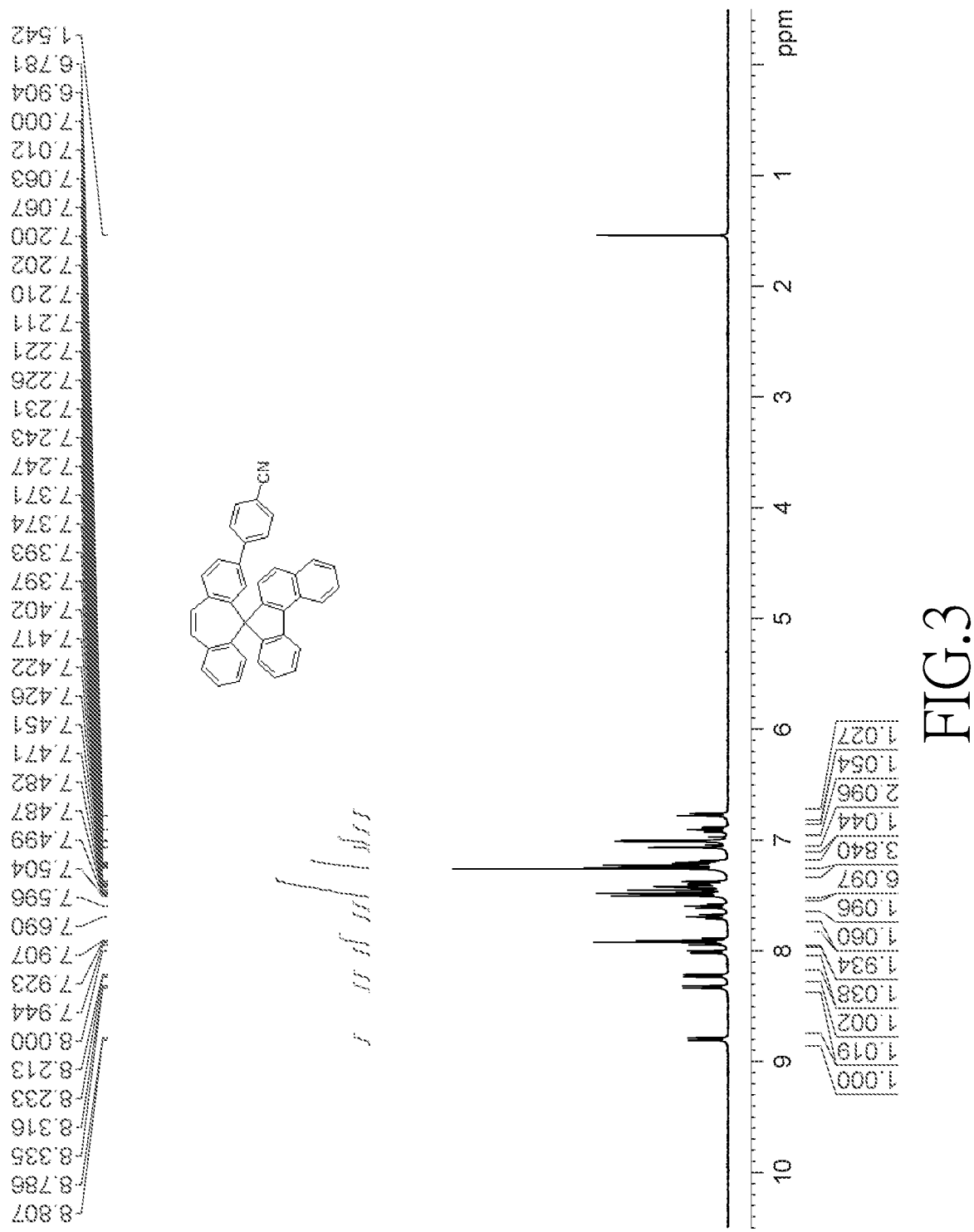
Figure 4:
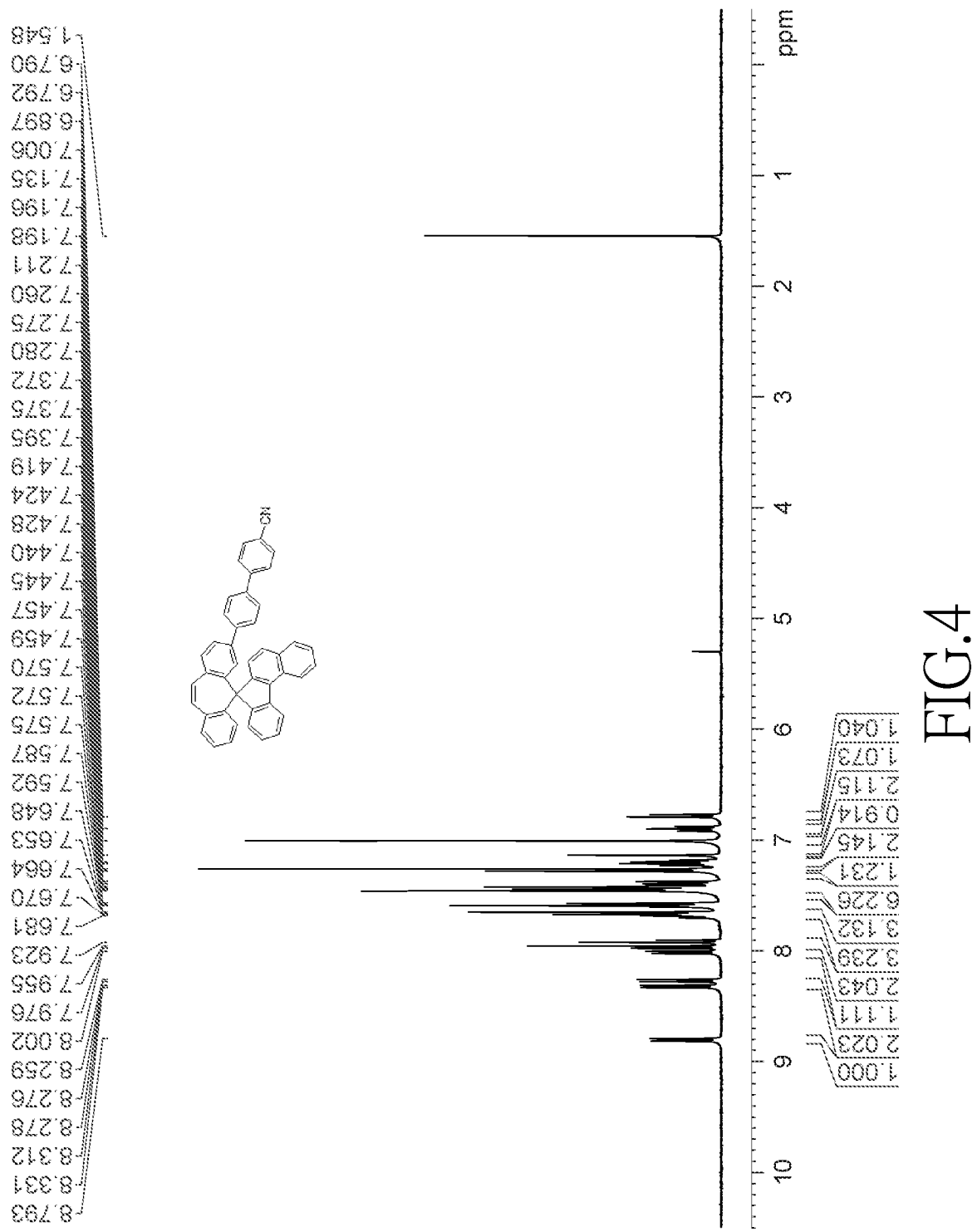
Figure 5:
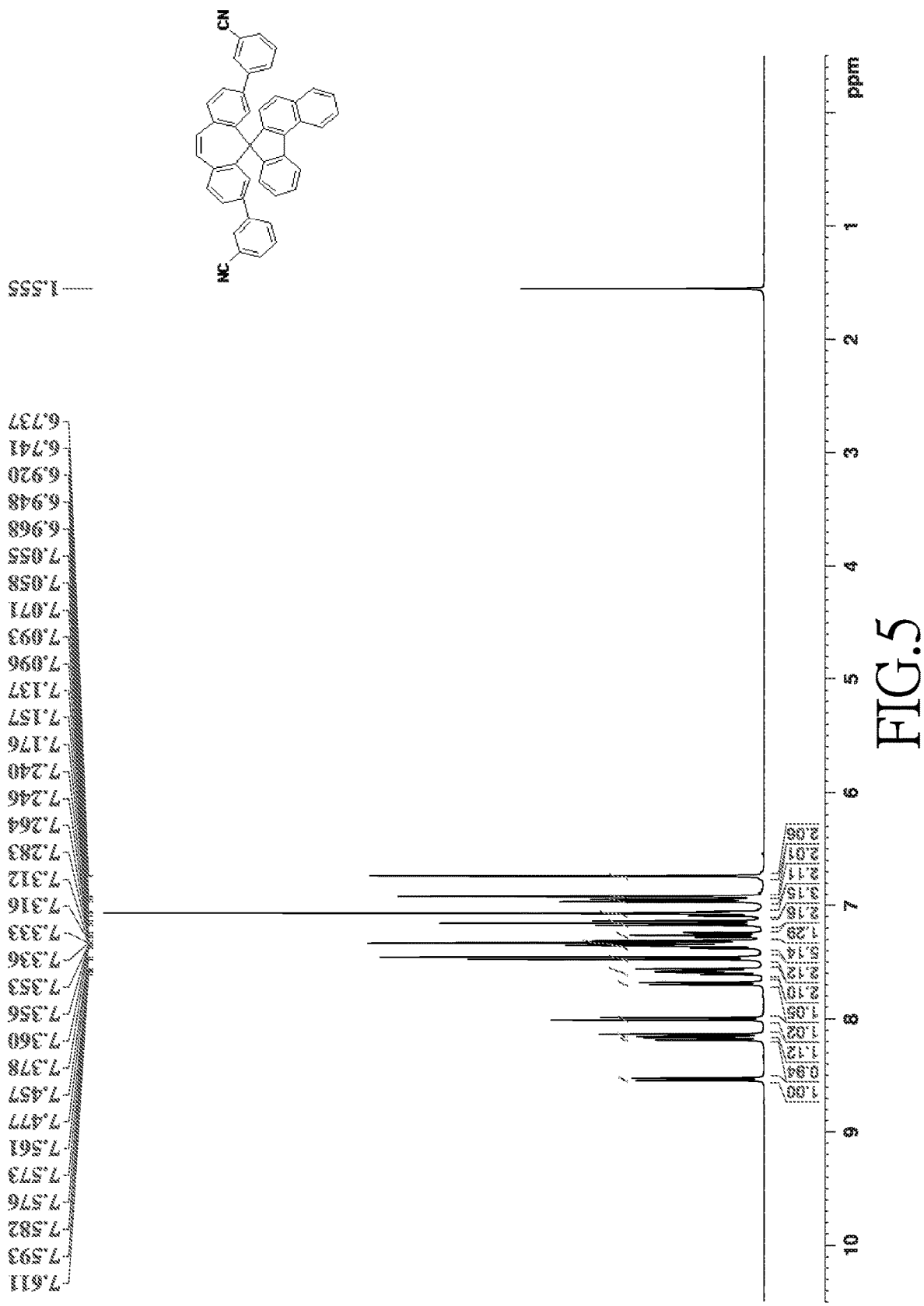
Figure 6:
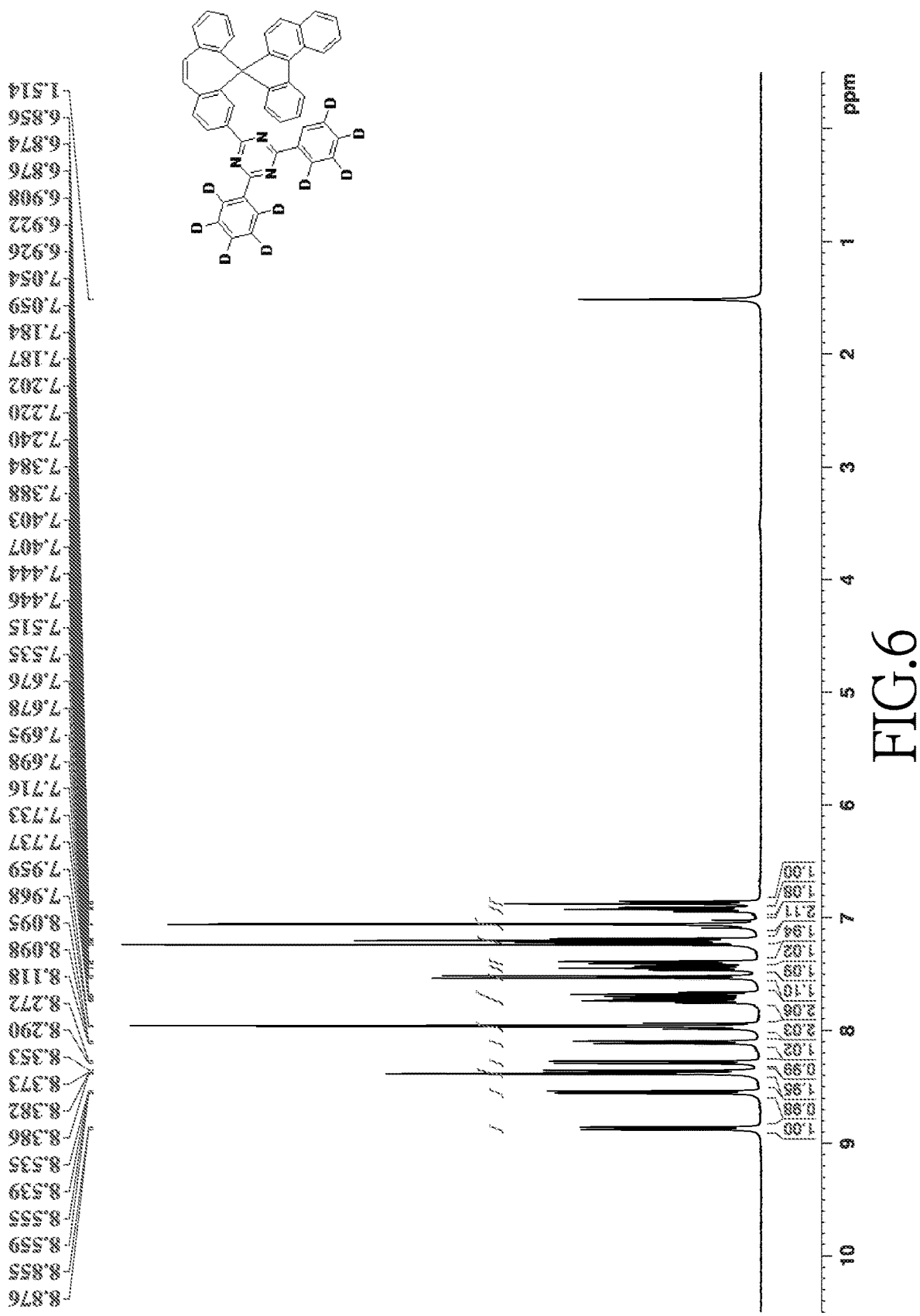
Figure 7:
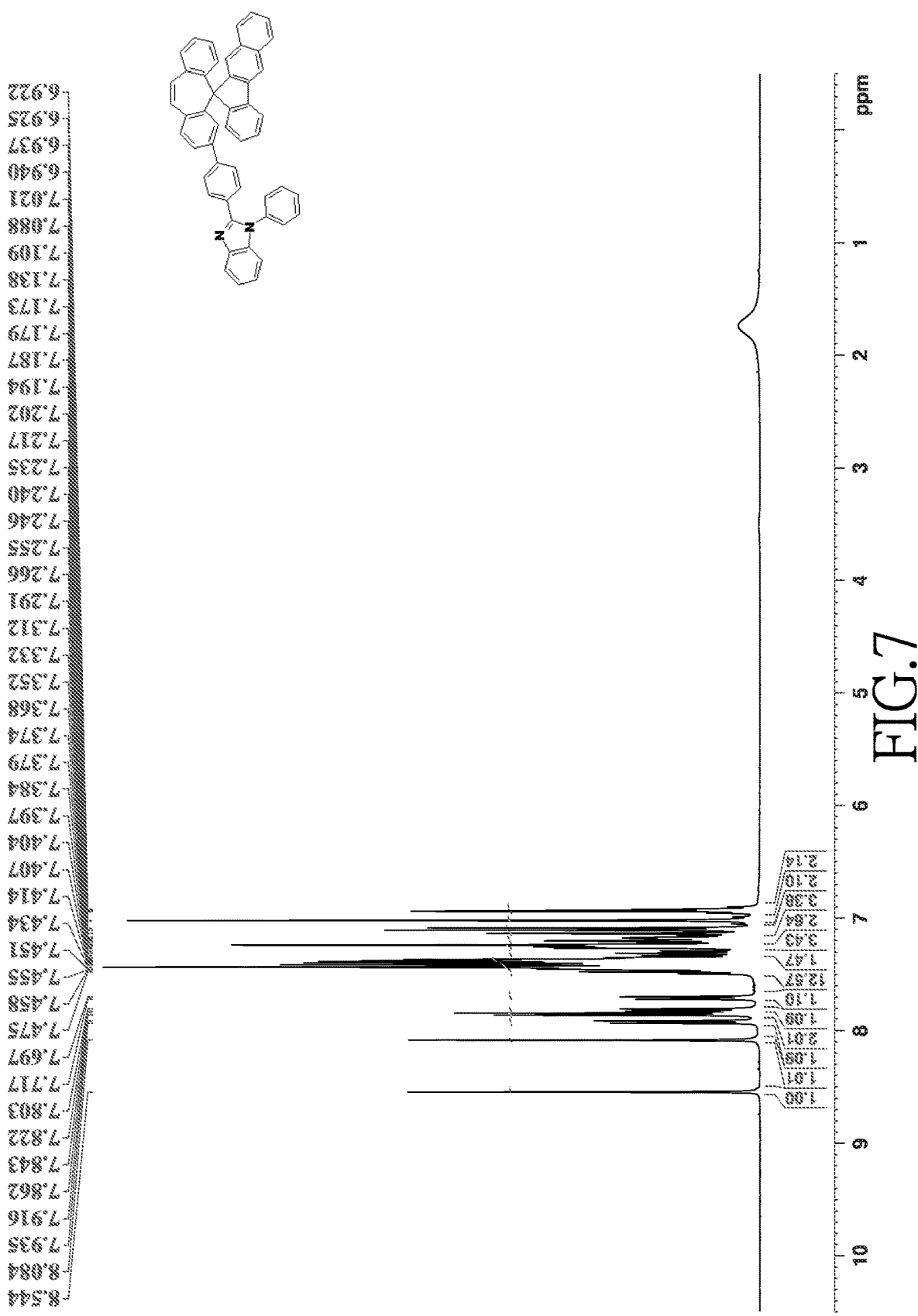
Figure 8:
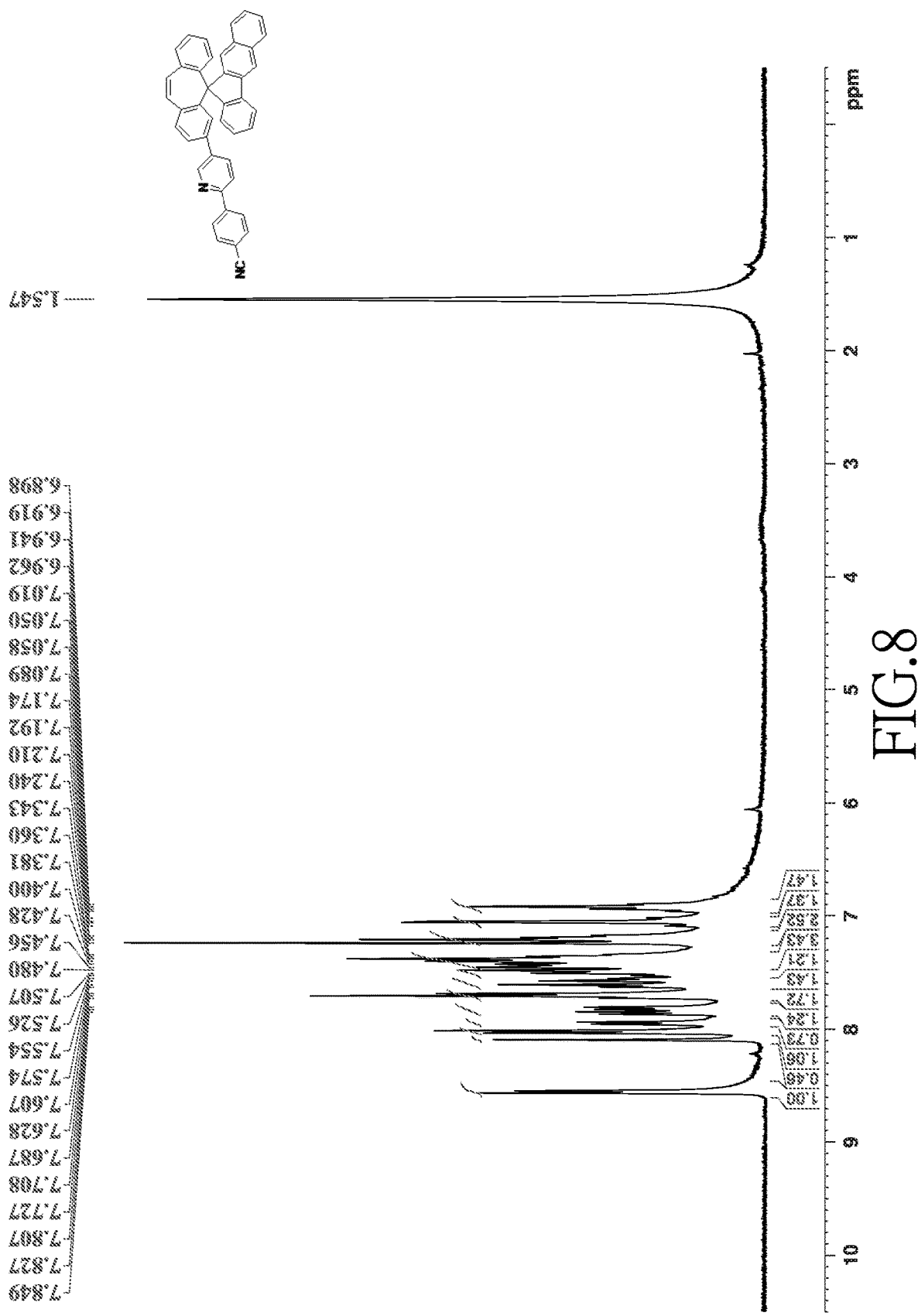
Figure 9:
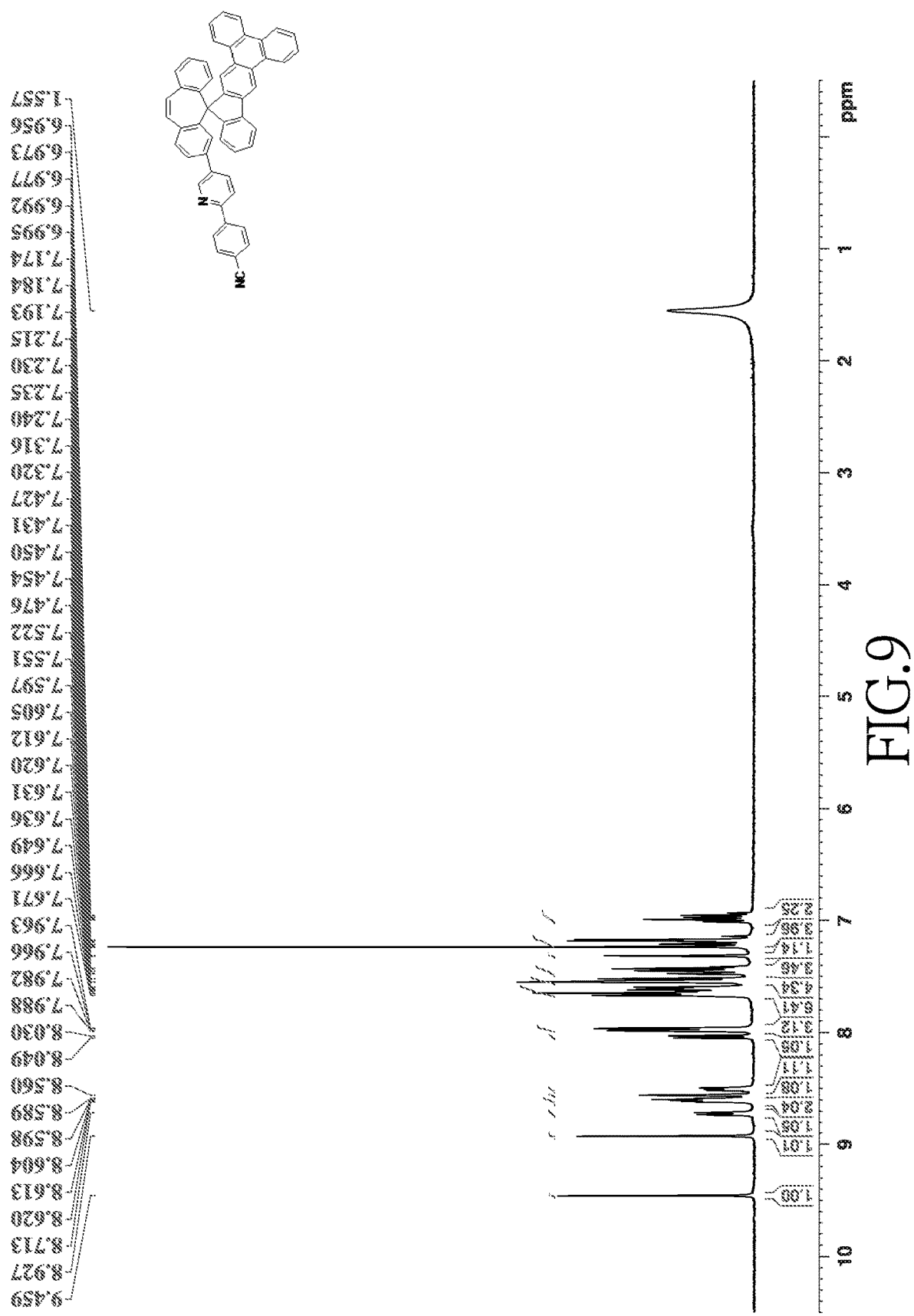
Figure 10:
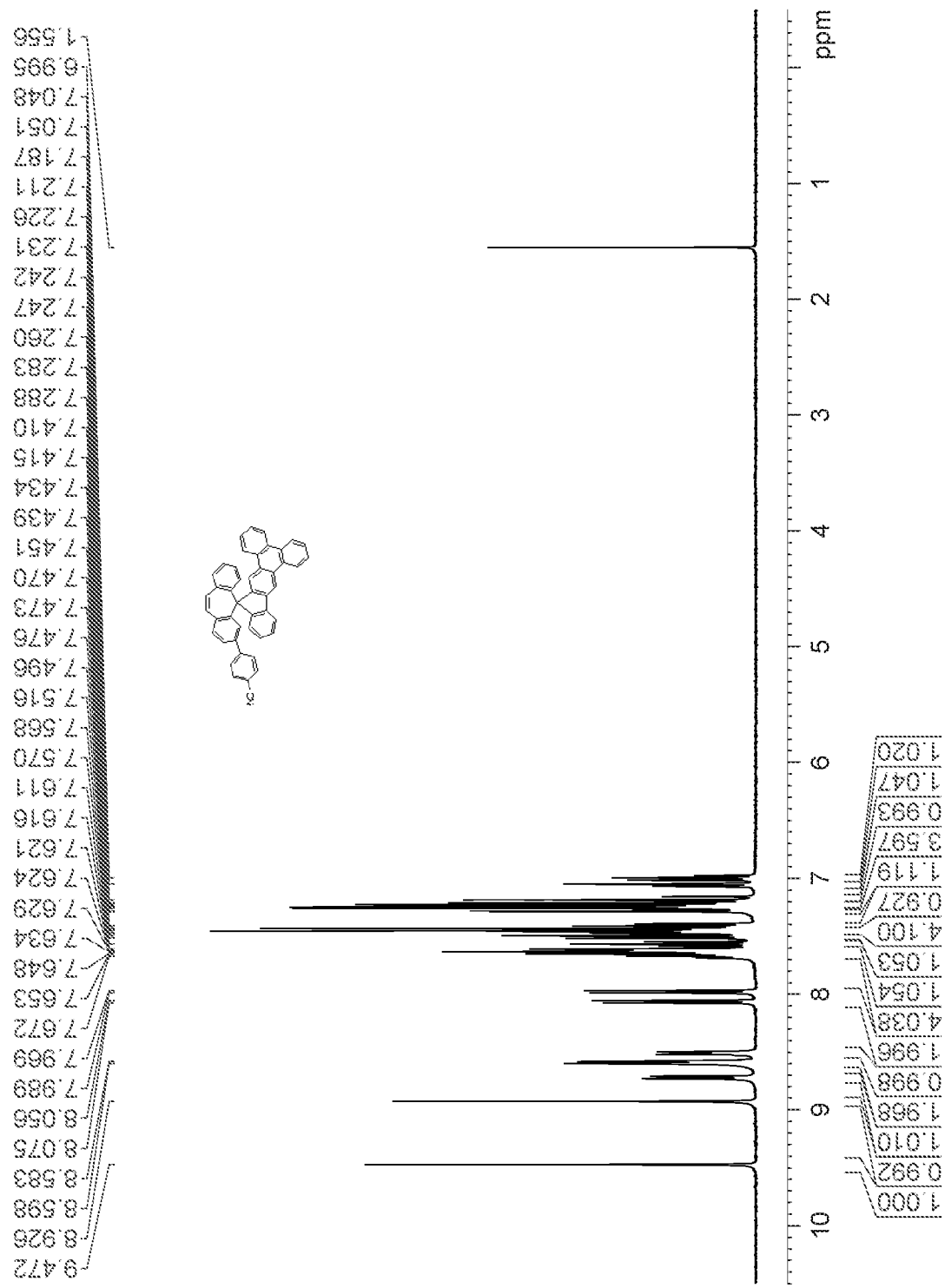
Figure 11:
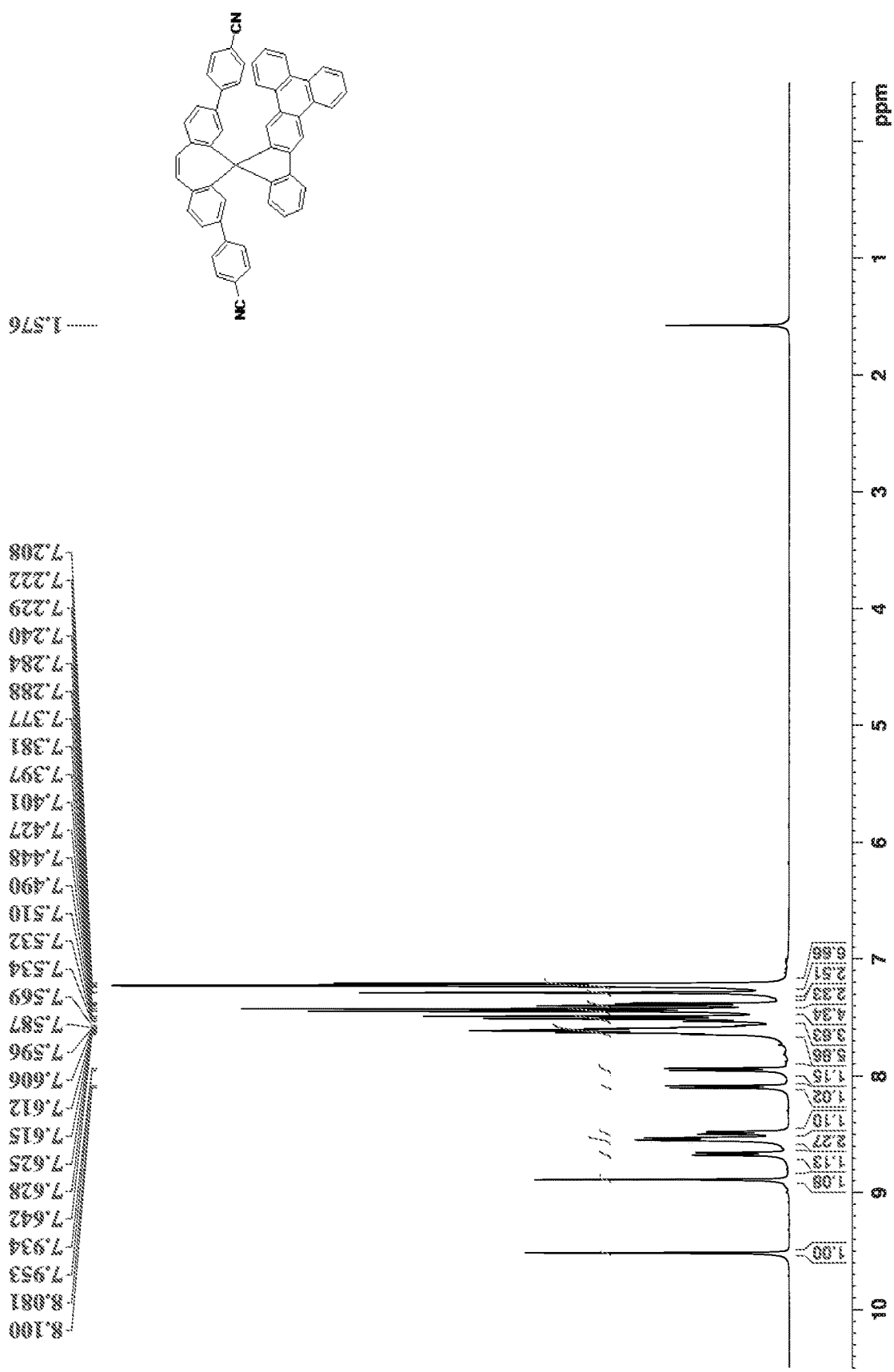
Figure 12:
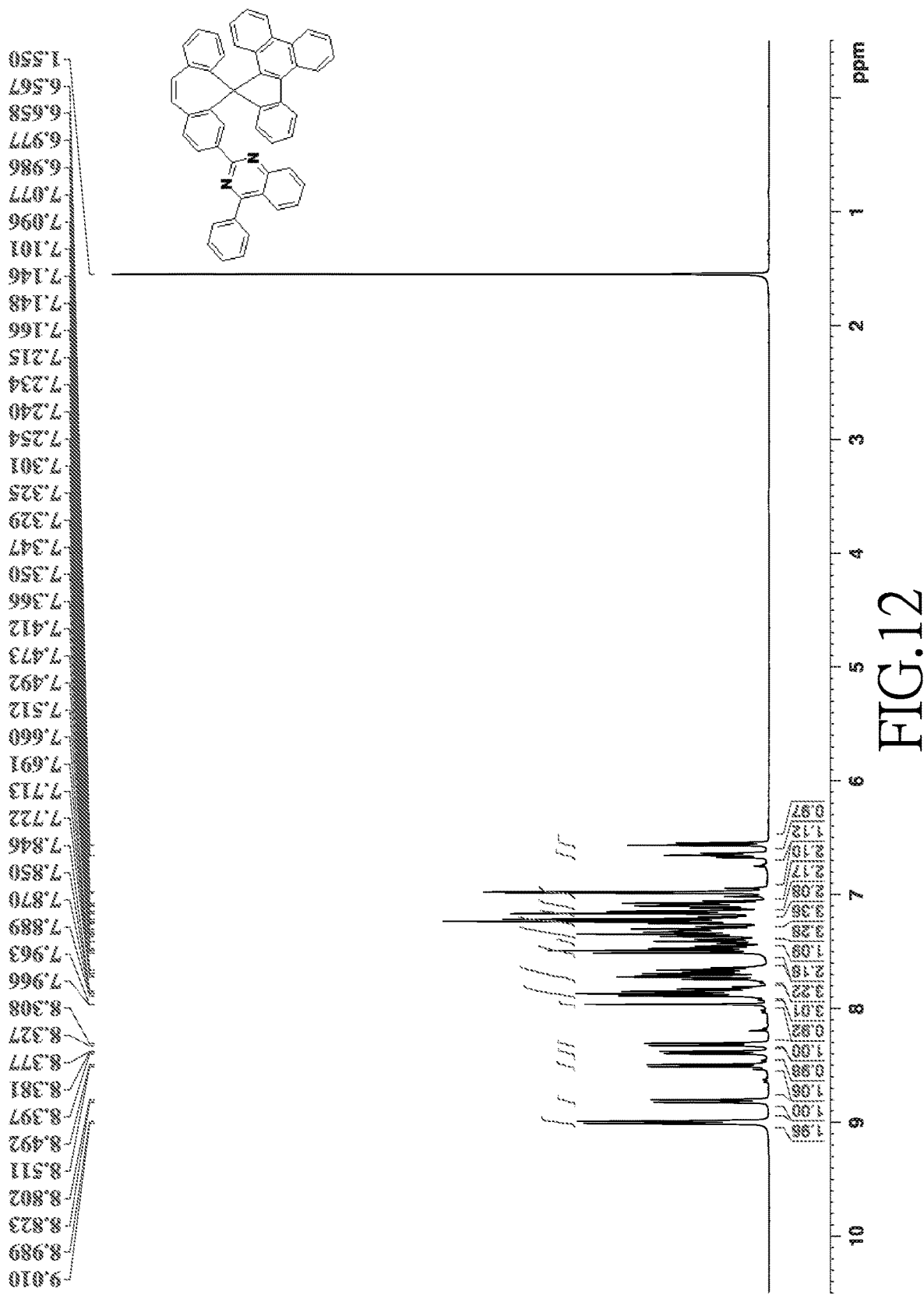
Figure 13:
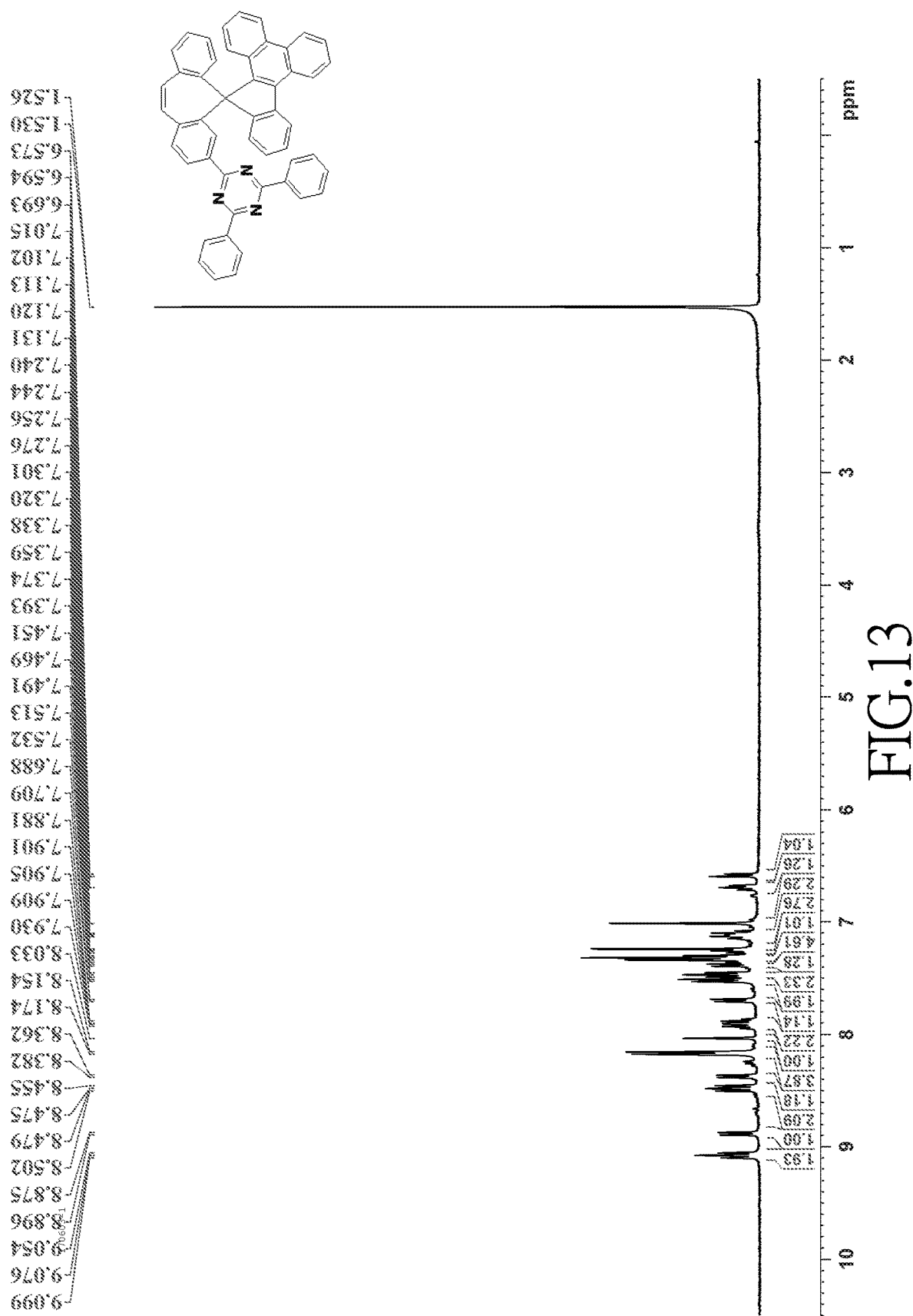
Figure 14:
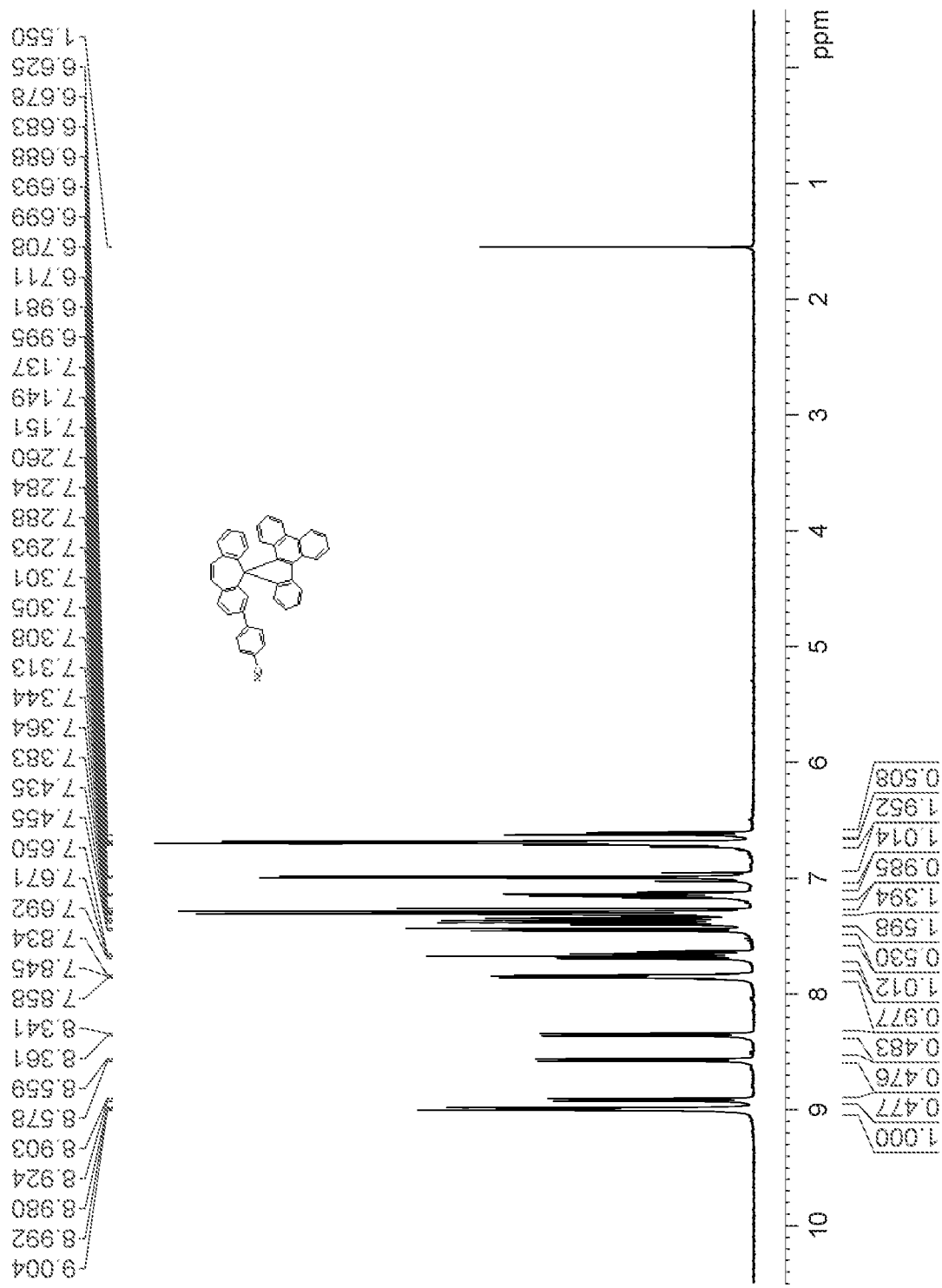
Figure 15:
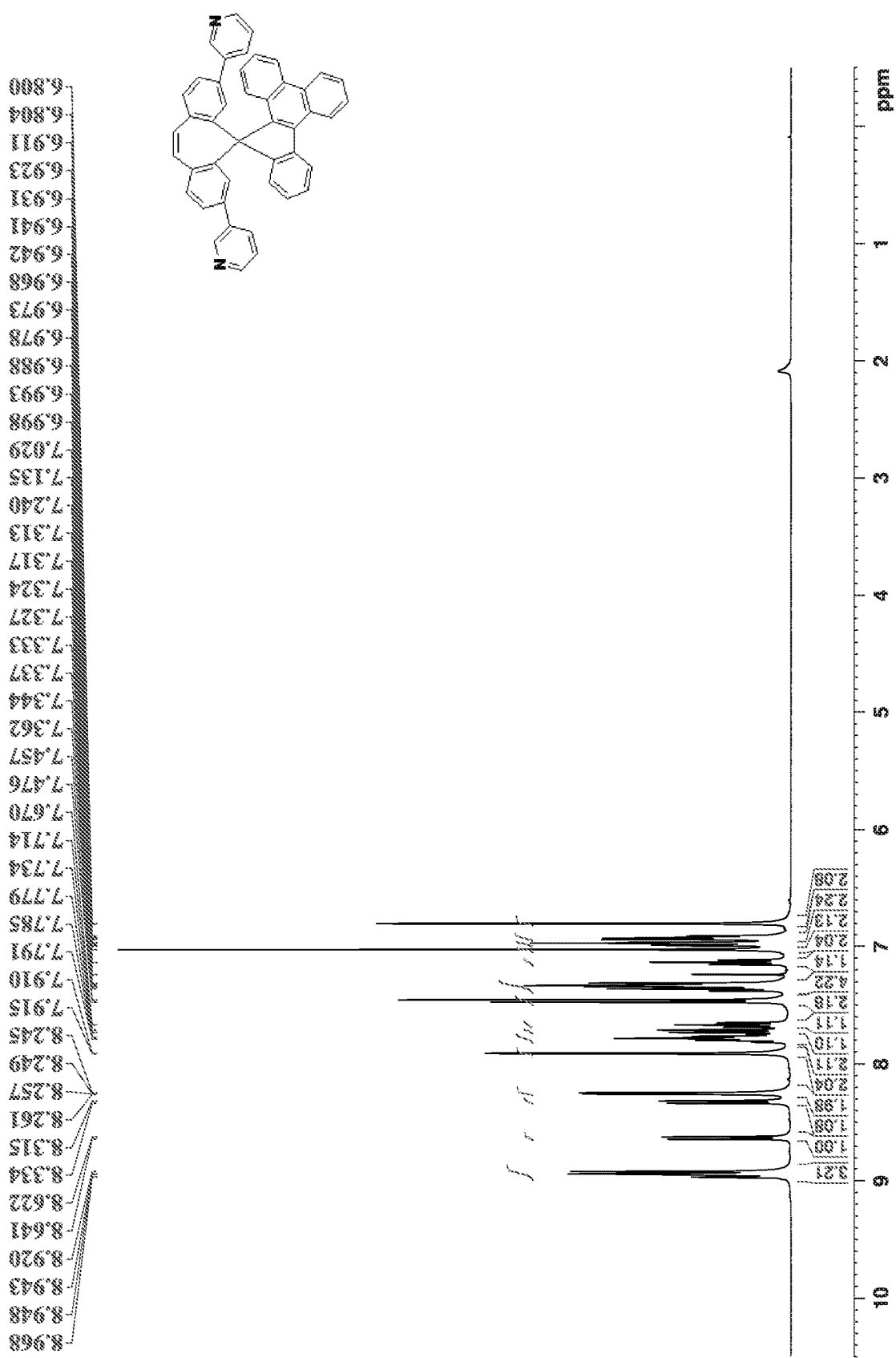
Figure 16:
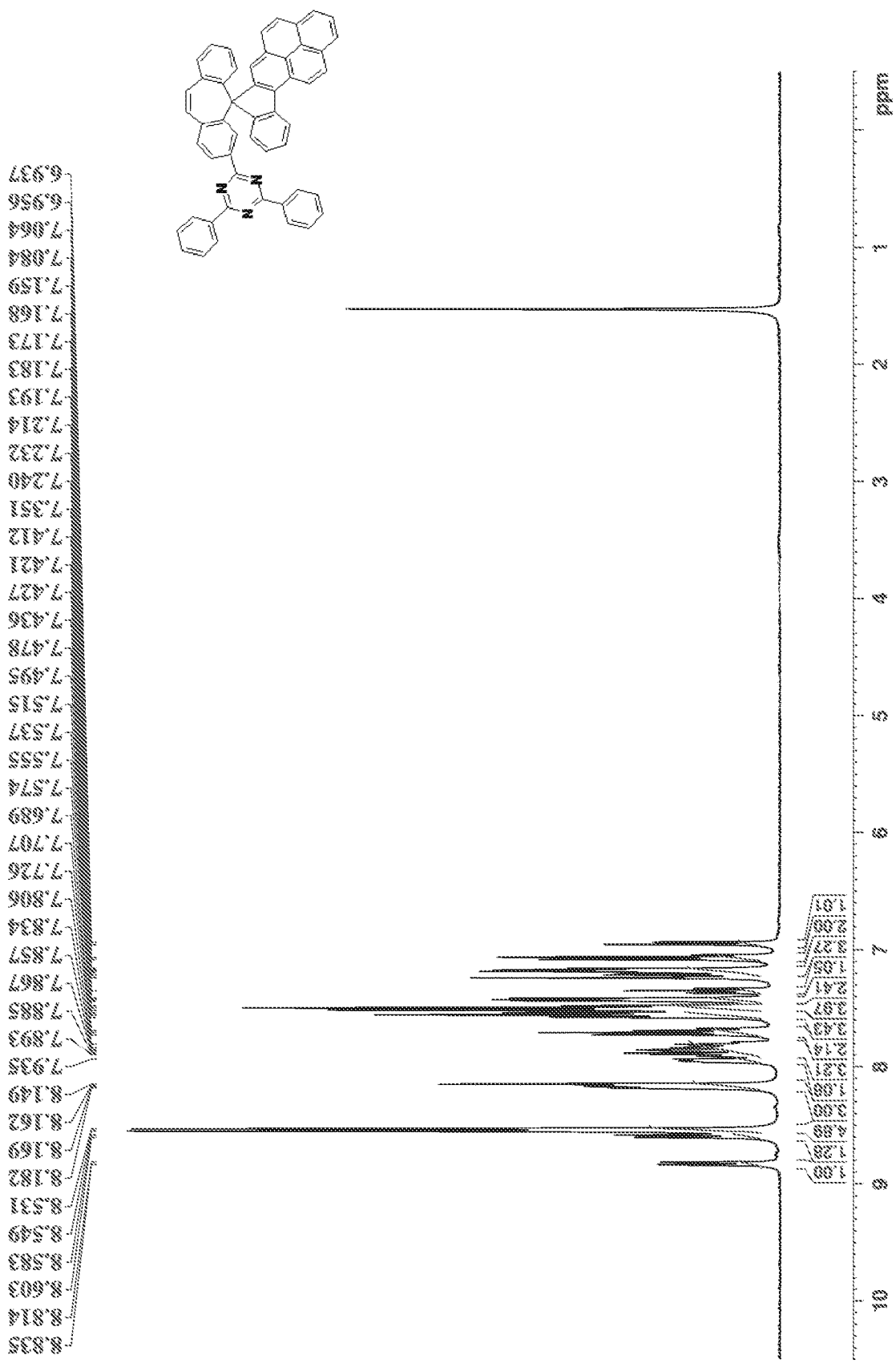
Figure 17:
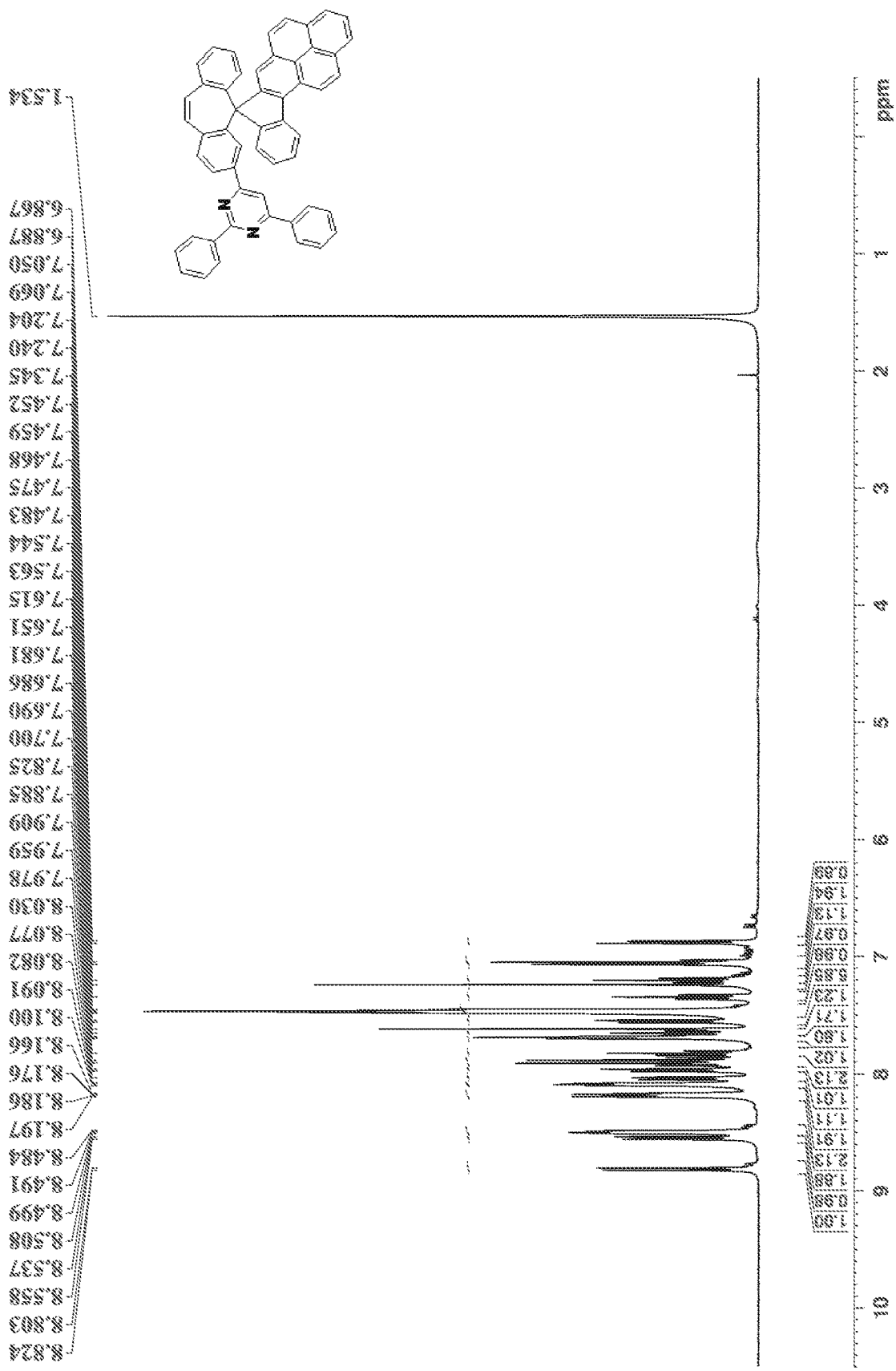
Figure 18:
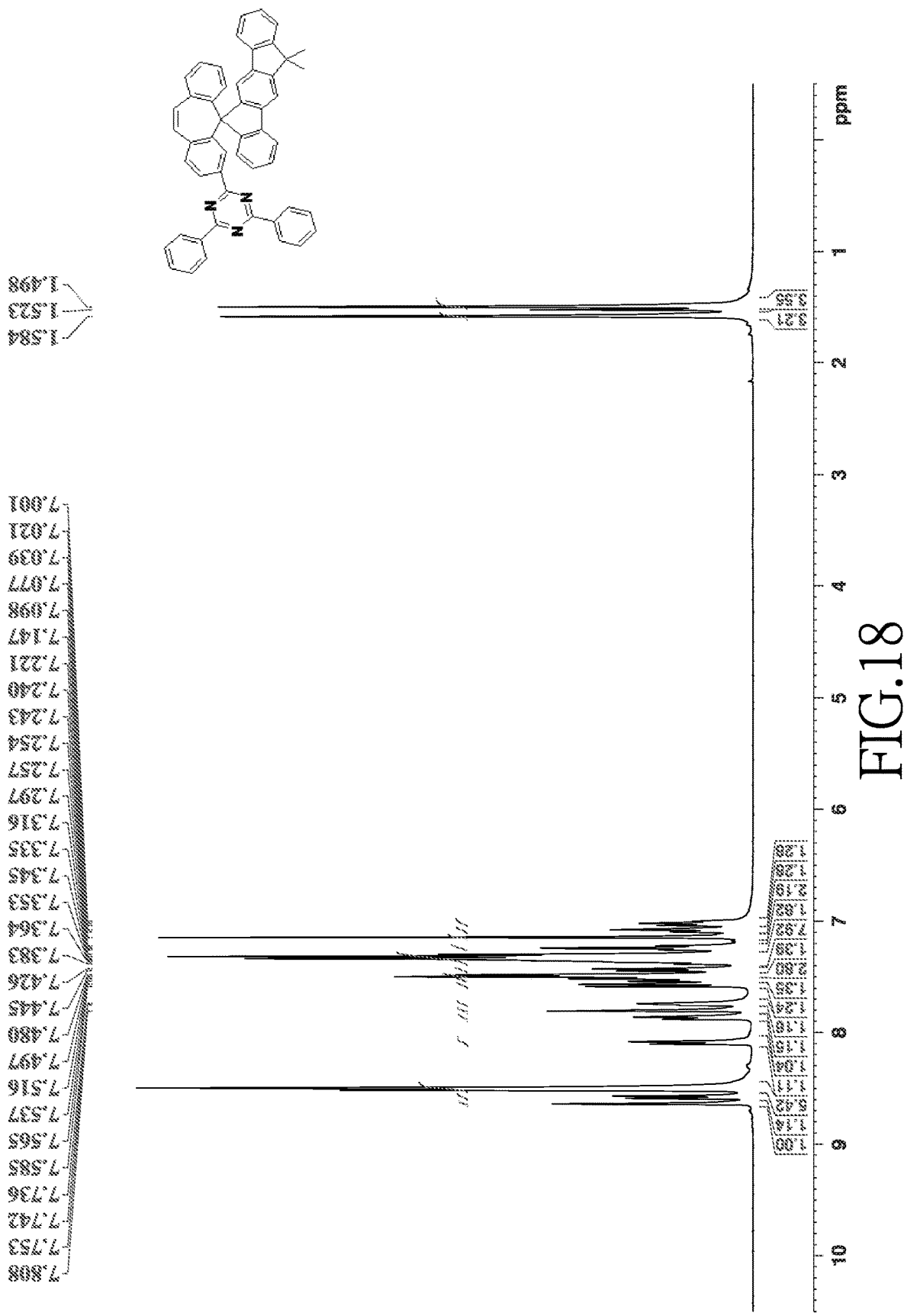
Figure 19:
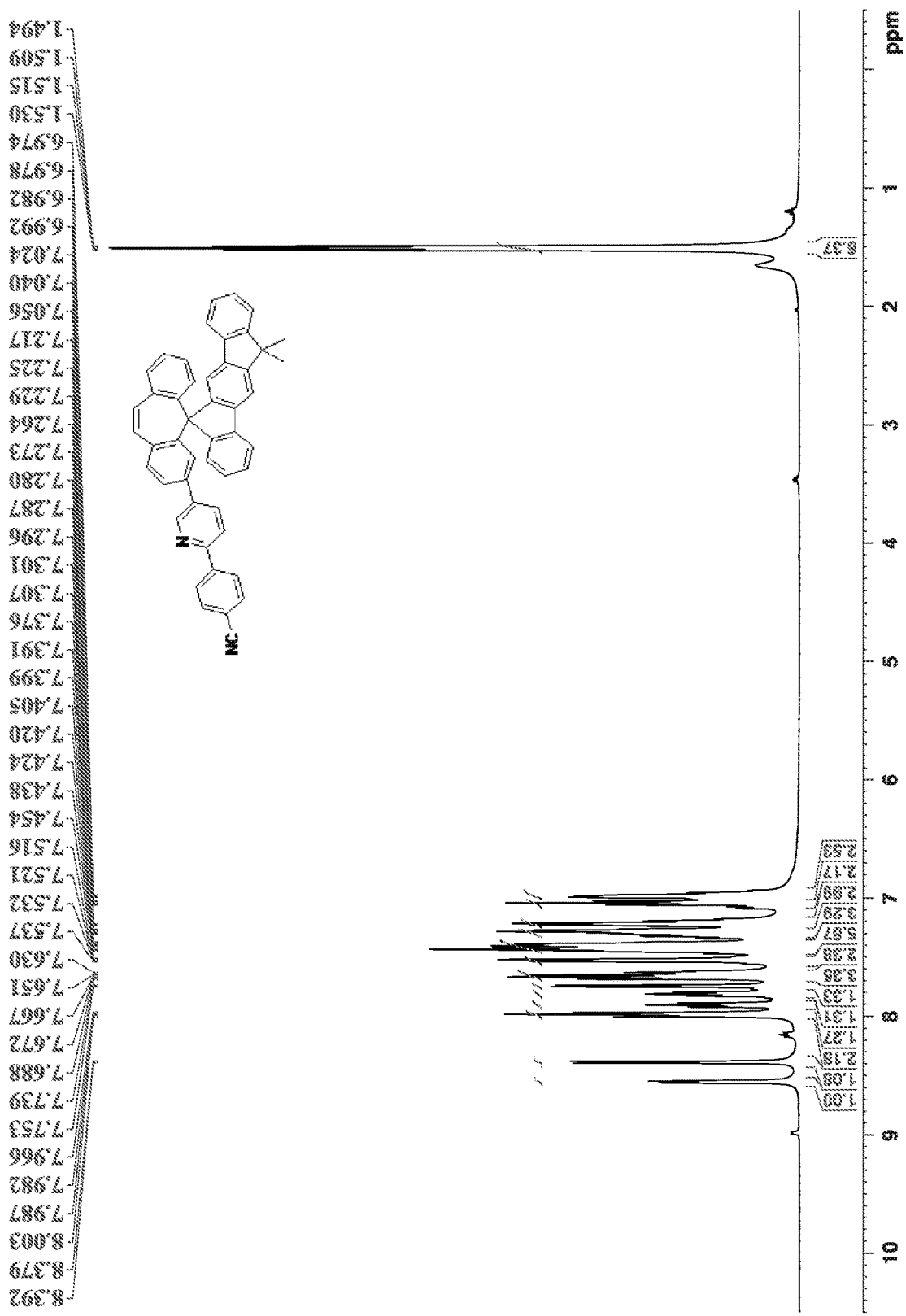

Reactant Bn and Intermediate Cn adopted to synthesize Compounds I to XVIII were listed in Table 5. Compounds I to XVIII were identified by H$^1$-NMR and FD-MS, and the chemical structure, yield, formula and mass of each of Compounds I to XVIII were also listed in Table 5. According to FIGS. 2 to 19 and the results of FD-MS, the chemical structure of Compounds I to XVIII were identified as follows.

TABLE 5 reactants and intermediates adopted to prepare Compounds I to XVIII and their yields, formulae, and FD-MS data.

| | | Claimed Compound | | |
|---|---|---|---|---|
| Intermediate No. | Reactant No. | Chemical Structure | Yield (%) | Formula/ Mass (M$^+$) |
| C1-B | B7 | Compound I | 86 | C$_{46}$H$_{29}$N$_3$/ 623.74 |

TABLE 5-continued reactants and intermediates adopted to prepare Compounds I to XVIII and their yields, formulae, and FD-MS data.

| | | Claimed Compound | | |
|---|---|---|---|---|
| Intermediate No. | Reactant No. | Chemical Structure | Yield (%) | Formula/ Mass (M+) |
| C1 | B1 | Compound II | 91 | $C_{38}H_{23}N$/ 493.60 |
| C1 | B12 | Compound III | 85 | $C_{44}H_{27}N$/ 569.69 |
| C2 | B11 | Compound IV | 84 | $C_{45}H_{26}N_2$/ 594.70 |
| C1-B | B10 | Compound V | 89 | $C_{46}H_{19}D_{10}N_3$/ 633.80 |

TABLE 5-continued reactants and intermediates adopted to prepare Compounds I to XVIII and their yields, formulae, and FD-MS data.

| Intermediate No. | Reactant No. | Chemical Structure (Claimed Compound) | Yield (%) | Formula/ Mass (M+) |
|---|---|---|---|---|
| C3 | B8 | Compound VI | 81 | $C_{50}H_{32}N_2$/ 660.80 |
| C3-B | B4 | Compound VII | 84 | $C_{43}H_{26}N_2$/ 570.68 |
| C8-B | B4 | Compound VIII | 86 | $C_{51}H_{30}N_2$/ 670.80 |
| C8 | B1 | Compound IX | 82 | $C_{46}H_{27}N$/ 593.71 |

TABLE 5-continued reactants and intermediates adopted to prepare Compounds I to XVIII and their yields, formulae, and FD-MS data.

| Intermediate No. | Reactant No. | Chemical Structure | Yield (%) | Formula/ Mass (M+) |
|---|---|---|---|---|
| C9 | B1 | Compound X | 91 | $C_{53}H_{30}N_2$/ 694.82 |
| C5-B | B5 | Compound XI | 80 | $C_{49}H_{30}N_2$/ 646.78 |
| C5-B | B7 | Compound XII | 82 | $C_{50}H_{31}N_3$/ 673.80 |

TABLE 5-continued reactants and intermediates adopted to prepare Compounds I to XVIII and their yields, formulae, and FD-MS data.

| | | Claimed Compound | | |
|---|---|---|---|---|
| Intermediate No. | Reactant No. | Chemical Structure | Yield (%) | Formula/ Mass (M+) |
| C5 | B1 | Compound XIII | 66 | $C_{42}H_{25}N$/ 543.65 |
| C6 | B2 | Compound XIV | 72 | $C_{45}H_{28}N_2$/ 596.72 |
| C7-B | B7 | Compound XV | 67 | $C_{52}H_{31}N_3$/ 697.82 |

TABLE 5-continued reactants and intermediates adopted to prepare Compounds I to XVIII and their yields, formulae, and FD-MS data.

| Intermediate No. | Reactant No. | Chemical Structure | Yield (%) | Formula/ Mass (M+) |
|---|---|---|---|---|
| C7-B | B6 | Compound XVI | 68 | $C_{53}H_{32}N_2$/ 696.83 |
| C4-B | B7 | Compound XVII | 71 | $C_{51}H_{35}N_3$/ 689.84 |
| C4-B | B4 | Compound XVIII | 76 | $C_{48}H_{32}N_2$/ 636.78 |

Modifications of Compounds I to XVIII

In addition to the Compounds I to XVIII, one person skilled in the art can react any Intermediate C, for example, but not limited to, the foresaid Intermediate Cn or Cn-B, with any Reactant Bn through a reaction mechanism similar to Scheme I to synthesize other desired claimed novel compounds.

Preparation of OLED devices

A glass substrate coated with ITO layer (abbreviated as ITO substrate) in a thickness of 1500 Å was placed in distilled water containing a detergent dissolved therein, and was ultrasonically washed. The detergent was a product manufactured by Fischer Co., and the distilled water was distilled water filtered twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED devices of Examples 1 to 40. The vacuum degree during the deposition was maintained at $1\times10^{-6}$ to $3\times10^{-7}$ torr. Herein, the ITO substrate was deposited with a first hole injection layer (HIL-1), a second hole injection layer (HIL-2), a first hole transporting layer (HTL-1), a second hole transporting layer (HTL-2), a blue/green/red emission layer (BEL/GEL/REL), an electron transporting layer (ETL), an electron injection layer (EIL), and a cathode (Cthd).

Herein, HAT was a material for forming HIL-1 and HIL-2; HI-2 was a material for forming HIL-1, HIL-2, and HTL-1; HI-D was a material for forming HIL-1, HT-1 and HT-2 were respectively materials for forming HTL-1 and HTL-2; novel compounds of the present invention and commercial ETs (BCP and TAZ) were materials for forming ETL; Liq was a material for forming ETD and EIL. RH-1 or RH-2/GH-1 or GH-2/BH were host material for forming REL/GEL/BEL, and RD/GD/BD-1 or BD-2 were dopants for forming REL/GEL/BEL. The main difference of the OLEDs between the Example and Comparative Example was that the ETL of OLED in the following comparative examples was made of BCP or TAZ, but the ETL of OLED in following examples was made of the novel compounds of the present invention as listed in Table 5. The detailed chemical structures of foresaid commercial materials were listed in Table 6.

TABLE 6 chemical structures of commercial materials for OLED devices.

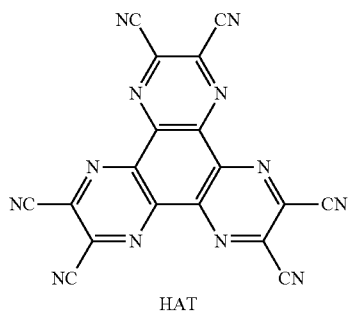 [SMILES: N#Cc1nc2c3nc(C#N)c(C#N)nc3c3nc(C#N)c(C#N)nc3c2nc1C#N ; "HAT"]

HAT

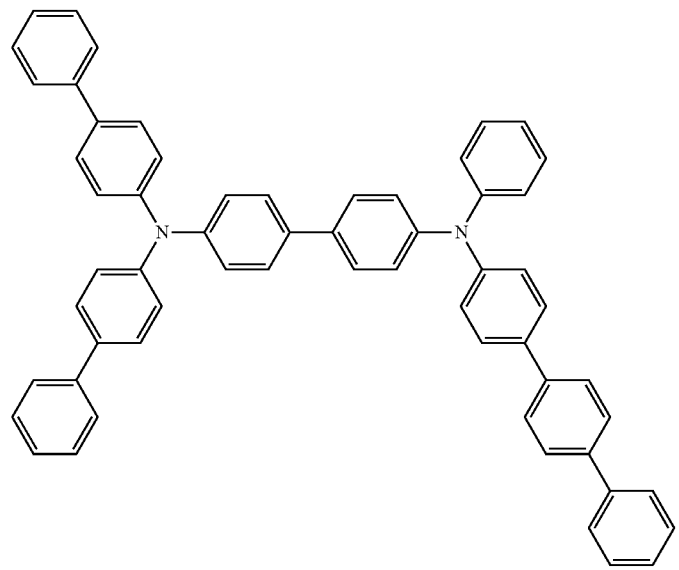

HI-2

TABLE 6-continued
chemical structures of commercial materials for OLED devices.
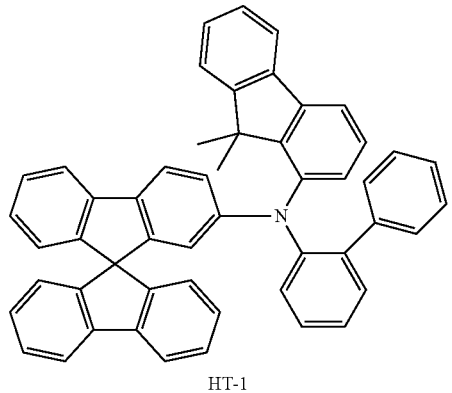
HT-1
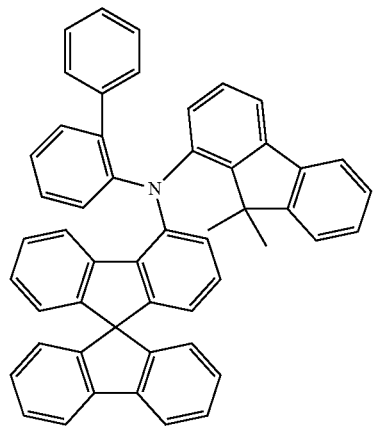
HT-2
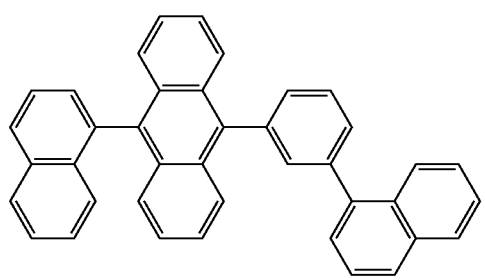
BH
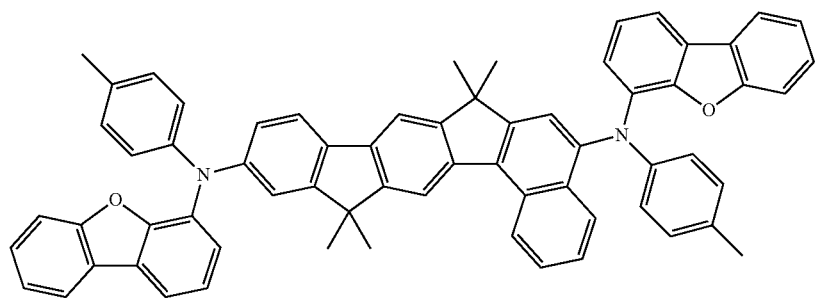
BD-1

TABLE 6-continued
chemical structures of commercial materials for OLED devices.
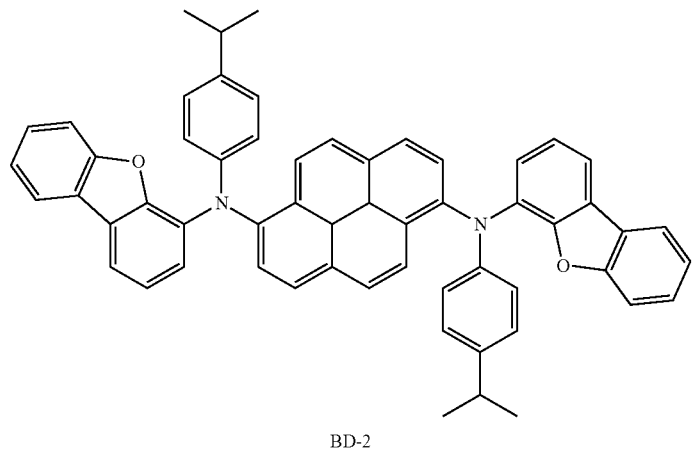 [SMILES: CC(C)c1ccc(N(C2=CC=C3C=CC4=C(N(c5ccc(C(C)C)cc5)c5cccc6c5oc5ccccc56)C=CC5=CC=C2C3C54)c2cccc3c2oc2ccccc23)cc1 ; "BD-2"]
BD-2
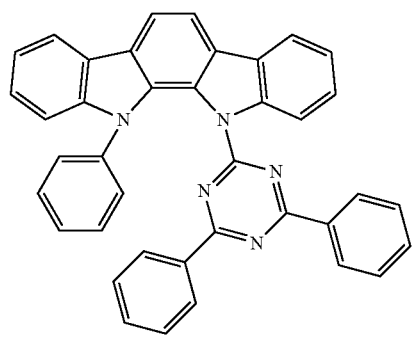
GH-1
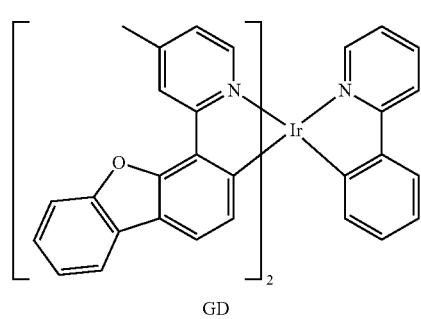
GD
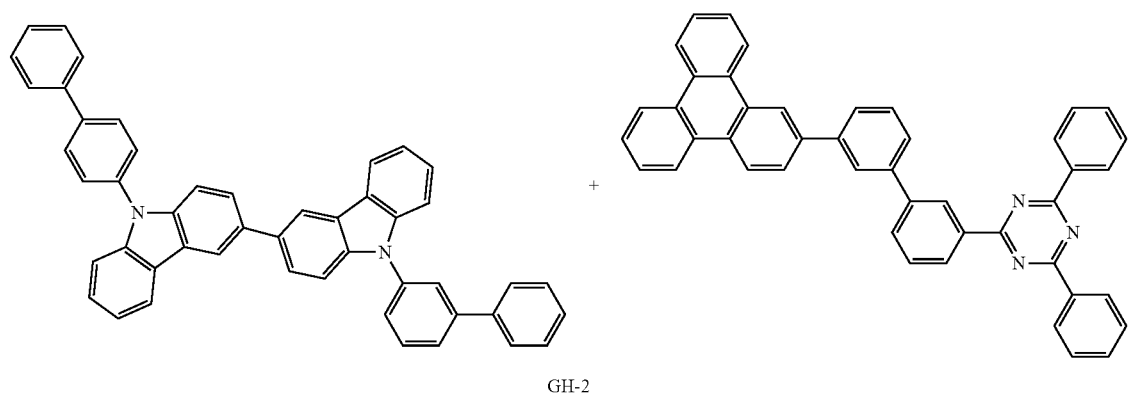 [SMILES: c1ccc(-c2ccc(-n3c4ccccc4c4cc(-c5ccc6c(c5)c5ccccc5n6-c5cccc(-c6ccccc6)c5)ccc43)cc2)cc1 ; c1ccc(-c2nc(-c3ccccc3)nc(-c3cccc(-c4cccc(-c5ccc6c7ccccc7c7ccccc7c6c5)c4)c3)n2)cc1]
GH-2

TABLE 6-continued
chemical structures of commercial materials for OLED devices.
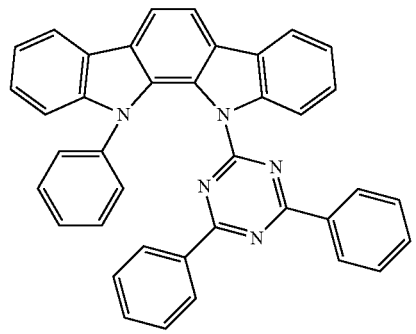
RH-1
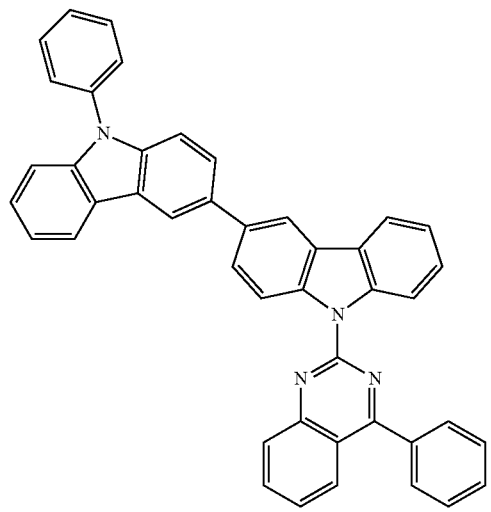
RH-2
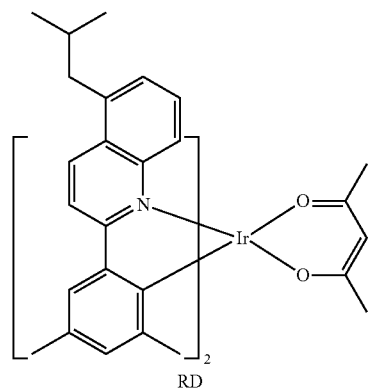
RD
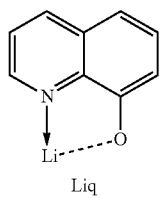
Liq TABLE 6-continued chemical structures of commercial materials for OLED devices.

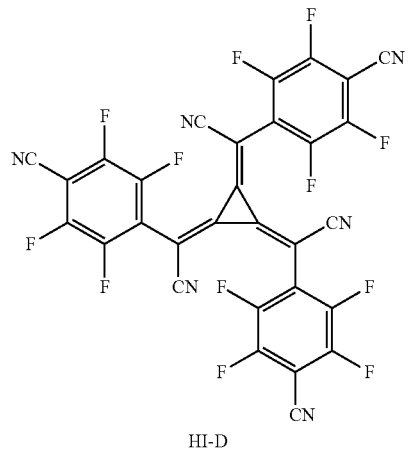 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F ; "HI-D"]

HI-D

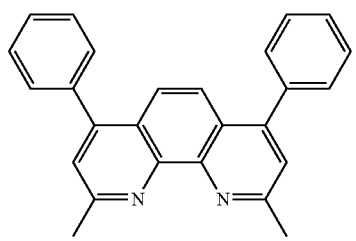

BCP
(commercial ET)

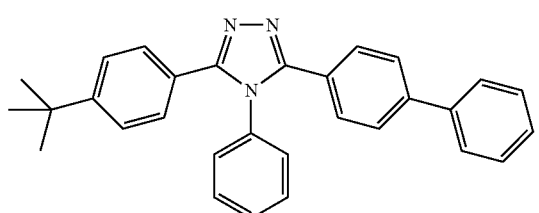

TAZ
(commercial ET)

Preparation of Red OLED Devices

To prepare red OLED devices, multiple organic layers were respectively deposited on the ITO substrate according to the sequence as listed in Table 7 to prepare first red OLED devices and second red OLED devices. The materials and the thicknesses of the organic layers in the first and second red OLED devices were also listed in Table 7. The difference between the first and the second red OLED devices is the materials of HIL-1, HIL-2, HTL-1, and REL as listed in Table 7.

TABLE 7 coating sequence, materials and thickness of the organic layers in the first and second red OLED devices.

| Coating Sequence | Layer | Material | | Thickness |
|---|---|---|---|---|
| | | First red OLED device | Second red OLED device | |
| 1 | HIL-1 | HAT | HI-2 doped with 3.0 wt % of HI-D | 100 Å |
| 2 | HIL-2 | HI-2 doped with 5.0 wt % of HAT | HI-2 | 2100 Å |
| 3 | HTL-1 | HT-1 | HI-2 | 100 Å |
| 4 | HTL-2 | HT-2 | HT-2 | 100 Å |
| 5 | REL | RH-1 doped with 3.5 wt % of RD | RH-2 doped with 3.5 wt % of RD | 300 Å |
| 6 | ETL | Commercial ET/novel compounds doped with 35.0 wt % of Liq | Commercial ET/novel compounds doped with 35.0 wt % of Liq | 350 Å |
| 7 | EIL | Liq | Liq | 15 Å |
| 8 | Cthd | Al | Al | 1500 Å |

Preparation of Green OLED Devices

To prepare the green OLED devices, multiple organic layers were respectively deposited on the ITO substrate according to the sequence as listed in Table 8 to prepare first green OLED devices and second green OLED devices. The materials and the thicknesses of the organic layers in the first and second green OLED devices were also listed in Table 8. The difference between the first and the second green OLED devices is the materials of HIL-1, HIL-2, HTL-1, and GEL as listed in Table 8.

TABLE 8 coating sequence, materials and thickness of the layers in the first and second green OLED devices.

| Coating Sequence | Layer | First green OLED device | Second green OLED device | Thickness |
|---|---|---|---|---|
| 1 | HIL-1 | HAT | HI-2 doped with 3.0 wt % of HI-D | 100 Å |
| 2 | HIL-2 | HI-2 doped with 5.0 wt % of HAT | HI-2 | 1300 Å |
| 3 | HTL-1 | HT-1 | HI-2 | 100 Å |
| 4 | HTL-2 | HT-2 | HT-2 | 100 Å |
| 5 | GEL | GH-1 doped with 10.0 wt % of GD | GH-2 doped with 10.0 wt % of GD | 300 Å |
| 6 | ETL | Commercial ET/novel compounds doped with 35.0 wt % of Liq | Commercial ET/novel compounds doped with 35.0 wt % of Liq | 350 Å |
| 7 | EIL | Liq | Liq | 15 Å |
| 8 | Cthd | Al | Al | 1500 Å |

Preparation of Blue OLED Devices

To prepare the blue OLED devices, multiple organic layers were respectively deposited on the ITO substrate according to the sequence as listed in Table 9 to prepare first blue OLED devices and second blue OLED devices. The materials and the thicknesses of the organic layers in the first and second blue OLED devices were also listed in Table 9. The difference between the first and the second blue OLED devices is the materials of HIL-1, HIL-2, HTL-1, and BEL as listed in Table 9.

TABLE 9 coating sequence, materials and thickness of the layers in the first and second blue OLED device.

| Coating Sequence | Layer | First blue OLED device | Second blue OLED device | Thickness |
|---|---|---|---|---|
| 1 | HIL-1 | HAT | HI-2 doped with 3.0 wt % of HI-D | 100 Å |
| 2 | HIL-2 | HI-2 doped with 5.0 wt % of HAT | HI-2 | 750 Å |
| 3 | HTL-1 | HT-1 | HI-2 | 100 Å |
| 4 | HTL-2 | HT-2 | HT-2 | 100 Å |
| 5 | BEL | BH doped with 3.5 wt % of BD-1 | BH doped with 3.5 wt % of BD-2 | 300 Å |
| 6 | ETL | Commercial ET/novel compounds doped with 35.0 wt % of Liq | Commercial ET/novel compounds doped with 35.0 wt % of Liq | 350 Å |
| 7 | EIL | Liq | Liq | 15 Å |
| 8 | Cthd | Al | Al | 1500 Å |

Performance of OLED Device

To evaluate the performance of OLED devices, red, green, and blue OLED devices were measured by PR650 as photometer and Keithley 2400 as power supply. Color coordinates (x,y) were determined according to the CIE chromaticity scale (Commission Internationale de L'Eclairage, 1931). The results were shown in Table 10. For the blue and red OLED devices, the data were collected at 1000 nits. For the green OLED devices, the data were collected at 3000 nits.

The materials of ETL, color and data of CIE, driving voltage, and current efficiency of Examples 1 to 40 (E1 to E40) and Comparative Examples 1 to 6 (C1 to C6) were listed in Table 10. As listed in Table 10, the first blue OLED devices were named as B1, and the second blue OLED devices were named as B2. Similarly, the first and second red OLED devices and the first and second green OLED devices were respectively named as R1, R2, G1, and G2.

TABLE 10 materials of ETL, characteristics and performance of OLED devices of Examples 1 to 40 and Comparative Examples 1 to 6.

| Example No. | Material of ETL | OLED Device No. | CIE (x, y) | Voltage (V) | Current Efficiency (cd/A) |
|---|---|---|---|---|---|
| E1 | Compound II | B1 | (0.136, 0.172) | 3.7 | 8.55 |
| E2 | Compound III | B1 | (0.136, 0.189) | 3.59 | 8.97 |
| E3 | Compound IV | B1 | (0.137, 0.191) | 4.25 | 9.1 |
| E4 | Compound IX | B1 | (0.136, 0.175) | 3.82 | 12.5 |
| E5 | Compound XIII | B1 | (0.136, 0.17) | 3.63 | 8.54 |
| E6 | Compound I | B2 | (0.129, 0.164) | 4.53 | 8.08 |
| E7 | Compound II | B2 | (0.103, 0.159) | 3.67 | 7.98 |
| E8 | Compound III | B2 | (0.130, 0.161) | 3.64 | 6.7 |
| E9 | Compound V | B2 | (0.129, 0.165) | 4.49 | 8.21 |
| E10 | Compound VI | B2 | (0.103, 0.155) | 4.73 | 7.67 |
| E11 | Compound VIII | B2 | (0.129, 0.159) | 4.31 | 8.8 |
| E12 | Compound X | B2 | (0.129, 0.168) | 4.66 | 7.22 |
| E13 | Compound XI | B2 | (0.129, 0.156) | 4.33 | 8.83 |
| E14 | Compound XII | B2 | (0.129, 0.16) | 4.52 | 8.17 |
| E15 | Compound XIV | B2 | (0.13, 0.154) | 3.72 | 6.84 |
| E16 | Compound XVII | B2 | (0.129, 0.164) | 4.58 | 8.17 |
| E17 | Compound XVIII | B2 | (0.13, 0.165) | 6.15 | 6.6 |
| C1 | BCP | B1 | (0.130, 0.170) | 6.35 | 7.05 |
| C2 | TAZ | B2 | (0.131, 0.174) | 7.84 | 6.55 |
| E18 | Compound II | G1 | (0.309, 0.640) | 3.02 | 66.2 |
| E19 | Compound IV | G1 | (0.316, 0.638) | 3.2 | 66.1 |
| E20 | Compound IX | G1 | (0.312, 0.64) | 3.31 | 70.3 |
| E21 | Compound XIII | G1 | (0.311, 0.64) | 3 | 66.5 |
| E22 | Compound I | G2 | (0.320, 0.635) | 4.22 | 78.5 |
| E23 | Compound III | G2 | (0.311, 0.64) | 3.14 | 62.4 |
| E24 | Compound V | G2 | (0.331, 0.628) | 4.32 | 76.2 |
| E25 | Compound VIII | G2 | (0.321, 0.634) | 4.35 | 71.2 |
| E26 | Compound X | G2 | (0.325, 0.632) | 4.51 | 68.8 |
| E27 | Compound XI | G2 | (0.319, 0.636) | 4.43 | 74.9 |
| E28 | Compound XII | G2 | (311, 0.64) | 3.87 | 72.8 |
| E29 | Compound XIV | G2 | (0.323, 0.633) | 4.04 | 72.6 |
| E30 | Compound XVII | G2 | (0.327, 0.63) | 4.36 | 73.4 |
| E31 | Compound XVIII | G2 | (0.323, 0.63) | 6.11 | 51.9 |
| C3 | BCP | G1 | (0.313, 0.638) | 5.27 | 65.3 |
| C4 | TAZ | G2 | (0.325, 0.628) | 8.36 | 48.4 |
| E32 | Compound II | R1 | (0.660, 0.339) | 3.12 | 22.4 |
| E33 | Compound IV | R1 | (0.661, 0.337) | 3.27 | 21.4 |
| E34 | Compound IX | R1 | (0.662, 0.337) | 3.16 | 21.1 |
| E35 | Compound XIII | R1 | (0.661, 0.337) | 3.16 | 21.9 |
| E36 | Compound I | R2 | (0.657, 0.341) | 3.97 | 29.2 |
| E37 | Compound III | R2 | (0.657, 0.341) | 3.23 | 22.1 |
| E38 | Compound V | R2 | (0.658, 0.34) | 4.01 | 29.3 |
| E39 | Compound XI | R2 | (0.656, 0.341) | 4.26 | 28.6 |
| E40 | Compound XII | R2 | (0.657, 0.34) | 4.04 | 29.2 |
| C5 | BCP | R1 | (0.659, 0.340) | 4.16 | 20.10 |
| C6 | TAZ | R2 | (0.648, 0.342) | 11.38 | 21.04 |

Based on the results, in comparison with the commercial electron transport materials (BCP and TAZ), adopting Compounds I to XVIII as the electron transport material can reduce the driving voltage and improve the current efficiency of the red, green, or blue OLEDs. It demonstrated that the novel compound of the present invention is suitable as an electron transport material for any color OLEDs, and allows the OLEDs using the same to have low driving voltage and improved current efficiency.

Even though numerous characteristics and advantages of the present invention have been set forth in the foregoing description, together with details of the structure and features of the invention, the disclosure is illustrative only. Changes may be made in the details, especially in matters of quantity, position, and arrangement of substitution groups within the principles of the invention to the full extent indicated by the broad general meaning of the terms in which the appended claims are expressed.

What is claimed is:

1. A compound represented by the following Formula (I):

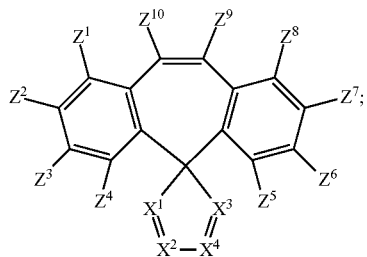

Formula (I)

wherein X¹ and X² are each independently C(Rᵃ), the two (Rᵃ)s are the same or different, and the two (Rᵃ)s are joined together to form an aryl ring;

wherein X³ and X⁴ are each independently C(Rᵇ), the two (Rᵇ)s are the same or different, and the two (Rᵇ)s are joined together to form a polycyclic aromatic ring;

wherein $Z^1$ to $Z^{10}$ are each independently selected from the group consisting of: a hydrogen atom, a deuterium atom, a trifluoromethyl group, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 carbon atoms, an alkylboron group having 1 to 40 carbon atoms, an arylboron group having 6 to 60 ring carbon atoms, a phosphine group having 1 to 40 carbon atoms, and a phosphine oxide group having 1 to 40 carbon atoms.

2. The compound as claimed in claim 1, wherein the polycyclic aromatic ring extended from X³ and X⁴ is selected from the group consisting of: a substituted or unsubstituted naphthalene ring, a substituted or unsubstituted anthracene ring, a substituted or unsubstituted phenanthrene ring, a substituted or unsubstituted fluorene ring, a substituted or unsubstituted pyrene ring, a substituted or unsubstituted benzophenanthrene ring, a substituted or unsubstituted benzopyrene ring, a substituted or unsubstituted fluoranthene ring, and a substituted or unsubstituted benzofluoranthene ring.

3. The compound as claimed in claim 1, wherein the compound is represented by

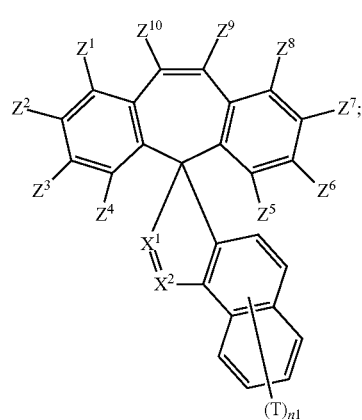

Formula (I-I)

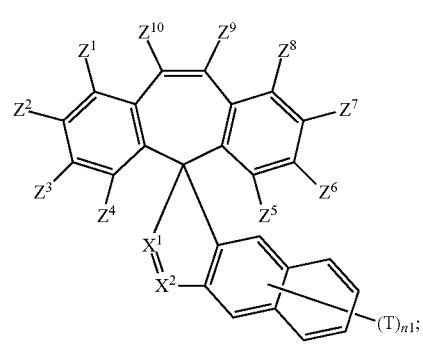

Formula (I-II)

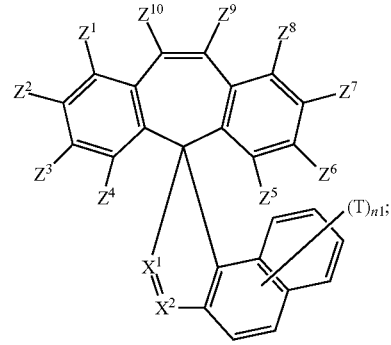

Formula (I-III)

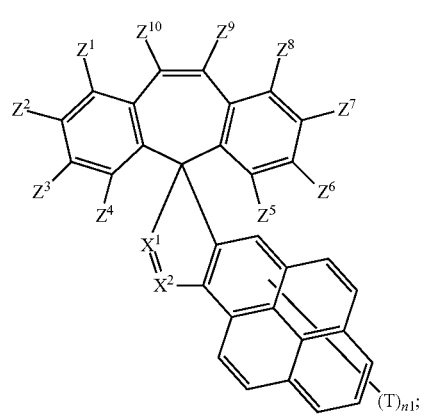

Formula (I-IV)

-continued
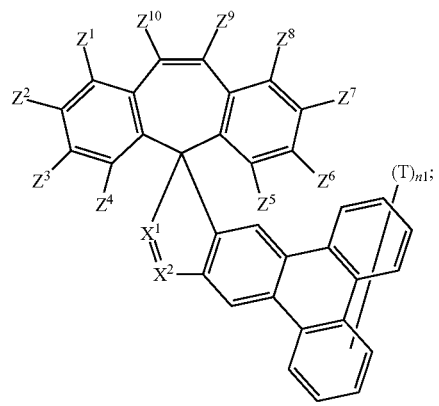
Formula (I-V)
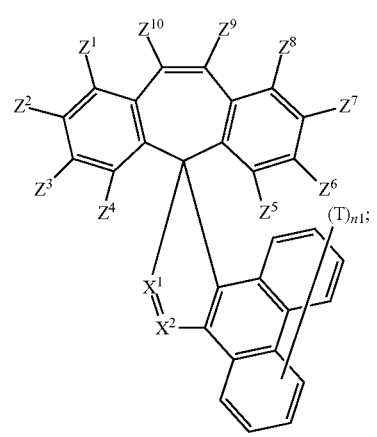
Formula (I-VI)
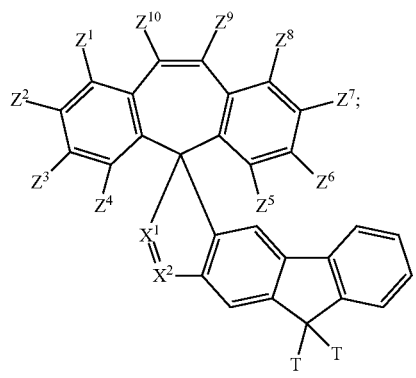
Formula (I-VII)
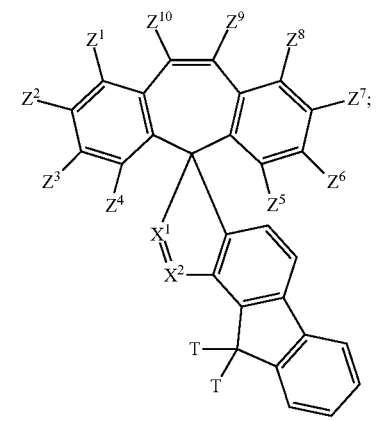
Formula (I-VIII)
-continued
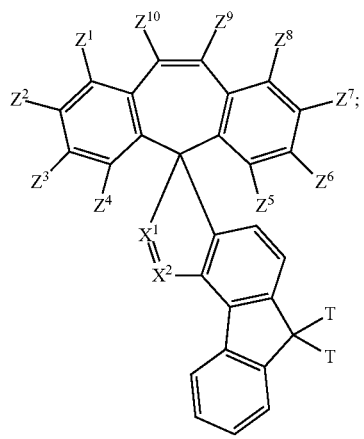
Formula (I-IX)
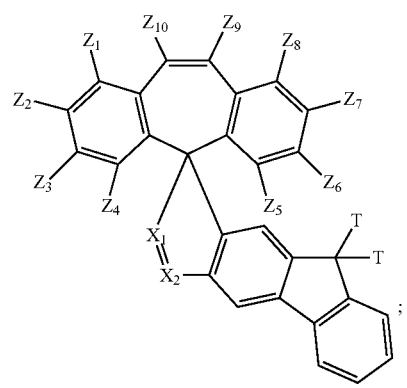
Formula (I-X)
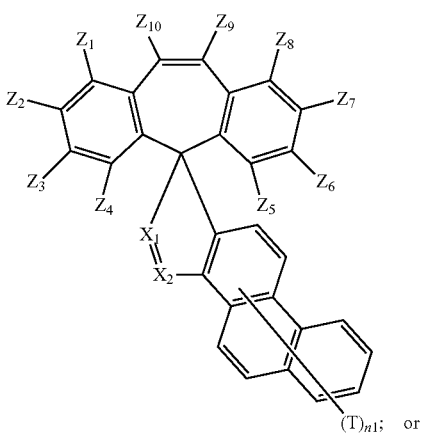
Formula (I-XI)

-continued

Formula (I-XII)

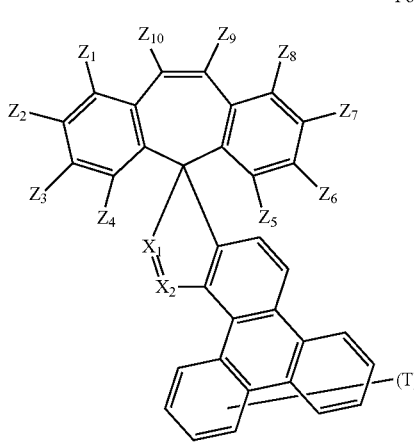

wherein n1 is a positive integral from 0 to 4, T is selected from the group consisting of: a hydrogen atom, a deuterium atom, a methyl group, an ethyl group, a propyl group, a butyl group, a pentyl group, a hexyl group, and a phenyl group.

4. The compound as claimed in claim 1, wherein the aryl ring extended from $X^1$ and $X^2$ is a substituted or unsubstituted 6 to 60-membered carbon ring.

5. The compound as claimed in claim 4, wherein the substituted or unsubstituted 6 to 60-membered carbon ring is selected from the group consisting of: a substituted or unsubstituted benzene ring, a substituted or unsubstituted naphthalene ring, a substituted or unsubstituted anthracene ring, a substituted or unsubstituted phenanthrene ring, a substituted or unsubstituted flourene ring, a substituted or unsubstituted pyrene ring, a substituted or unsubstituted benzophenanthrene ring, a substituted or unsubstituted benzopyrene ring, a substituted or unsubstituted fluoranthene ring, and a substituted or unsubstituted benzofluoranthene ring.

6. The compound as claimed in claim 4, wherein the substituted or unsubstituted 6 to 60-membered carbon ring is a substituted or unsubstituted benzene ring.

7. The compound as claimed in claim 1, wherein at least one of $Z^1$ to $Z^8$ in formula (I) is selected from the group consisting of: an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an aryl group having 6 to 60 ring carbon atoms and substituted with at least one functional group, a heteroaryl group having 3 to 60 ring carbon atoms containing at least one nitrogen atom, an alkoxy group having 1 to 40 carbon atoms and substituted with at least one functional group, an aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to 40 carbon atoms and substituted with at least one functional group, an arylboron group having 6 to 60 ring carbon atoms, a phosphine group having 1 to 40 ring carbon atoms and substituted with at least one functional group, and a phosphine oxide group having 1 to 40 carbon atoms and substituted with at least one functional group, wherein said functional group is selected from the group consisting of: a cyano group, a nitro group, a trifluoromethyl group, a fluoro group, and a chloro group.

8. The compound as claimed in claim 1, wherein at least one of $Z^1$ to $Z^8$ in Formula (I) is selected from the group consisting of:

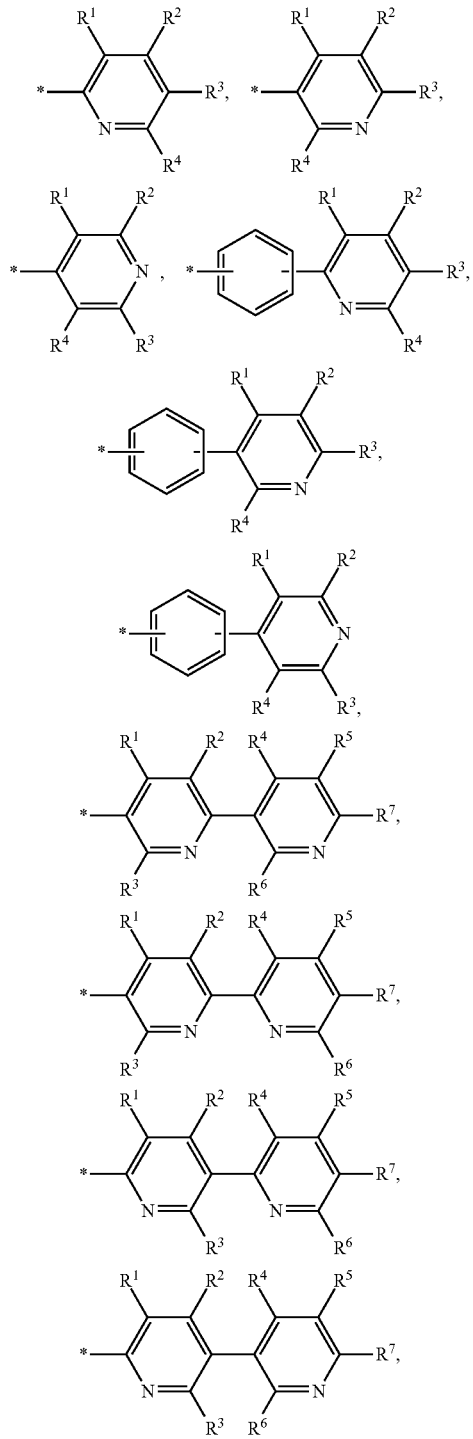

-continued
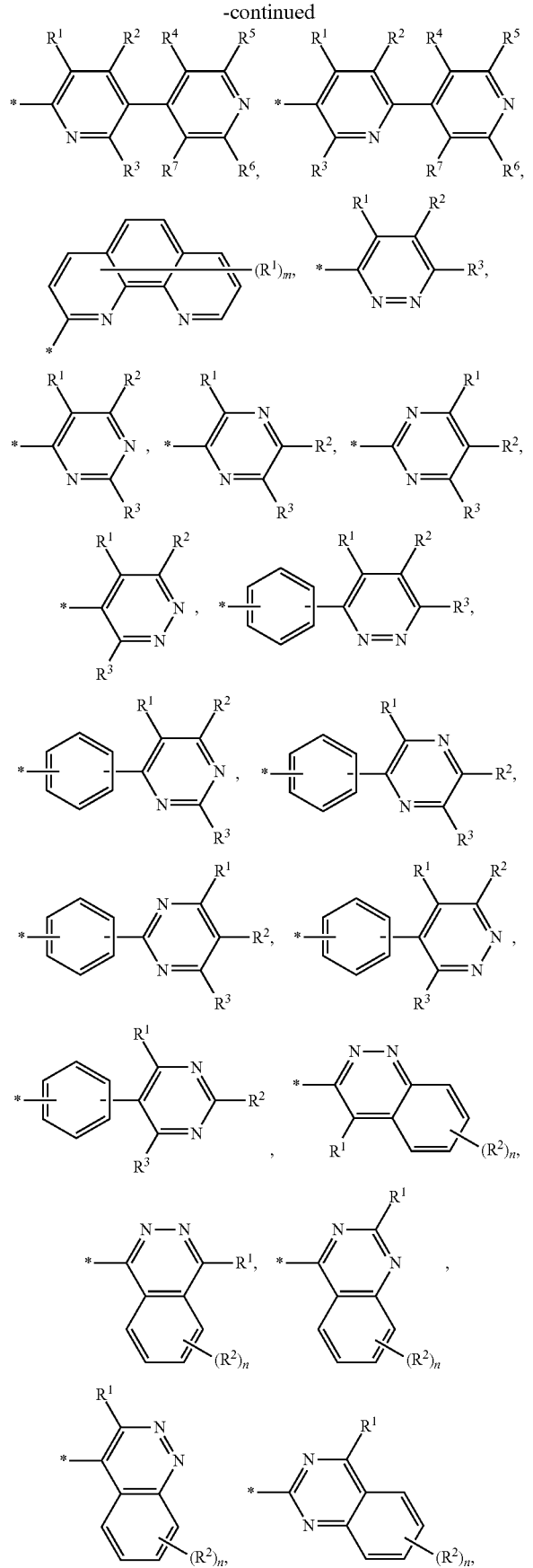
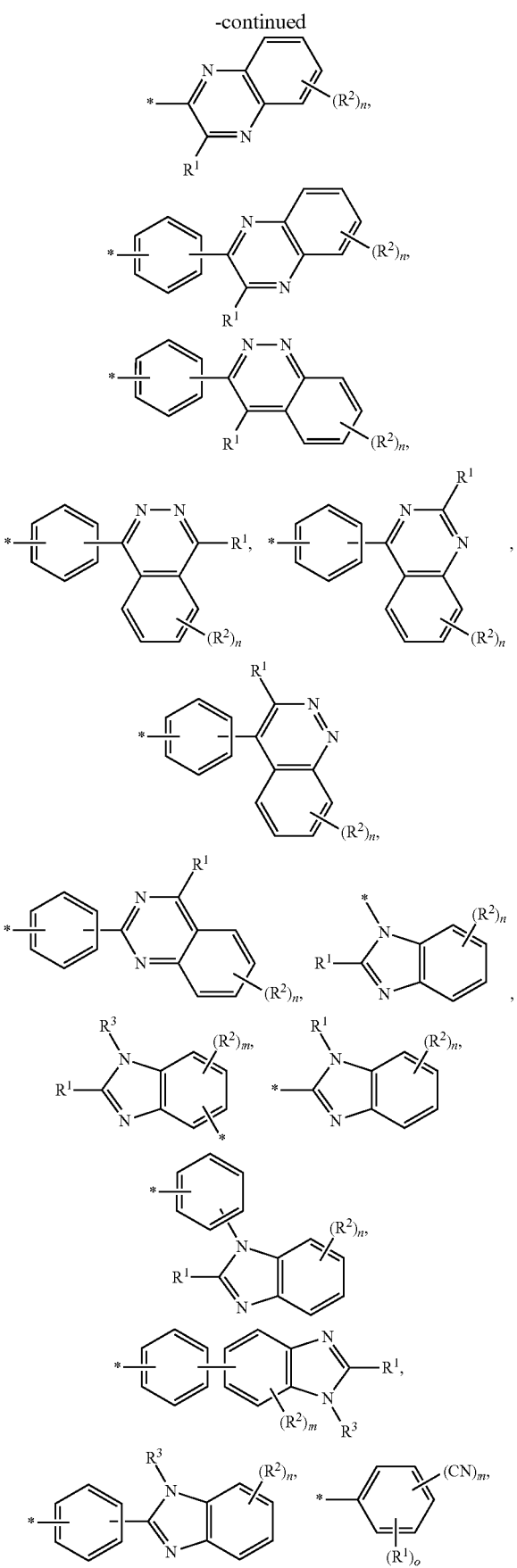

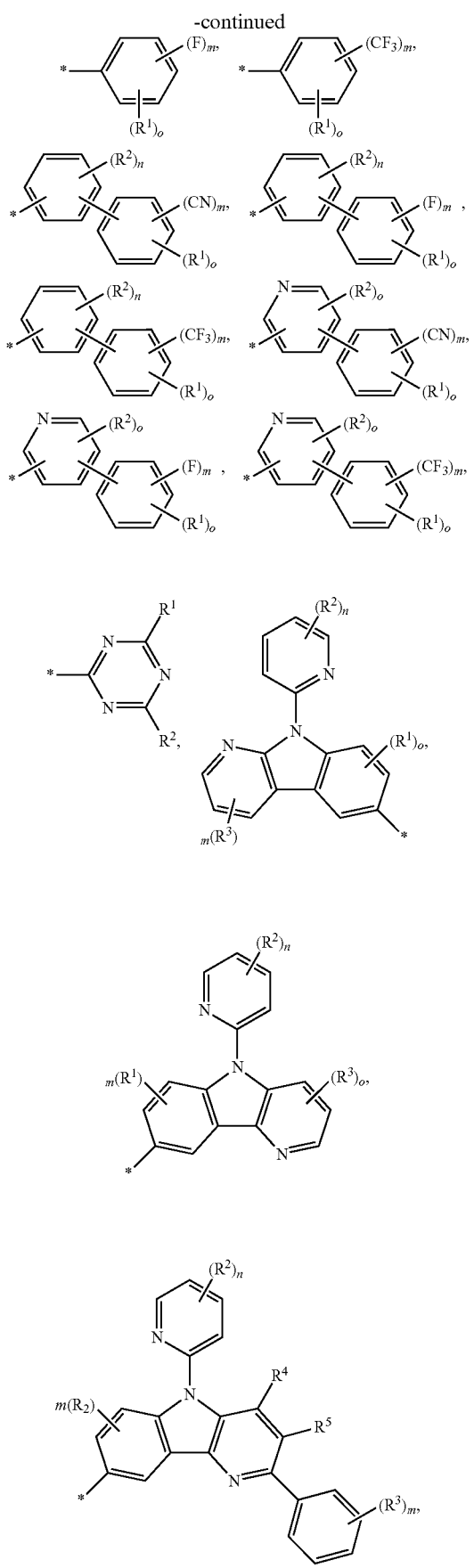

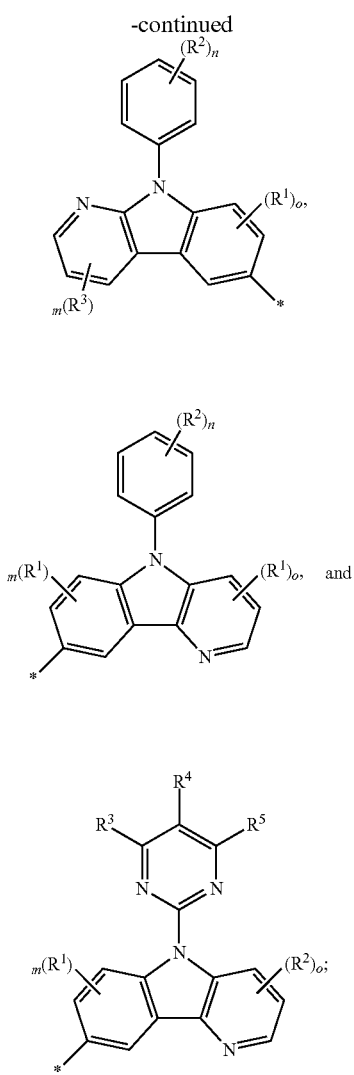

wherein $R^1$ to $R^7$ are each independently selected from the group consisting of: a hydrogen atom, a deuterium atom, a trifluoromethyl group, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 30 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

n is a positive integral from 0 to 4, m is a positive integral from 0 to 3, o is a positive integral from 0 to 3, and the total of m and o is not more than 5.

9. The compound as claimed in claim 1, wherein at least one of $Z^2$, $Z^3$, $Z^6$, and $Z^7$ in Formula (I) is selected from the group consisting of:

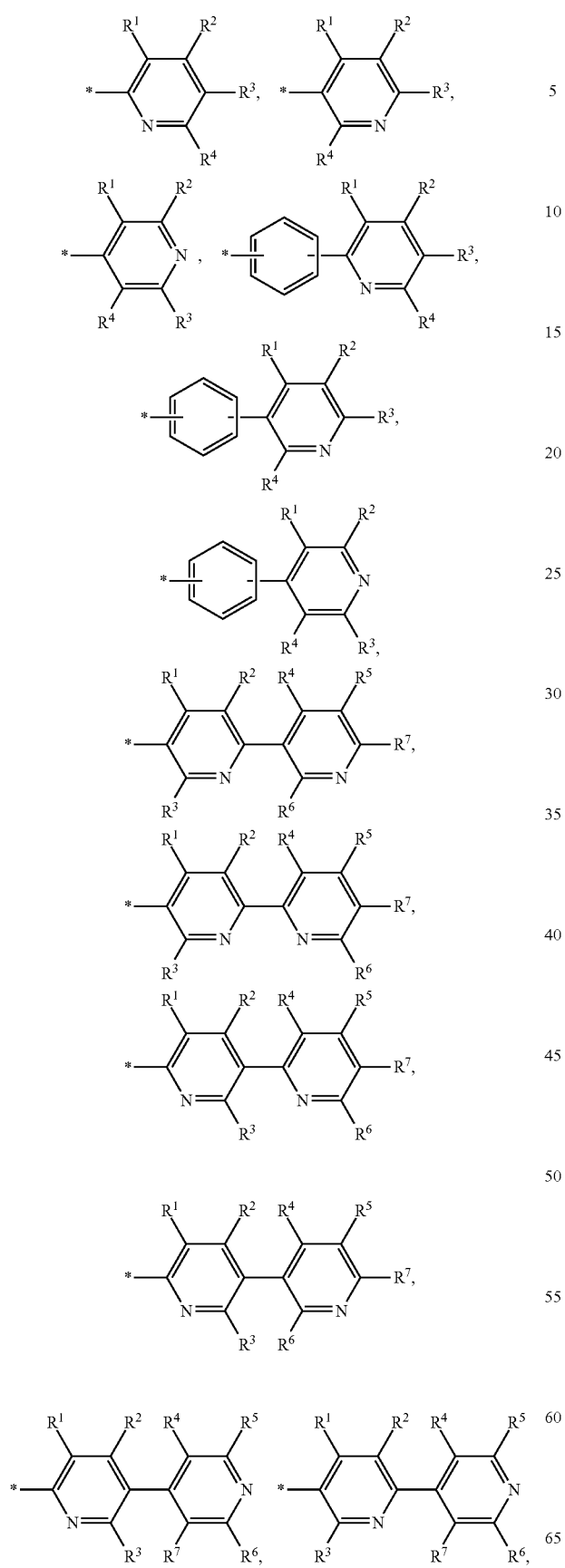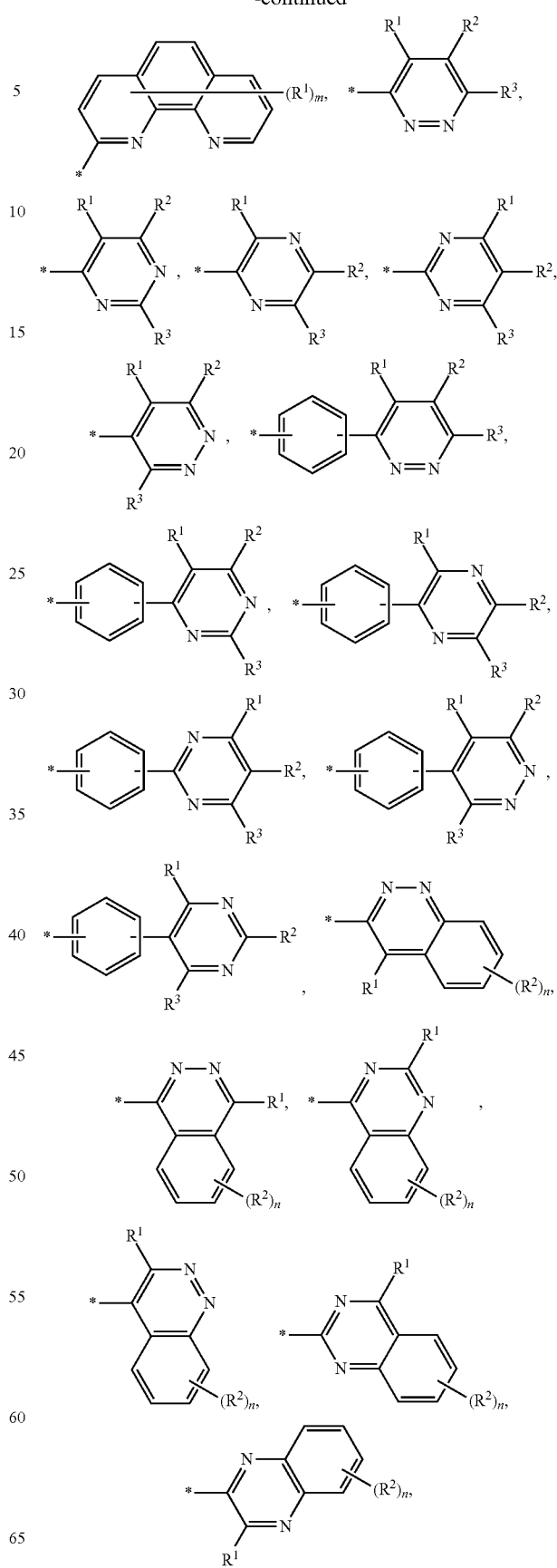

-continued
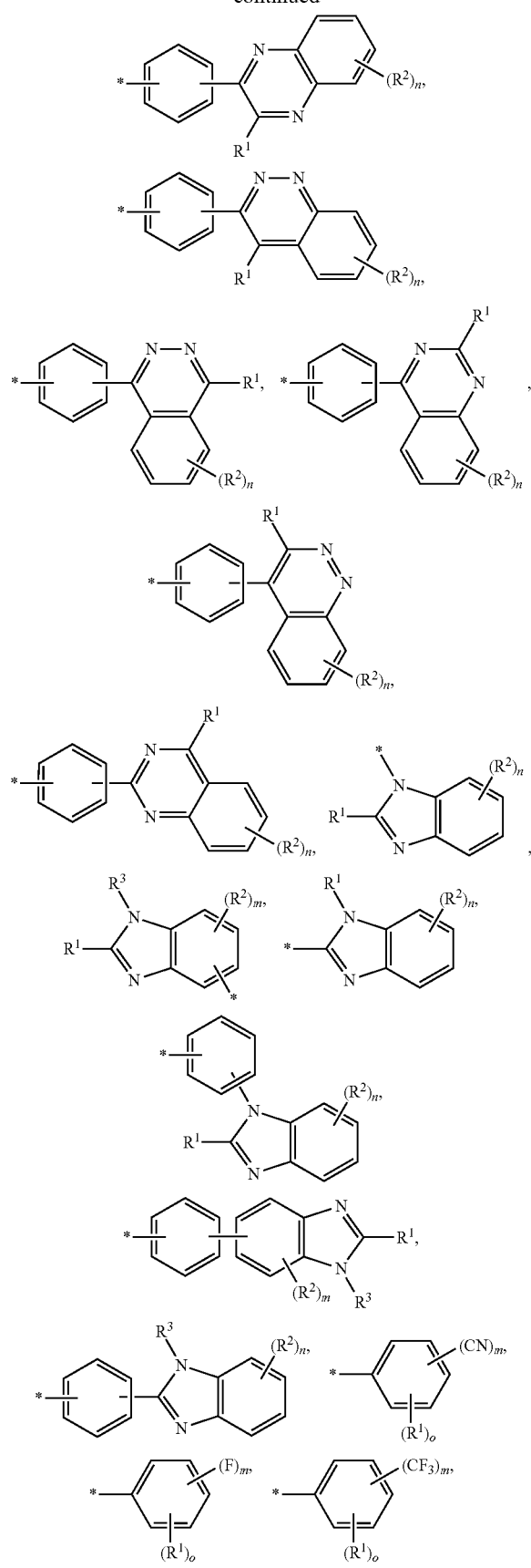
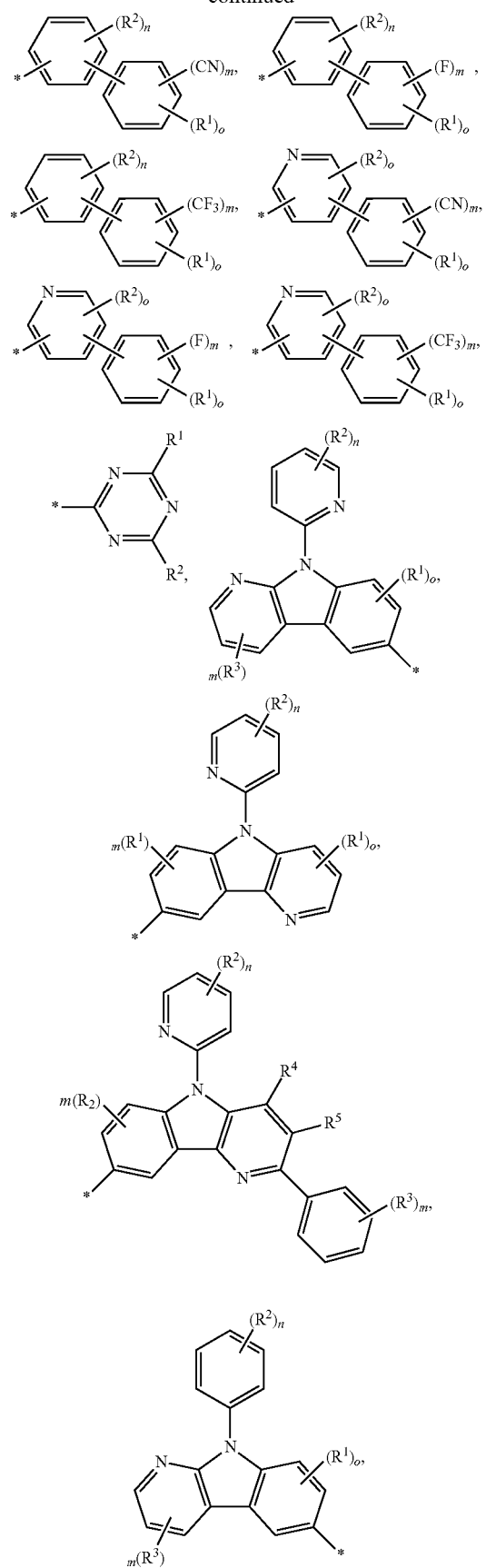

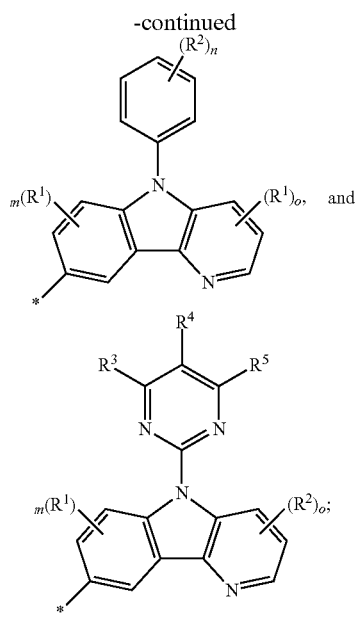

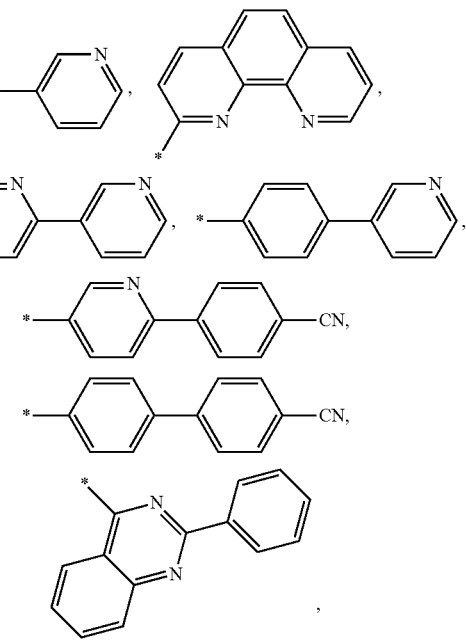

wherein R¹ to R⁷ are each independently selected from the group consisting of: a hydrogen atom, a deuterium atom, a trifluoromethyl group, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

n is a positive integral from 0 to 4, m is a positive integral from 0 to 3, o is a positive integral from 0 to 3, and the total of m and o is not more than 5;

$Z^1$, $Z^4$, $Z^5$, $Z^8$ are each independently selected from the group consisting of: a hydrogen atom, a deuterium atom, an alkyl group having 1 to 12 carbon atoms, an alkenyl group having 2 to 12 carbon atoms, and an alkynyl group having 2 to 12 carbon atoms.

10. The compound as claimed in claim 1, wherein at least one of $Z^2$, $Z^3$, $Z^6$, and $Z^7$ in Formula (I) is selected from the group consisting of:

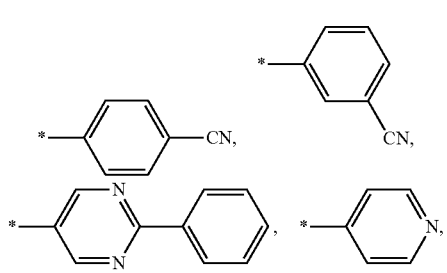

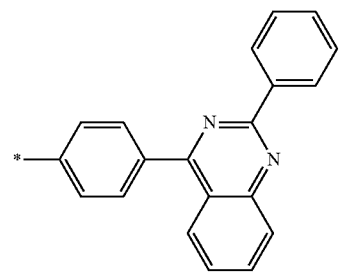

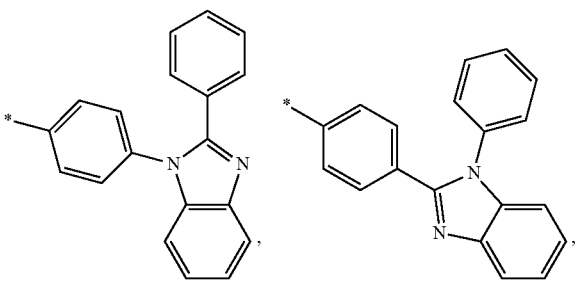

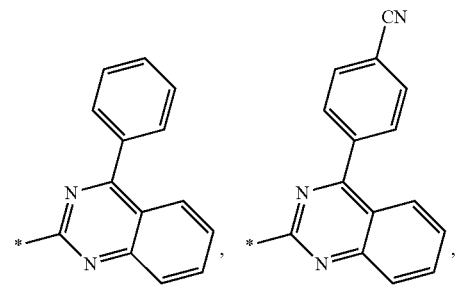

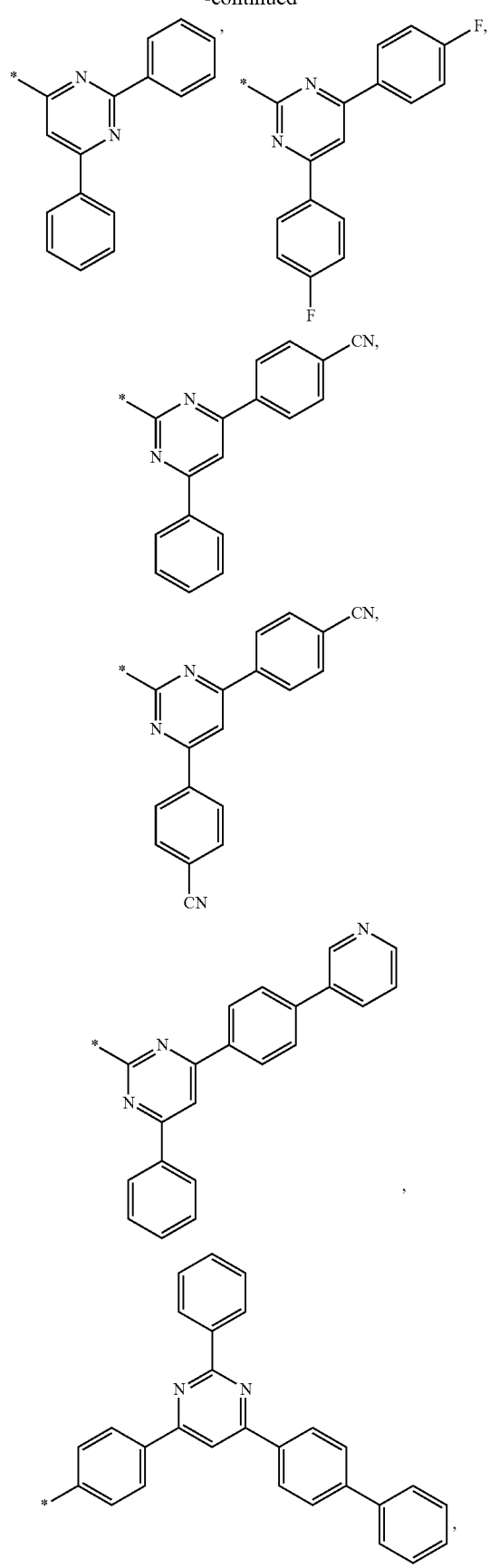
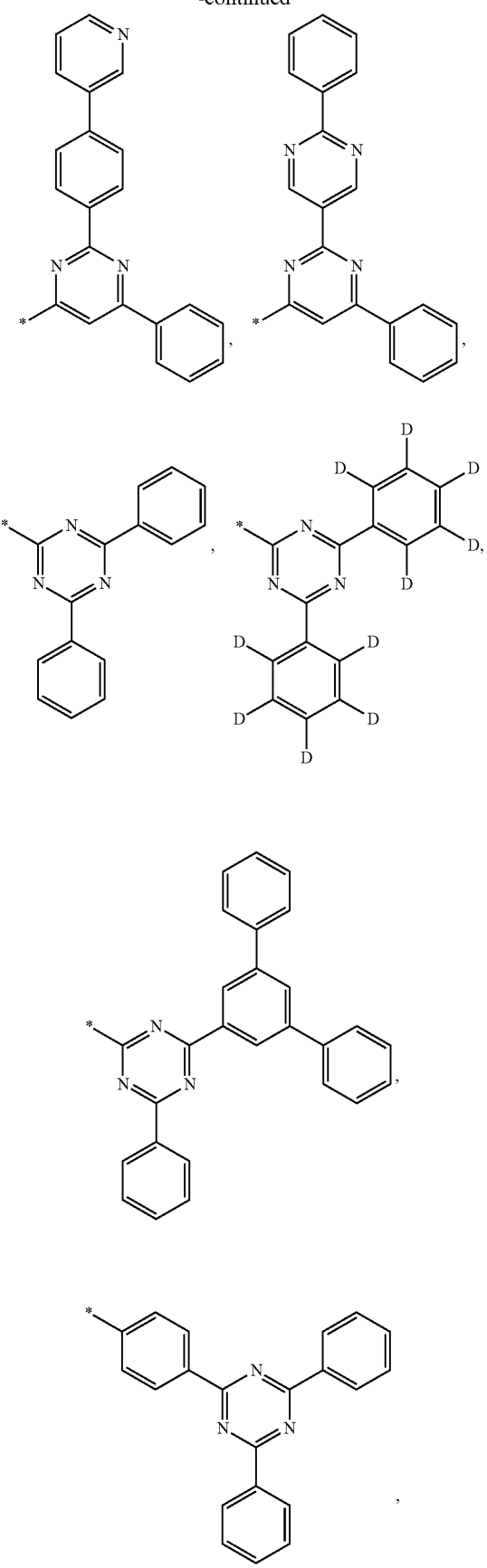

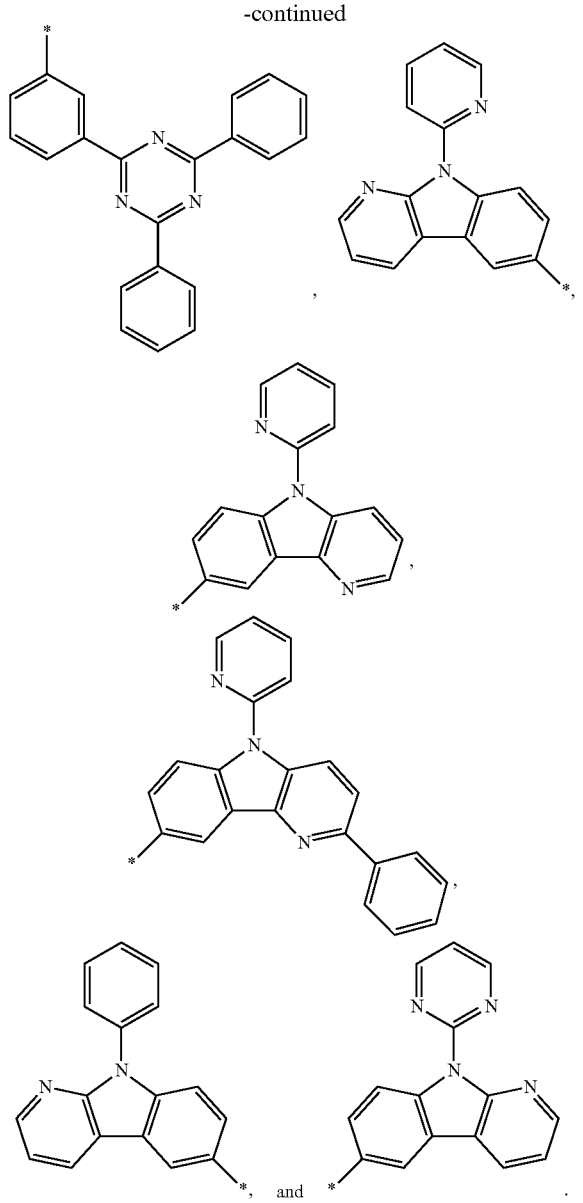

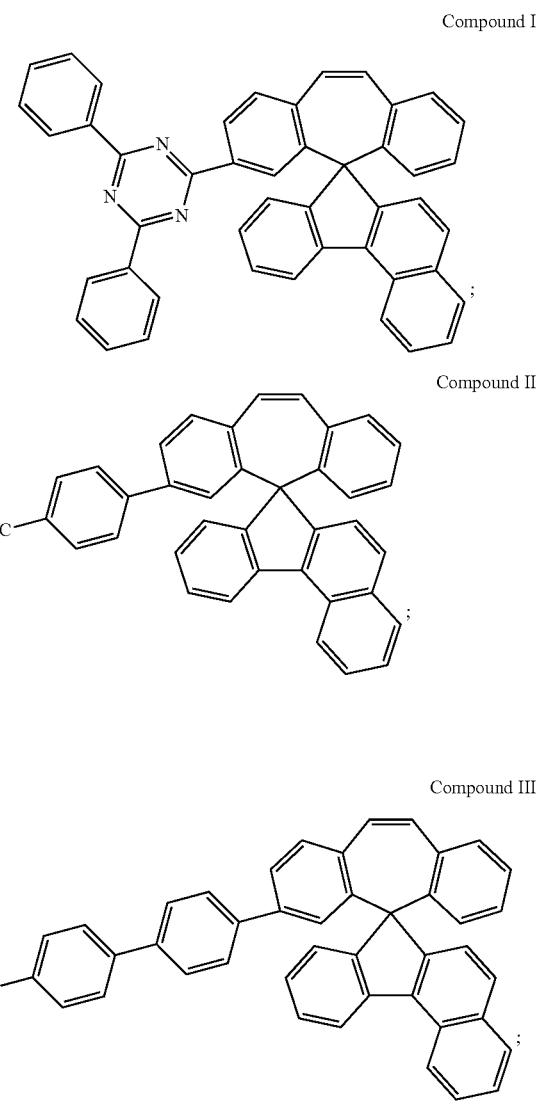

11. The compound as claimed in claim 1, wherein at least one of $Z^1$, $Z^2$, $Z^3$, $Z^6$, $Z^7$, and $Z^8$ in Formula (I) is a triazine group substituted with two phenyl groups, two pyridine groups, two pyrimidine groups, two pyrazine groups, two pyridazine groups, two phenylpyridine groups, two phenylpyrimidine groups, two phenylpyrazine groups, or two phenylpyridazine groups.

12. The compound as claimed in claim 1, wherein $Z^9$ and $Z^{10}$ are each independently selected from the group consisting of: a hydrogen atom, a deuterium atom, a trifluoromethyl group, a halogen group, a cyano group, a nitro group, an alkyl group having 1 to 40 carbon atoms, an alkenyl group having 2 to 40 carbon atoms, an alkynyl group having 2 to 40 carbon atoms, an aryl group having 6 to 60 ring carbon atoms, and a heteroaryl group having 3 to 60 ring carbon atoms.

13. The compound as claimed in claim 1, wherein $Z^1$, $Z^4$ to $Z^8$ are each independently a hydrogen atom or a deuterium atom.

14. The compound as claimed in claim 1, wherein $Z^1$, $Z^2$, $Z^4$, $Z^5$, $Z^7$, and $Z^8$ are each independently a hydrogen atom or a deuterium atom.

15. The compound as claimed in claim 1, wherein the compound is selected from the group consisting of:

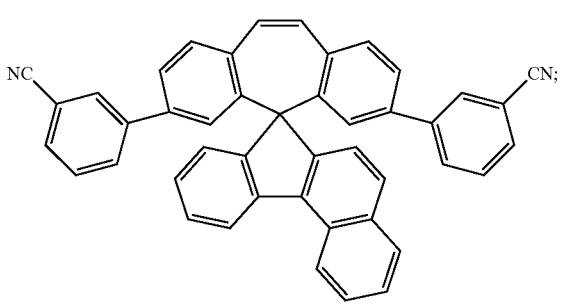

-continued
Compound V
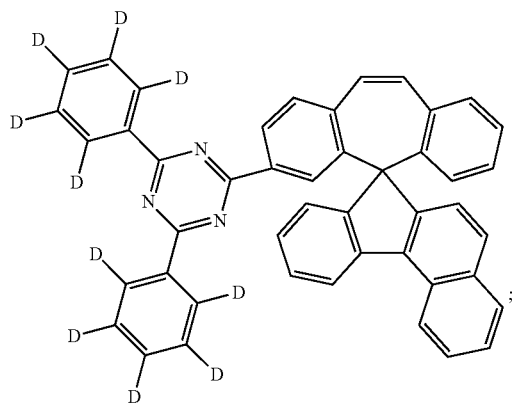
Compound VI
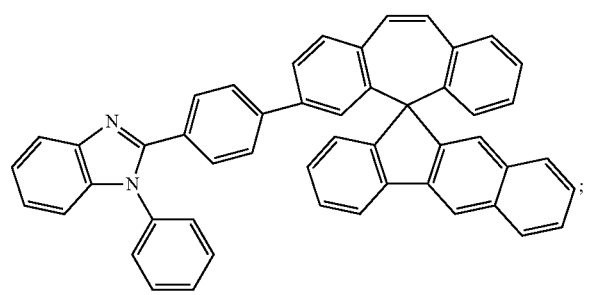
Compound VII
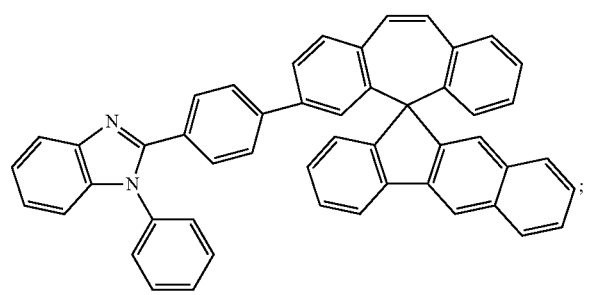
Compound VIII
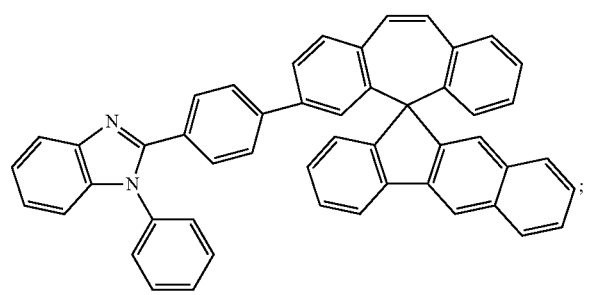
Compound IX
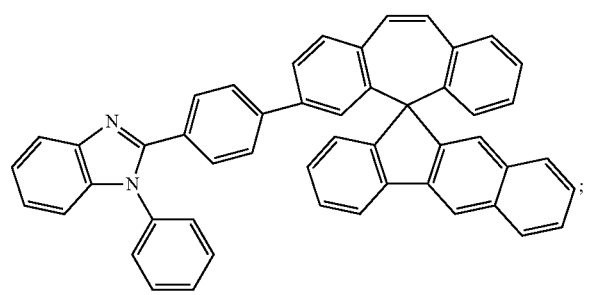
-continued
Compound X
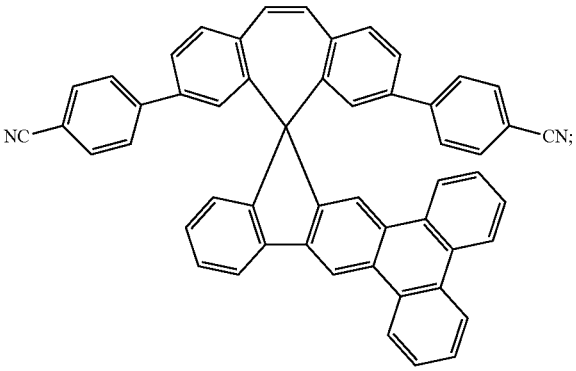
Compound XI
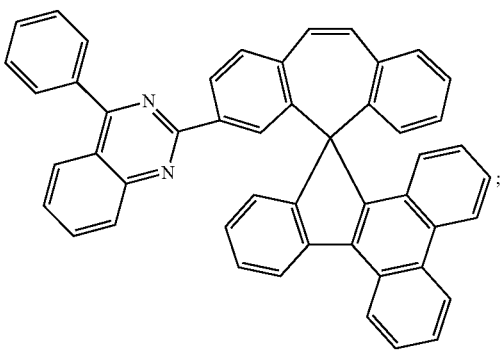
Compound XII
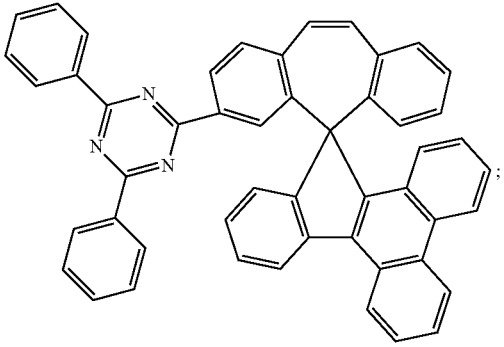
Compound XIII
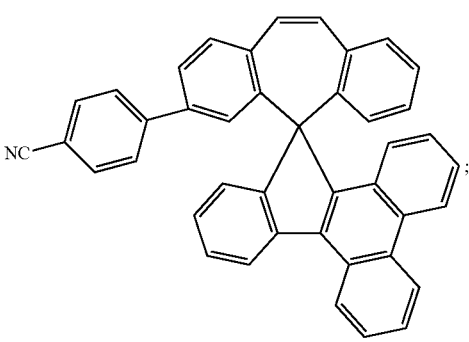

Compound XIV

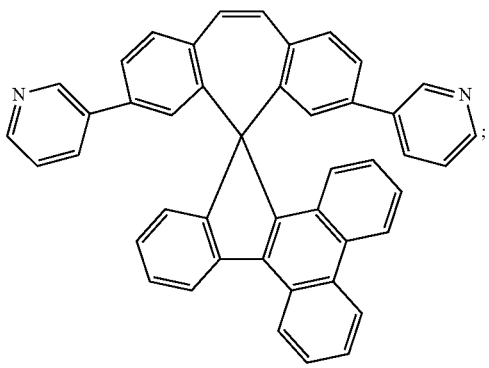

Compound XV

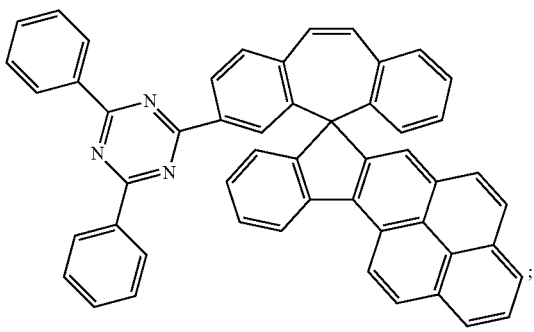

Compound XVI

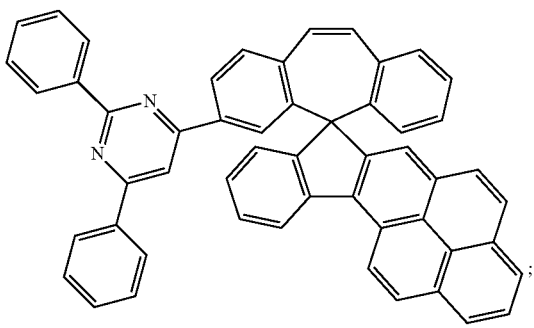

Compound XVII

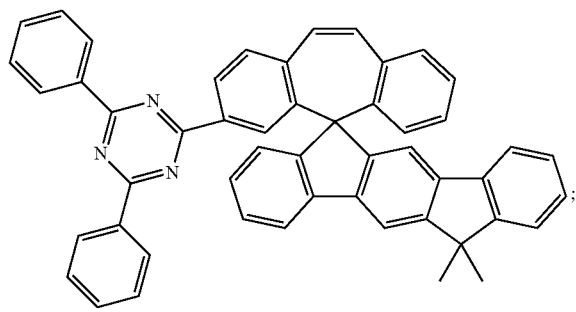

Compound XVIII

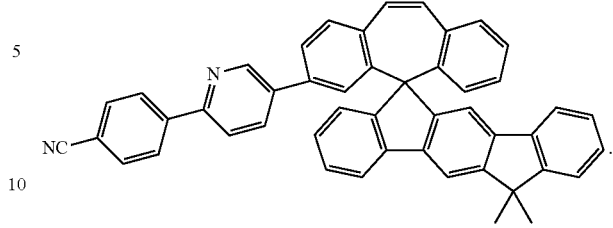

16. An organic electronic device, comprising a first electrode, a second electrode, and an organic layer disposed between the first electrode and the second electrode, wherein the organic layer comprises the compound as claimed in claim 1.

17. The organic electronic device as claimed in claim 16, wherein the organic electronic device is an organic light emitting device.

18. The organic electronic device as claimed in claim 17, wherein the organic light emitting device comprises:
   a hole injection layer formed on the first electrode;
   a hole transport layer formed on the hole injection layer;
   an emission layer formed on the hole transport layer;
   an electron transport layer formed on the emission layer, wherein the organic layer is the electron transport layer; and
   an electron injection layer formed between the electron transport layer and the second electrode.

19. The organic electronic device as claimed in claim 17, wherein the organic light emitting device comprises:
   a hole injection layer formed on the first electrode;
   a hole transport layer formed on the hole injection layer;
   an emission layer formed on the hole transport layer;
   a hole blocking layer formed on the emission layer, wherein the organic layer is the hole blocking layer;
   an electron transport layer formed on the hole blocking layer; and
   an electron injection layer formed between the electron transport layer and the second electrode.

20. The organic electronic device as claimed in claim 16, wherein the compound is selected from the group consisting of:

Compound I

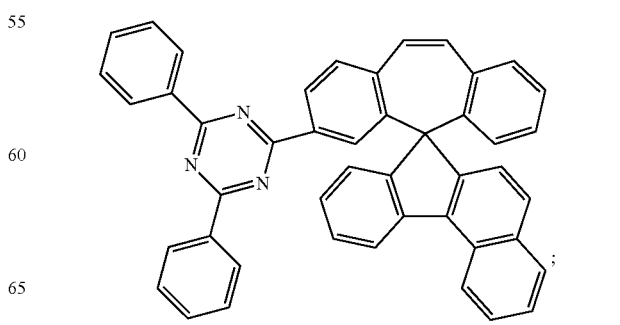

Compound II
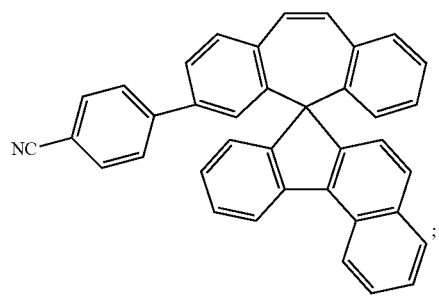
Compound III
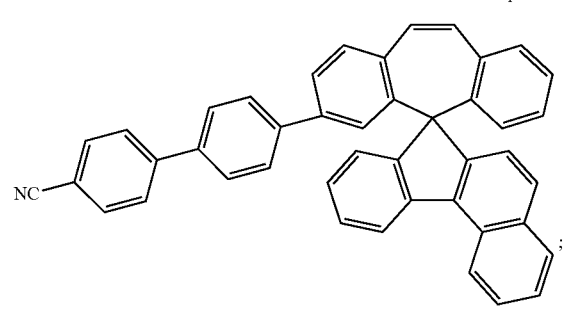
Compound IV
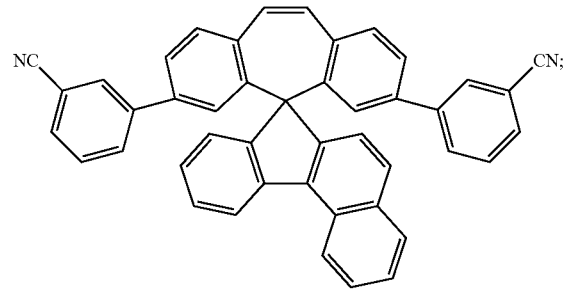
Compound V
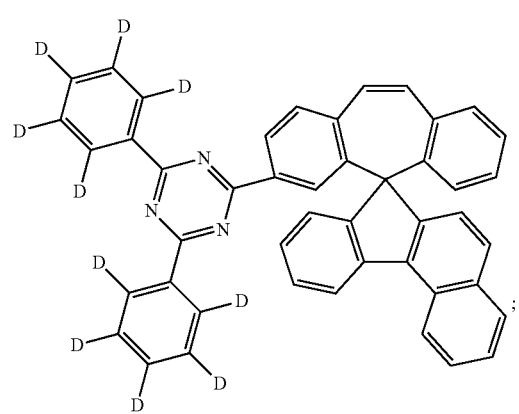
Compound VI
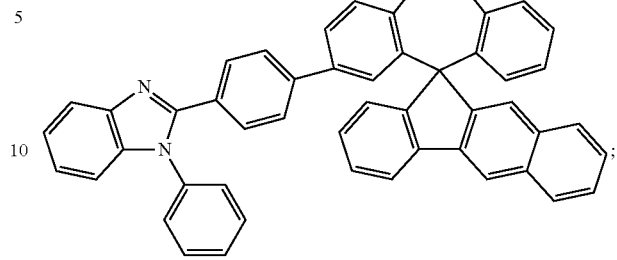
Compound VII
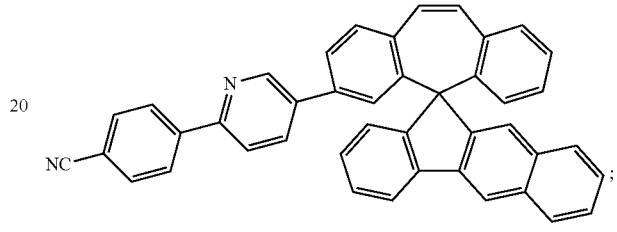
Compound VIII
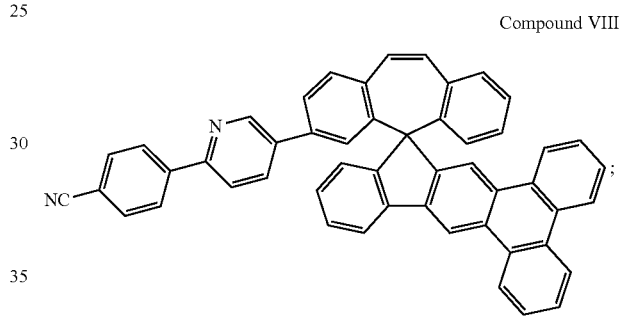
Compound IX
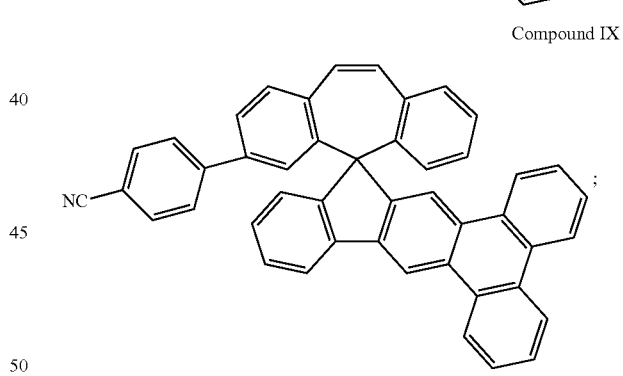
Compound X
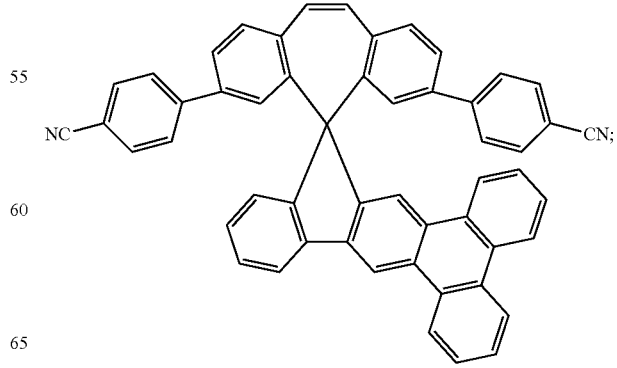

Compound XI
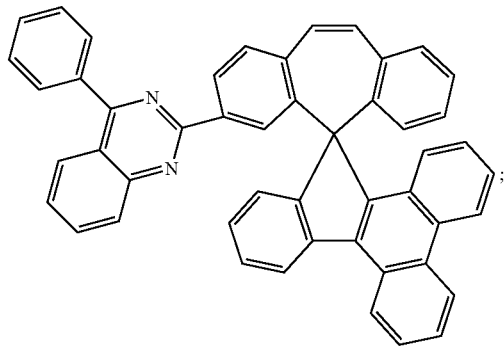
Compound XII
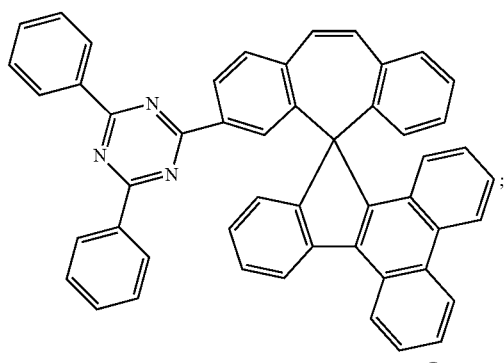
Compound XIII
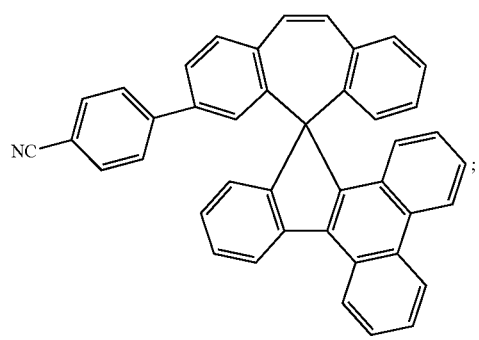
Compound XIV
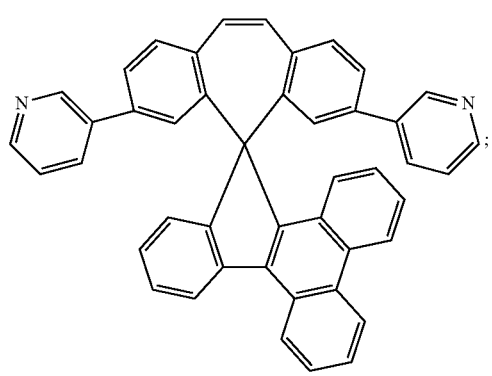
Compound XV
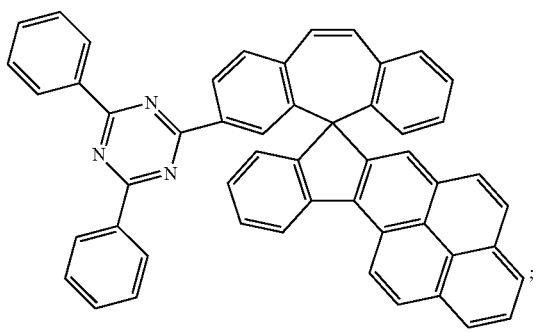
Compound XVI
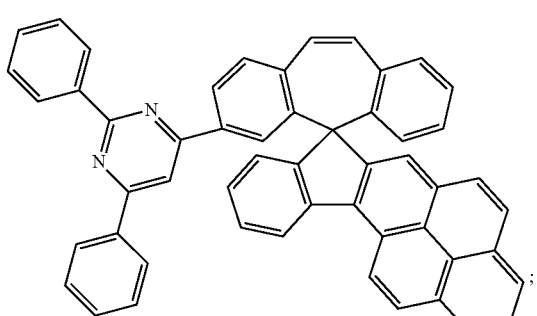
Compound XVII
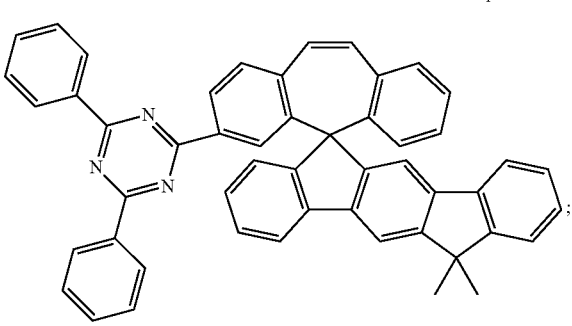
Compound XVIII
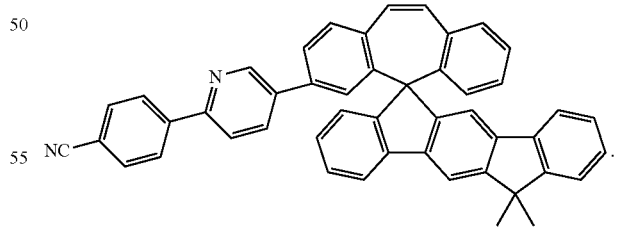
* * * * *